US012742162B2

(12) United States Patent
Zhong

(10) Patent No.: US 12,742,162 B2
(45) Date of Patent: Sep. 22, 2026

(54) CONJUGATES OF GUIDE RNA-CAS PROTEIN COMPLEX

(71) Applicant: Minghong Zhong, Burlingame, CA (US)

(72) Inventor: Minghong Zhong, Burlingame, CA (US)

( * ) Notice: Subject to any disclaimer, the term of this patent is extended or adjusted under 35 U.S.C. 154(b) by 1314 days.

(21) Appl. No.: 16/994,660

(22) Filed: Aug. 17, 2020

(65) Prior Publication Data

US 2021/0054371 A1 Feb. 25, 2021

Related U.S. Application Data

(63) Continuation-in-part of application No. PCT/US2020/036860, filed on Jun. 10, 2020.

(60) Provisional application No. 62/937,876, filed on Nov. 20, 2019, provisional application No. 62/914,565, filed on Oct. 14, 2019, provisional application No. 62/888,551, filed on Aug. 19, 2019.

(51) Int. Cl.

| | |
|---|---|
| ***C12N 15/11*** | (2006.01) |
| ***A61K 31/7052*** | (2006.01) |
| ***A61K 38/00*** | (2006.01) |
| ***A61K 38/16*** | (2006.01) |
| ***A61K 47/60*** | (2017.01) |
| ***A61K 48/00*** | (2006.01) |
| ***A61P 31/18*** | (2006.01) |
| ***A61P 31/20*** | (2006.01) |
| ***C12N 9/22*** | (2006.01) |
| ***C12N 9/96*** | (2006.01) |
| ***C12N 15/86*** | (2006.01) |
| ***C12N 15/90*** | (2006.01) |

(52) U.S. Cl.

CPC .......... *C12N 15/11* (2013.01); *A61K 31/7052* (2013.01); *A61K 38/164* (2013.01); *A61K 48/0008* (2013.01); *A61K 48/0058* (2013.01); *A61K 48/0066* (2013.01); *A61P 31/18* (2018.01); *A61P 31/20* (2018.01); *C12N 9/22* (2013.01); *C12N 9/226* (2025.05); *C12N 9/96* (2013.01); *C12N 15/86* (2013.01); *C12N 15/907* (2013.01); *C12N 2310/20* (2017.05); *C12N 2310/351* (2013.01); *C12N 2740/15043* (2013.01); *C12N 2750/14143* (2013.01); *C12N 2830/002* (2013.01)

(58) Field of Classification Search

CPC .......... C12N 2310/20; C12N 2310/351; C12N 2310/3519; C12N 2310/32–2310/3235; C12N 15/907; C12N 2310/321; C12N 2310/322; C12N 2310/3233; C12N 15/11; C12N 9/22; C12N 9/226; C12N 9/96; C12N 15/86; C12N 2740/15043; C12N 2750/14143; C12N 2830/002; C12N 15/1131; C12N 15/1132; C12N 2310/16; C12N 2310/3515; C12N 15/113; A61P 31/18; A61P 31/20; A61K 48/005; A61K 47/549; A61K 47/60; A61K 38/00; A61K 31/7052; A61K 38/164; A61K 48/0008; A61K 48/0058; A61K 8/0066

See application file for complete search history.

(56) References Cited

U.S. PATENT DOCUMENTS

| | | | | |
|---|---|---|---|---|
| 10,059,940 B2 | 8/2018 | Zhong | | |
| 11,236,313 B2 | 2/2022 | Cotta-Ramusino | | |
| 11,268,082 B2 | 3/2022 | Liu | | |
| 11,542,496 B2 | 1/2023 | Liu | | |
| 11,649,442 B2 | 5/2023 | Halperin | | |
| 11,649,443 B2 | 5/2023 | Halperin | | |
| 11,795,452 B2 | 10/2023 | Liu | | |
| 12,037,602 B2 | 7/2024 | Cleaver | | |
| 12,415,993 B2 | 9/2025 | Halperin | | |
| 12,435,331 B2 | 10/2025 | Liu | | |
| 12,497,601 B2 | 12/2025 | Halperin | | |
| 2015/0059010 A1* | 2/2015 | Cigan | C12N 15/8213 | 800/298 |
| 2015/0284727 A1* | 10/2015 | Kim | C12N 15/85 | 435/196 |

(Continued)

FOREIGN PATENT DOCUMENTS

| | | | |
|---|---|---|---|
| WO | WO-2016186745 A1 * | 11/2016 | C12N 15/111 |
| WO | WO-2017096041 A1 * | 6/2017 | A61K 31/7088 |

(Continued)

OTHER PUBLICATIONS

Chen et al. Sulfonyl group-containing compounds in the design of potential drugs for the treatment of diabetes and its complications . Current Medicinal Chemistry, vol. 19, pp. 3578-3604, 2012. (Year: 2012).*

'sulfones' in IUPAC Compendium of Chemical Terminology, 3rd ed. International Union of Pure and Applied Chemistry; 2006. Online version 3.0.1, 2019. https://doi.org/10.1351/goldbook.S06117, printed as p. 1/1. (Year: 2019).*

'sulfonamides' in IUPAC Compendium of Chemical Terminology, 3rd ed. International Union of Pure and Applied Chemistry; 2006. Online version 3.0.1, 2019. https://doi.org/10.1351/goldbook.S06114, printed as p. 1/1. (Year: 2019).* '

(Continued)

*Primary Examiner* — Abigail Vanhorn

(57) ABSTRACT

Provided herein are compositions of conjugates of a guide RNA(s)-CRISPR Cas protein (RNP) complex. The conjugate comprises a guide RNA(s)-CRISPR Cas protein (RNP) complex and one or more molecules selected from PEG, non-PEG polymers, ligands for cellular receptors, lipids, oligonucleotides, polysaccharides and peptides and chemically linked to the Cas protein and/or guide RNA(s). The conjugates are delivered to targeted cells as RNP complexes, or formed in targeted cells from guide RNA conjugates and an mRNA or a viral vector encoding a Cas protein, or formed in targeted cells from a crRNA conjugates and a viral vector encoding both a Cas protein and a tracrRNA. Also provided are preparation methods and uses of these conjugates.

31 Claims, 13 Drawing Sheets

Specification includes a Sequence Listing.

(56) References Cited

U.S. PATENT DOCUMENTS

| | | | | |
|---|---|---|---|---|
| 2016/0215275 | A1* | 7/2016 | Zhong | A61K 31/7105 |
| 2016/0362667 | A1* | 12/2016 | Donohoue | C12N 15/111 |
| 2017/0198302 | A1* | 7/2017 | Feng | C12N 15/102 |
| 2017/0306306 | A1 | 10/2017 | Potter | |
| 2019/0309275 | A1 | 10/2019 | Sargent | |
| 2019/0352626 | A1 | 11/2019 | Labs | |
| 2020/0017852 | A1 | 1/2020 | Lee | |
| 2021/0214724 | A1 | 7/2021 | Choudhary | |
| 2021/0238598 | A1* | 8/2021 | Kim | C12N 15/113 |
| 2022/0153779 | A1* | 5/2022 | Francis | A61K 47/54 |
| 2023/0167441 | A1 | 6/2023 | Zhong | |
| 2025/0027115 | A1 | 1/2025 | Zhong | |

FOREIGN PATENT DOCUMENTS

| | | | | |
|---|---|---|---|---|
| WO | WO-2018013525 | A1 * | 1/2018 | A61K 31/7088 |
| WO | WO-2019051097 | A1 * | 3/2019 | C12N 15/1024 |
| WO | WO-2020093025 | A1 * | 5/2020 | C12N 15/113 |
| WO | WO-2022034374 | A2 * | 2/2022 | C12N 15/102 |
| WO | WO2023101993 | A2 | 6/2023 | |
| WO | WO2023235501 | A1 | 12/2023 | |
| WO | WO2024211883 | A1 | 10/2024 | |
| WO | WO2025049563 | A1 | 3/2025 | |
| WO | WO2025101994 | A2 | 5/2025 | |
| WO | WO2026015421 | A1 | 1/2026 | |

OTHER PUBLICATIONS acyl groups' in IUPAC Compendium of Chemical Terminology, 3rd ed. International Union of Pure and Applied Chemistry; 2006. Online version 3.0.1, 2019. https://doi.org/10.1351/goldbook.A00123, printed as p. 1/1. (Year: 2019).*

McLeod. Tilde Symbol (~) Definition, Usage and Examples, printed from https://grammarist.com/punctuation/tilde-symbol/ on Jan. 4, 2024 as p. 1/5-5/5. (Year: 2024).*

Liang et al. Enhanced CRISPR/Cas9-mediated precise genome editing by improved design and delivery of gRNA, Cas9 nuclease, and donor DNA, pp. 136-146, pp. 1/2-2/2 of Supplemental Methods, and pp. 1/16-16/16 of Supplementary Figures, online Nov. 11, 2016. (Year: 2016).*

Batt, C.A. Chapter 14. Genetic Engineering of Food Proteins, in Food proteins and their applications. Ed. Srinivasan Damodaran, 1997, p. 425. (Year: 1997).*

Veronese et al. The impact of PEGylation on biological therapies. Biodrugs, vol. 22, No. 5, pp. 315-329, 2008. (Year: 2008).*

Lee et al. Synthetically modified guide RNA and donor DNA are a versatile platform for CRISPR-Cas9 engineering eLife 6:e25312. (Year: 2017).*

Lim et al., A conjugation platform for CRISPR-Cas9 allows efficient β-cell engineering, bioRxiv 732354. (Year: 2019).*

Halperin, Shakked O., et al. "CRISPR-guided DNA polymerases enable diversification of all nucleotides in a tunable window." Nature 560.7717 (2018): 248-252.*

Hiroshi Nishimasu, et al. Crystal Structure of Cas9 in Complex with Guide RNA and Target DNA. Cell 2014. 156, 935-949.

Yoo Kyung Kang, et al. Ca59 conjugate complex delivering donor DNA for efficient gene editing by homology-directed repair. Journal of Industrial and Engineering Chemistry 2021, 102, 241-250.

Eric J. Aird, et al. Increasing Cas9-mediated homology-directed repair efficiency through covalent tethering of DNA repair template. Communications Biology 2018, 1:54. pp. 1-6.

Zhong M, Zhao Q, Lin X, Guo J. Efficient and Precise Gene Editing by STAR (Seek-Tag-Amend-Release) Editing Enabled by Synergistic Actions of a Cas9 Nickase, a segNA (STAR Editing Guide Nucleic Acids) and a DNA Dependent Polymerase. ASGCT meeting abstract/Molecular Therapy 2024, 32(4S1), 357.

Zhong M, Zhao Q, Lin X, Guo J. Efficient and Precise Gene Editing by STAR (Seek-Tag-Amend-Release) Editing Enabled by Synergistic Actions of a Cas9 Nickase, a segNA (STAR Editing Guide Nucleic Acids) and a DNA Dependent Polymerase. Poster 740, ASGCT meeting May 7-11, 2024.

Zhong M, Zhao Q, Lin X, Srinivasan R, Guo J. LgRNA-Guided Precise CRISPR Gene Editing for the Cure of Chronic HBV Infection. ASGCT meeting abstract/Molecular Therapy 2023, 31(4S1), 260.

Zhong M, Zhao Q, Lin X, Srinivasan R, Guo J. LgRNA-guided Precise CRISPR Gene Editing for the Cure of Chronic HBV Infection. Poster 511, ASGCT meeting May 16-20, 2023.

Taemaitree L, Shivalingam A, El-Sagheer AH, Brown T. An artificial triazole backbone linkage provides a split-and-click strategy to bioactive chemically modified CRISPR sgRNA. Nat Commun. Apr. 8, 2019;10(1):1610.

* cited by examiner

SEQ ID NO: 35

CONJUGATES OF GUIDE RNA-CAS PROTEIN COMPLEX

CROSS REFERENCE TP RELATED APPLICATIONS

The present application claims the benefits of U.S. Provisional Application Ser. No. 62/888,551, filed on Aug. 19, 2019, Ser. No. 62/914,565, filed on Oct. 14, 2019, Ser. No. 62/937,876, filed on Nov. 20, 2019, and Ser. No. PCT/US2020/036860, filed on Jun. 10, 2020, the entire said inventions being incorporated herein by reference.

INCORPORATION BY REFERENCE OF SEQUENCE LISTING

The contents of the sequence listing text named "RNP_Conjugates_v15_ST25.txt", which was created on Jun. 18, 2024, and 55,752 bytes in size, are incorporated herein by reference in its entirety.

TECHNICAL FIELD OF THE INVENTION

The present invention relates to compositions of conjugates of a guide RNA(s)-Cas protein (RNP) complex and their uses as medicinal agents for treatment of viral infectious diseases and as gene regulation, disruption and/or correction-based therapeutics. The conjugate(s) comprises a guide RNA(s)-Cas protein (RNP) complex and one or more molecules selected from a group comprising PEG, non-PEG polymers, ligands for cellular receptors, lipids, oligonucleotides, antibodies, polysaccharides and peptides, and chemically linked to Cas protein and/or guide RNA(s). The guide RNA(s) is chemically modified to increase their stability, enhance the specificity for target recognitions and minimize/eliminate toxicities. The conjugates are delivered to targeted cells as RNP complexes, or formed in targeted cells from guide RNA conjugates and an mRNA or a plasmid or a viral vector encoding a Cas protein, or formed in targeted cells from a crRNA conjugate(s) and a plasmid or a viral vector encoding both a Cas protein and a tracrRNA. These conjugates are useful in improving preciseness in gene editing by driving templated DNA repair, in decreasing or preventing host preexisting immunity to guide RNA-Cas protein complexes by masking epitopes and chemical modifications of guide RNA(s), and also in improving the non-viral delivery of RNP complexes.

BACKGROUND OF THE INVENTION

The following description of the background is provided simply as an aid in understanding the present disclosure and is not admitted to describe or constitute prior art to the present disclosure.

The CRISPR-Cas system is an adaptive immune system of bacteria and composed of clustered regularly interspaced short palindromic DNA repeats and CRISPR-associated genes that protect bacteria against invading phages and mobile genetic elements. CRISPR-Cas9 is being developed for numerous applications in biotechnology and biomedical research and as a gene therapy agent for treatment of multiple conditions including cancers, infectious diseases, and genetic diseases such as sickle cell anemia and Duchenne's muscular dystrophy (DMD), with 33 trials around the world that involve CRISPR in human cells listed in the NIH's database of global clinical trials to date. Using CRISPR-Cas9 multiplexing gene editing, allogenic universal CAR T cells that are deficient in the TCR beta chain, B2M, PD-1, TCR and CTLA-4 have been produced, with enhanced potency. CRISPR-Cas9 has been applied to silencing/correcting pathogenic proteins in neurodegenerative diseases such as Alzheimer's disease, Huntington's disease, and Parkinson's disease, which should essentially block further progression of symptoms, and it may also be applicable for treatment of dementia with Lewy bodies, frontotemporal dementias, various other tauopathies and amyotrophic lateral sclerosis (ALS). Catalytically impaired Cas9 can target many genomic loci, which has led to technological developments such as base editing, prime editing, epigenetic editing, gene regulation, and chromatin imaging and modeling.

Chronic and/or latent viral infections such as HIV, HBV, and HSV cause enormous suffering, life loss, and financial burdening among the infected individuals. These infectious diseases are incurable, and contagious to variable degrees, and are prominent threats for public health, highlighting the urgent needs for curative therapies. To date, effective antiviral therapies only suppress viral replication but do not clear virus in patients, and do not target the viral genetic materials of latently integrated (e.g. proviral DNA) or non-replicating episomal viral genomes (such as cccDNA) in human cells. Nevertheless, these viral DNAs have been reported to directly cause these chronic or latent infections.

Several reports showed CRISPR-Cas9 as potential antiviral treatments targeting viral genomes such as HBV, HIV, HSV, and Epstein-Barr virus (EBV). Yang et al. reported the CRISPR/Cas9 system could significantly reduce the production of HBV core and surface proteins in Huh-7 cells transfected with an HBV-expression vector, and disrupt the HBV encoding templates both in vitro and in vivo, indicating its potential in eradicating persistent HBV infection. They observed that two combinatorial gRNAs targeting different sites could increase the efficiency in causing indels. The study by Seeger and Sohn also reported CRISPR/Cas9 efficiently inactivated HBV genes in NTCP encoding HepG2 cells permissive for HBV infection. Wang and Quake observed patient-derived cells from a Burkitt's lymphoma with latent Epstein-Barr virus infection presented dramatic proliferation arrest and a concomitant decrease in viral load after exposure to a CRISPR/Cas9 vector targeted to the viral genome and a mixture of seven guide RNAs at the same molar ratio via plasmid. Hu et al. reported CRISPR/Cas9 system could eliminate the integrated HIV-1 genome by targeting the HIV-1 LTR U3 region in single and multiplex configurations. It inactivated viral gene expression and replication in latently infected microglial, promonocytic, and T cells, completely excised a 9,709-bp fragment of integrated proviral DNA that spanned from its 5' to 3' LTRs, and caused neither genotoxicity nor off-target editing to the host cells. CRISPR-Cas9 has been most recently shown to clear HIV-1 in a subset of humanized mice, when used in combination with long-acting slow-effective release antiretroviral therapy, promising a cure for this so-far incurable disease (Dash et al. Nat. Comm. 2019, 10, 2753). More studies can be found in a recent review on antiviral applications of CRISPR-Cas9 (Lee, C. Molecules 2019, 24, 1349).

As supported by previous studies using in vitro or in vivo transcribed crRNAs or sgRNAs, targeting genes or viral DNA at multiple sites could enhance the effectiveness, which can be better practiced by delivering a mixture/chemical library of different chemically modified crRNAs, sgRNAs or lgRNAs (including various spacers), targeting multiple sites and/or variants/mutations of a single site in viral genomes (e.g., drug resistance variants or viral quasispecies) equivalent to combination therapies such as HAART.

SUMMARY OF THE INVENTION

This invention pertains to compositions of conjugates of a guide RNA(s)-Cas protein (RNP) complex and their uses as medicinal agents in treatment of viral infectious diseases and as gene regulation, disruption and/or correction-based therapeutics. The conjugate(s) comprises a guide RNA(s)-Cas protein (RNP) complex and one or more molecules selected from the group comprising PEG, non-PEG polymers, ligands for cellular receptors, lipids, oligonucleotides, antibodies, polysaccharides and peptides, and chemically linked to Cas protein and/or guide RNA(s). The conjugates are delivered to targeted cells as RNP complexes, or formed in targeted cells from guide RNA conjugates and an mRNA or a plasmid or a viral vector encoding a Cas protein delivered by co-injections or separate injections, or formed in targeted cells from a crRNA conjugates and a plasmid or a viral vector encoding both a Cas protein and a tracrRNA delivered by co-injections or separate injections. These conjugates are useful in improving preciseness in gene editing by driving templated DNA repair, in decreasing or preventing host preexisting immunity to guide RNA(s)-Cas protein complexes by masking epitopes and chemical modifications of guide RNA(s), and also in improving the non-viral delivery of RNP complexes.

The guide RNA(s) of said RNP complex conjugates is a chemically modified crRNA, dual guide RNAs (crRNA and tracrRNA), a sgRNA or a IgRNA oligonucleotide comprising nucleotides modified at sugar moieties such as 2'-deoxyribonucleotides, 2'-methoxyribonucleotides, 2'-F-ribonucleotides, 2'-F-arabinonucleotides, 2'-O,4'-C-methylene nucleotides (LNA), unlocked nucleotides (UNA), nucleoside phosphonoacetates (PACE), thiophosphonoacetates (thioPACE), and phosphoromonothioates:

II-27

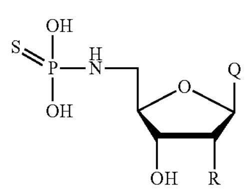

II-28

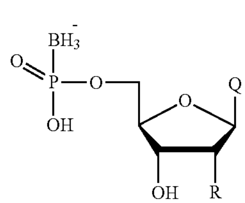

II-29

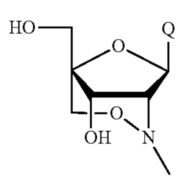

-continued

II-30

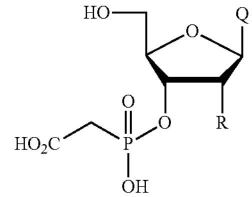

II-31

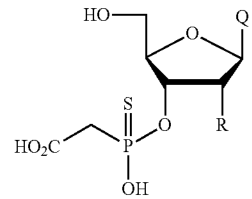

II-32

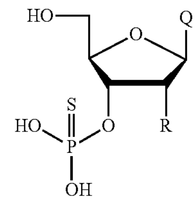

II-33

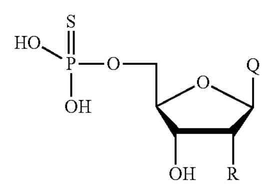

II-34

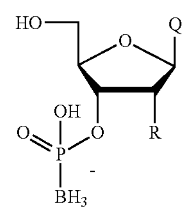

II-35

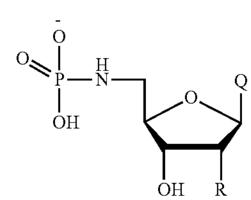

II-36

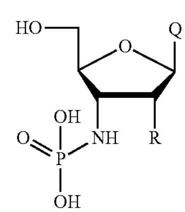

II-37

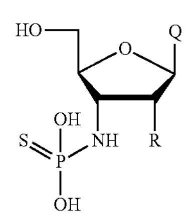

II-39
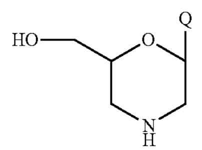
II-41
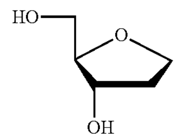
II-42
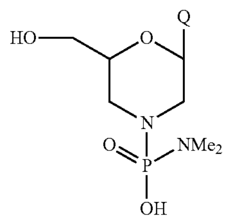
II-43
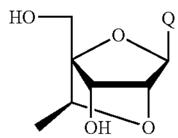
B-3
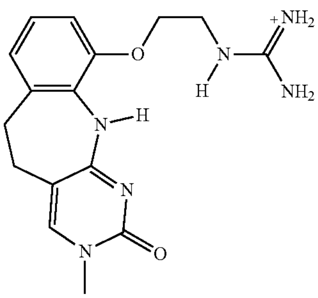
B-4
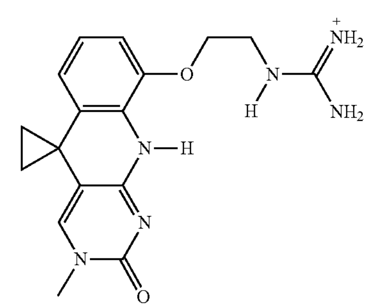
B-5
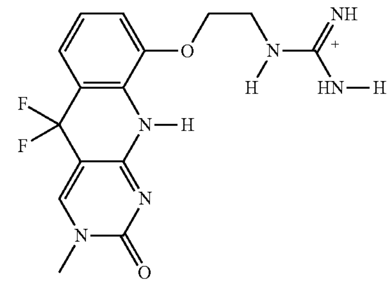
B-6
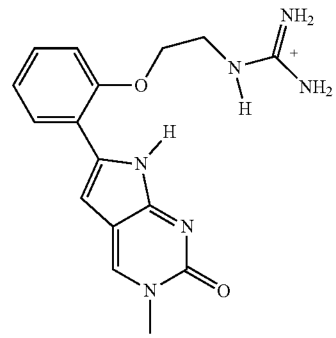
B-7
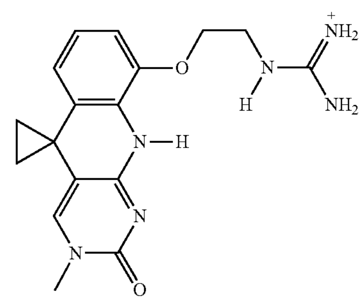
B-8
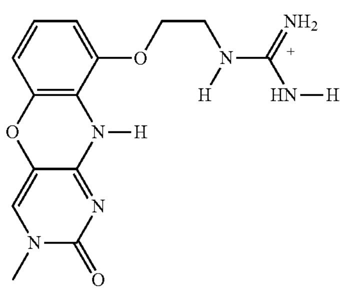
B-8-1
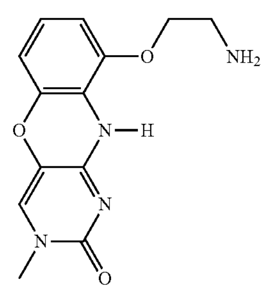

-continued
B-9
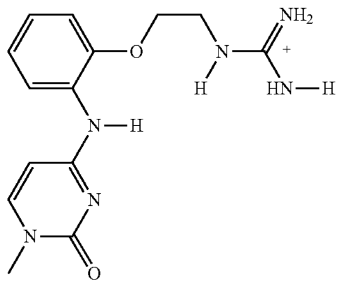
B-10
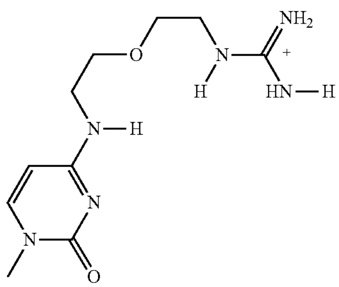
B-11
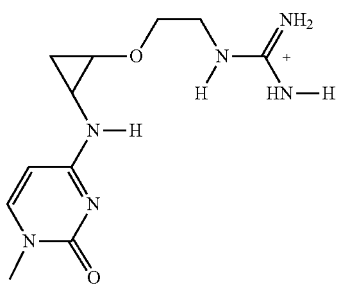
B-12
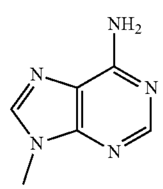
B-13
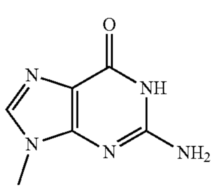
B-14
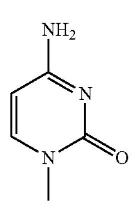
B-15
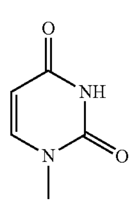
-continued
B-16
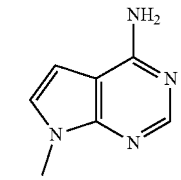
B-17
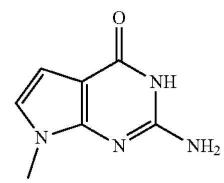
B-18
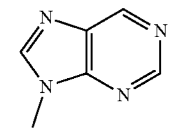
B-19
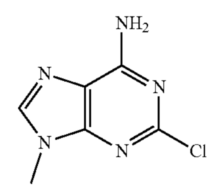
B-20
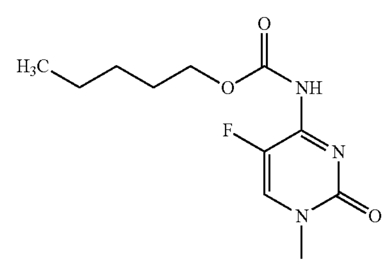
B-21
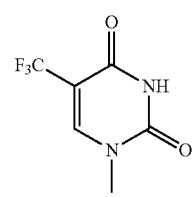
B-22
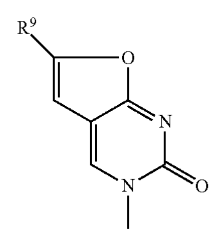
B-23
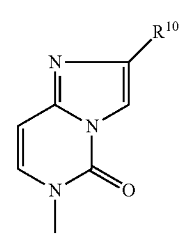

-continued
B-24
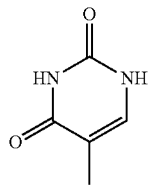
B-25
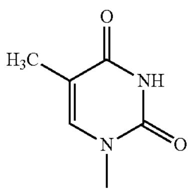
B-26
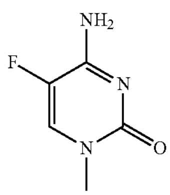
B-27
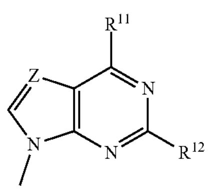
B-28
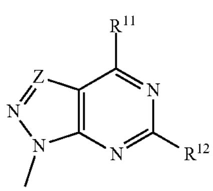
B-29
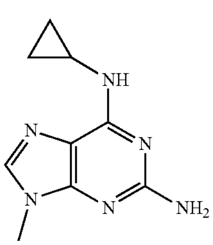
-continued
B-30
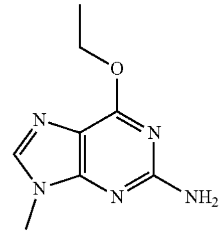
B-31
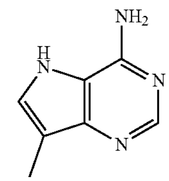
B-32
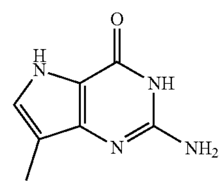
B-33
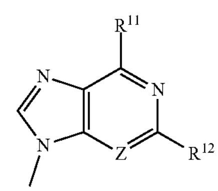
B-34
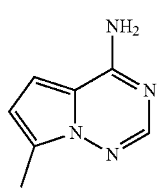

-continued

B-35

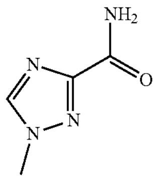

B-36

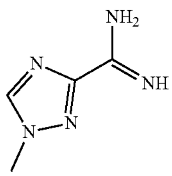

B-37

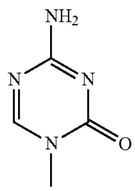

B-38

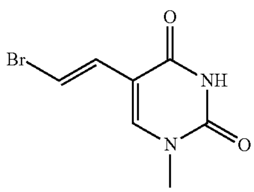

B-39

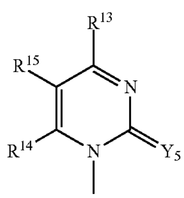

B-40

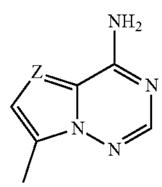

B-41

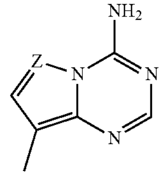

B-42

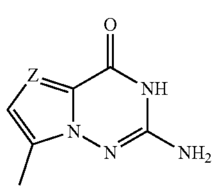

-continued

B-43

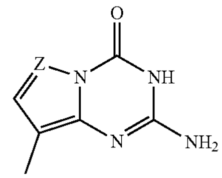

B-44

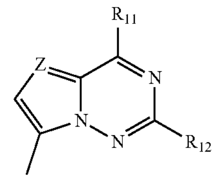

B-45

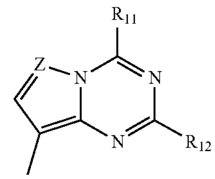

wherein:

(i) Z is N or $CR^{16}$; (ii) $R^9$, $R^{10}$, $R^{11}$, $R^{12}$, $R^{13}$, $R^{14}$, $R^{15}$ and $R^{16}$ are independently H, F, Cl, Br, I, OH, OR', SH, SR', SeH, SeR', $NH_2$, NHR', NHOH, NHOR', NR'OR', $NR'_2$, $NHNH_2$, $NR'NH_2$, NR'NHR', $NHNR'_2$, $NR'NR'_2$, lower alkyl of $C_1$-$C_6$, halogenated (F, Cl, Br, I) lower alkyl of $C_1$-$C_6$ lower alkenyl of $C_2$-$C_6$ halogenated (F, Cl, Br, I) lower alkenyl of $C_2$-$C_6$, CN, lower alkynl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, CN, $CO_2H$, $CO_2R'$, $CONH_2$, CONHR', $CONR'_2$, $CH{=}CHCO_2H$, or $CH{=}CHCO_2R'$, wherein R' is an optionally substituted alkyl which includes, but is not limited to, H, an optionally substituted $C_1$-$C_{20}$ alkyl, an optionally substituted lower alkyl, an optionally substituted cycloalkyl, an optionally substituted alkynyl of $C_2$-$C_6$, an optionally substituted lower alkenyl of $C_2$-$C_6$, an optionally substituted aryl, an optionally substituted heteroaryl, an optionally substituted sulfonyl, or optionally substituted acyl which includes but is not limited to C(=O) alkyl, or alternatively, in the instance of $NR'_2$, each R' comprise at least one C atom that are joined to form a heterocycle comprising at least two carbon atoms.

In some embodiments, chemical modifications of guide RNAs at either sugar or base moiety or both optimize the complementary recognition of the guide-target duplex to improve the cutting efficiency and lower the off-target effects.

In some embodiments, chemical modifications of guide RNAs at either sugar or base moiety or both optimize the shape complementarity between Cas protein and the minor and major grooves of the guide-target duplex to improve the efficiency and lower the off-target effects.

In some embodiments, the chemically modified crRNA, dual guide RNAs, sgRNA or lgRNA oligonucleotide is conjugated with peptides, aptamers, oligonucleotides, antibodies, small molecule receptor ligands such as GalNAc, biotin, cholesterol, tocopherol, lipid, or folate and etc., for selective tissue targeting. The conjugating sites are selected from 3'-end, 5'-end and ligation sites of these oligonucleotides.

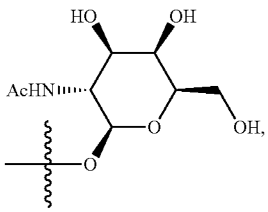
CONJ-1
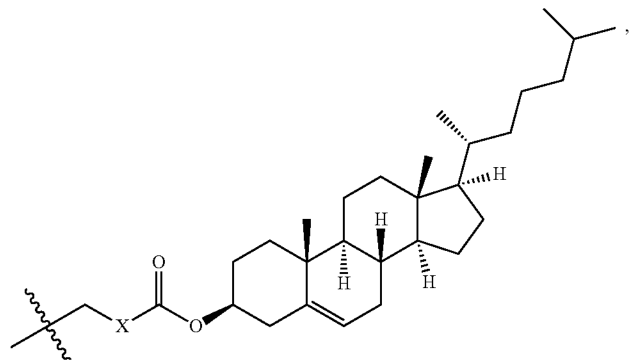
X = $CH_2$, NH
CONJ-2
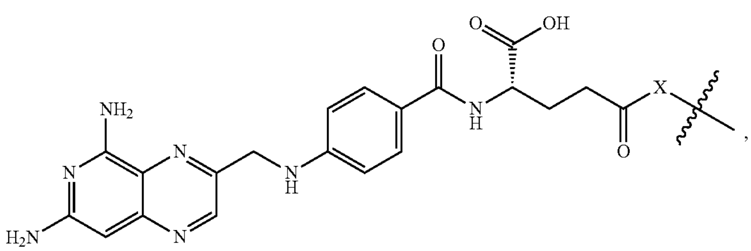
X = O, NH
CONJ-3
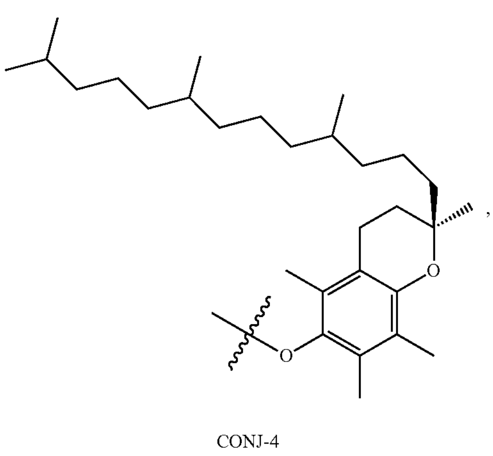
CONJ-4

-continued

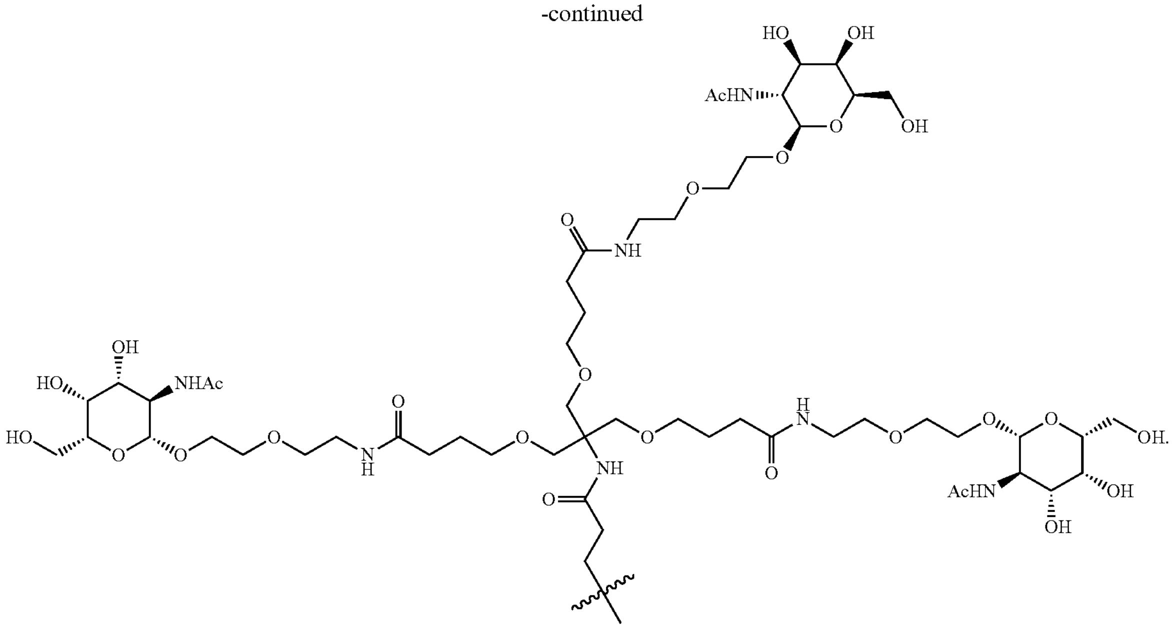

CONJ-5

In certain embodiments, the said viral vectors encoding both a Cas protein and a tracrRNA comprise the following elements, optionally in 5'>3' orientation: a mammalian promoter and optional enhancer, a cDNA encoding a single Cas protein, one or more nuclear localization sequence, a polyadenylation signal, a U6 promotor and the tracrRNA sequence. As an example, an adeno-associated virus (AAV) vector is depicted in FIG. 15.

In certain embodiments, the said viral vectors enabling targeted cells to stably express Cas comprise the following elements, optionally in 5'>3' orientation: a mammalian promoter and optional enhancer, a cDNA encoding a single Cas protein, one or more nuclear localization sequence, and a polyadenylation signal. As an example, an adeno-associated virus (AAV) vector is depicted in FIG. 16.

In some embodiments, the Cas protein is a Cas9.

In some embodiments, the cDNAs encoding Cas9 and/or tracrRNA of the said viral vectors are optimized to encode Cas9 variants and tracrRNA for both better efficacy and lower off-target and other side effects.

In some embodiments, the said viral vectors and crRNA(s), or lgRNAs or sgRNAs or their conjugates either in an aqueous solution with or without transfection reagents or packaged in a non-viral carrier, are administrated by co-injections or separate injections.

In some embodiments, the conjugates of functional ternary crRNA-tracrRNA-Cas9 complexes are formed cellularly or in vivo by either tracrRNA-Cas9 binary complex formation followed by hybridization of crRNA or crRNA conjugates to the bound tracrRNA via repeat: anti-repeat recognition and interactions with Cas9, or binding of Cas9 to a crRNA-tracrRNA complex or its conjugates dimerized via repeat: anti-repeat recognition. The conjugates of functional binary lgRNA/sgRNA-Cas9 complexes are formed in vivo by binding of stably or inducibly expressed Cas9 to exogenous lgRNA or sgRNA conjugates.

In certain embodiments, arrayed libraries of structurally optimized chemically modified lgRNAs or crRNAs or their conjugates and cells or animals stably or inducibly expressing a Cas protein or a Cas9-tracrRNA binary complex are used for drug discovery, medical research and biological studies, and genome wide screening.

In some embodiments, the Cas protein is a single protein effector of other class 2 CRISPR systems, such as a Cas12a protein, which is delivered in a tissue tropic viral vector, and chemically modified crRNA(s) or its conjugates are delivered either in an aqueous solution gymnotically or with transfection reagents or packaged in a non-viral carrier by co-injections or separate injections.

In some embodiments, the single protein effector such as Cas9 and Cas12a is catalytically inactive and coupled/fused with protein effectors such as transcription activators, transcription repressors, catalytic domains of DNA methyltransferase, histone acetyltransferase and deacetylase, reverse transcriptase, and nucleic acid deaminases, for gene editing and regulations.

In some embodiments, the said vectors and oligonucleotides or oligonucleotide conjugates are administrated to the target cells, i.e. T cells from patients, and the modified cells are infused back to the patients.

In another embodiment, the target tissue or cells are treated with the said vectors encoding a tracrRNA-Cas9 binary complex, and the modified cells are infused back to the patients. The said crRNAs or their conjugates are administrated to activate the CRISPR-Cas9 for regulation, disruption or correction of targeted genes or deactivation of viral genomes.

In yet another embodiment, the target tissue or cells are treated with the said vectors encoding the Cas9 protein, and the modified cells are infused back to the patients. The said lgRNAs or sgRNAs or their conjugates are administrated to activate the CRISPR-Cas9 for regulation, disruption or correction of targeted genes or viral genomes.

In some embodiments, a viral vector encoding a Cas9 orthologue has the tracrRNA encoded in cis, and crRNA(s) or crRNA conjugates are administrated either in an aqueous solution with or without transfection reagents, or packaged in a non-viral carrier, are administrated by co-injections or separate injections with administration ratios of the vector to copies of each crRNA ranging from 1:1 to 1:5. In some embodiments, a single crRNA or its conjugate is administrated. In some embodiments, a mixture of multiple crRNAs or their conjugates is administrated.

In some embodiments, a viral vector encoding a Cas9 orthologue, and lgRNA or lgRNAs or their conjugates either in an aqueous solution with or without transfection reagents, or packaged in a non-viral carrier, are administrated by co-injections or separate injections with administration ratios of the vector to copies of each lgRNA ranging from 1:1 to 1:5.

In certain embodiments, the viral vector is selected from engineered adeno-associated virus (AAV), retrovirus, lentivirus, adenovirus vehicles, etc.

In certain embodiments, the codons for Cas9 protein bearing a C-terminal SV40 nuclear localization signal are codon-optimized for human cells.

In certain embodiments, the expression of Cas9 protein is under the control of a single or a plurality of switchable transcription promotors/enhancers/depressors.

In certain embodiments, a Cas9 protein is selectively delivered to specific tissues based on tissue tropism of the viral vector and cell selective promotor of Cas9 gene.

In certain embodiments, crRNA, dual guide RNAs, sgRNA or lgRNA comprises a spacer selected from sequences of 12-20 nt of DNA genome of a pathogen, e.g. a virus, bacterium, or other microorganism that causes disease(s), of which each thymine is replaced with uracil, immediately next to a PAM (such as NGG for SpCas9). The spacer RNA oligomer has the same sequence as the sense non-target strand (5'→3') of the genome immediately next to the protospacer adjacent motif (PAM), and namely is its RNA transcript with or without further chemical modifications. The recognition of the complementary anti-sense target DNA strand by crRNA, sgRNA or lgRNA directs Cas DNA endonuclease for site-specific cleavage to form a specific double strand break (DSB) leading to degradation of viral genomes or deadly mutations for the pathogen resulting from DNA repair pathways via non-homologous end joining (NHEJ) and microhomology mediated end joining (MMEJ).

In certain embodiments, crRNA, sgRNA or lgRNA comprises a spacer selected from sequences of 12~20 nt of HIV genomes, of which each thymine is replaced with uracil, immediately next to a PAM (such as NGG). The spacer RNA oligomer has the same sequence as the sense strand (5'→3') of the genome, and namely is its RNA transcript with or without further chemical modifications.

In certain embodiments, crRNA, sgRNA or lgRNA comprises a spacer selected from sequences of 12~20 nt of HBV genomes, of which each thymine is replaced with uracil, immediately next to a PAM (such as NGG for SpCas9). The spacer RNA oligomer has the same sequence as the sense strand (5'→3') of the genome, and namely is its RNA transcript with or without further chemical modifications.

In certain embodiments, crRNA, sgRNA or lgRNA comprises a spacer selected from sequences of 12~20 nt of HSV genomes, of which each thymine is replaced with uracil, immediately next to a PAM (such as NGG for SpCas9). The spacer RNA oligomer has the same sequence as the sense strand (5'→3') of the genome, and namely is its RNA transcript with or without further chemical modifications.

In certain embodiments, crRNA, sgRNA or lgRNA comprises a spacer selected from sequences of 12~20 nt of EBV genomes, of which each thymine is replaced with uracil, immediately next to a PAM (such as NGG for SpCas9). The spacer RNA oligomer has the same sequence as the sense strand (5'→3') of the genome, and namely is its RNA transcript with or without further chemical modifications.

In certain embodiments, crRNAs, sgRNAs and lgRNAs comprise different spacers corresponding to different loci of viral genomes and/or variants of a single locus of target genomes.

In certain embodiments, crRNAs, sgRNAs and lgRNAs comprise spacers selected from sequences of 12~20 nt of host genes encoding host factors involved in viral entry, transcription/reverse transcription and/or replications, of which each thymine is replaced with uracil, immediately next to a PAM (such as NGG for SpCas9). The spacer RNA oligomers have the same sequences as the sense non-target strands (5'→3') of the genomes immediately next to the protospacer adjacent motif (PAM), and namely are their RNA transcripts with or without further chemical modifications. The recognition of the complementary anti-sense target DNA strand by crRNAs, sgRNAs or lgRNAs directs Cas DNA endonuclease for site-specific cleavage to form a specific double strand break (DSB), introducing mutations in these factors leading to host's resistance to the virus.

In certain embodiments, crRNAs, sgRNAs and lgRNAs comprise spacers selected from sequences of 12~20 nt of host mutated loci, defective gene or a target gene encoding a protein of defective or partial activity or function, of which each thymine is replaced with uracil, immediately next to a PAM (such as NGG for SpCas9). The spacer RNA oligomers have the same sequences as the sense non-target strands (5'→3') of the genomes immediately next to the protospacer adjacent motif (PAM), and namely are their RNA transcripts with or without further chemical modifications. The recognition of the complementary anti-sense target DNA strand by crRNAs, sgRNAs or lgRNAs directs Cas DNA endonuclease for site-specific cleavage to form a specific double strand break (DSB), allowing a transgene cassette flanked with homologous regions to recombine with the host loci and replace the mutated DNA with the correct sequence.

In certain embodiments, the said transgene cassette is contained in an ssDNA HDR template conjugated to guide RNAs to form a guide RNA(s)-ssDNA conjugate for replacing a mutated DNA with its correct sequence.

In certain embodiments, the said transgene cassette is contained in an ssDNA HDR template conjugated to guide RNAs for editing viral episomal DNAs and integrated viral DNAs in host genes, and the editions are deletions, insertions or point mutations to suppress or eliminate viral protein expression, or overexpression of host pathogenic proteins upregulated by viral DNA integration.

In certain embodiments, the said editions incorporate stop codon(s) and/or cis regulatory elements to suppress or eliminate viral protein expression, or overexpression of host pathogenic proteins upregulated by viral DNA integration.

In certain embodiments, the said guide RNA(s)-ssDNA conjugates are optionally further conjugated with peptides, aptamers, antibodies, small molecule receptor ligands such as GalNAc, cholesterol, tocopherol, lipids, or folate, etc., for selective tissue targeting. The conjugating sites are selected from 3'-end, 5'-end and ligation sites of these said guide RNA(s)-ssDNA conjugates.

The Cas protein is selected from Cas9 variants comprising SpCas9, St1Cas9, SaCas9, NmCas9, etc. (Jin et al. Adv. Sci. 2020, 1902312; Doudna, J. A. Nature 2020, 578, 229), and can be a nickase or catalytically inactive Cas9 (dCas9) coupled/fused with protein effectors such as transcription activators, transcription repressors, catalytic domains of DNA methyltransferase, histone acetyltransferase and deacetylase, reverse transcriptase and nucleic acid deaminases, for gene editing and regulations.

The Cas protein can be alternatively any single protein effector of other class 2 CRISPR systems (Type V and VI), such as a Cas12 (a, b, c, e, g, h, i, etc.), Cas13 and Cas14 protein. The single protein effector such as Cas12 and Cas14 can be catalytically inactive and coupled/fused with protein effectors such as transcription activators, transcription repressors, catalytic domains of DNA methyltransferase, histone acetyltransferase and deacetylase, and nucleic acid deaminases, reverse transcriptase, for gene editing and regulations.

In certain embodiments, the Cas protein is optionally engineered to introduce conjugating cysteines to replace selected solvent exposed amino acids near to or contained by epitopes by site directed mutagenesis, and cysteines of wild type enzymes (e.g. C80 and C573 of SpCas9) are optionally mutated to avoid potential deactivation of enzymes due to conjugations at these cysteines.

In certain embodiments, the guide RNA(s)-Cas protein (RNP) complex(es) is conjugated with molecules selected from PEG, non-PEG polymers, ligands for cellular receptors, antibodies, lipids, oligonucleotides, polysaccharides, glycans and peptides.

In certain embodiments, the Cas conjugating sites are selected from surface/solvent exposed/protruded amino acid residues such as lysine, arginine, serine, cysteine, aspartate, or glutamate of Cas proteins or an amino acid(s), e.g. a cysteine, introduced by site-directed mutagenesis for selective conjugations to mask or shield epitopes.

In certain embodiments, the guide RNA(s)-Cas protein (RNP) complex(es) is conjugated at either Cas protein, or guide RNAs, or both.

In certain embodiments, the guide RNA(s)-Cas protein (RNP) complex(es) is PEGylated.

In certain embodiments, the guide RNA(s)-Cas protein (RNP) complex(es) is PEGylated with more than two PEG polymers to shield/mask epitopes.

In certain embodiments, the guide RNA(s)-Cas protein (RNP) complex(es) are conjugated with other non-PEG polymers, ligands for cellular receptors, lipids, oligonucleotides, antibodies, polysaccharides, glycans or peptides.

In certain embodiments, PEG-conjugated guide RNA-Cas protein (RNP) complex(es) is further covalently linked to other non-PEG polymers, ligands for cellular receptors, lipids, oligonucleotides, antibodies, polysaccharides, glycans or peptides.

In certain embodiments, guide RNA(s)-Cas protein (RNP) complex(es) is covalently linked to one or more molecules selected from PEG, non-PEG polymers, ligands for cellular receptors, lipids, oligonucleotides, antibodies, polysaccharides, glycans and peptides.

In certain embodiments, guide RNA(s)-conjugates, e.g. IgRNA-ssDNA conjugates, are delivered with an mRNA or a vector encoding a Cas protein.

In certain embodiments, guide RNA(s)-conjugates, e.g. IgRNA-ssDNA conjugates, are delivered to cells stably or inducibly expressing a Cas protein.

In certain embodiments, lgRNA-ssDNA conjugates are used to drive the templated repair of the cleaved/nicked DNA upon hybridization of ssDNA with the PAM distal fragment of the R-loop asymmetrically released from Cas9: lgRNA:DNA complexes, and thus to promote precise editing and fast release of the RNP complex from the edited DNA to increase its turnover frequency (TOF).

In certain embodiments, lgRNA-ssDNA conjugates are used to drive the templated repair of the cleaved/nicked DNA upon hybridization of ssDNA with the 3'-OH fragment of the R-loop in Cas:lgRNA:DNA complexes, and thus to promote precise editing and fast release of the RNP complex from the edited DNA to increase its turnover frequency (TOF).

DETAILED DESCRIPTION OF THE INVENTION

The most commonly used type of CRISPR system for gene regulation, disruption or correction to date is type II represented predominantly by Cas9. CRISPR-Cas9 is a naturally occurring defense system of bacteria. The CRISPR Cas9 endonuclease is activated by the binding of crRNA: tracrRNA and responds specifically to the DNA sequence (target strand) complementary to the spacer in crRNA and cleaves it upon the recognition of a protospacer adjacent motif (PAM) on the 3'-end of the non-target DNA strand. The presence of tracrRNA and Cas9 is required for processing pre-crRNA into individual crRNA by a double-stranded RNA specific ribonuclease, RNase III, forming crRNA: tracrRNA duplexes. This duplex was fused into an artificial single guide RNA (sgRNA via nucleotide tetraloop or lgRNA via a non-Nucleotide linker) for genome engineering purpose and other applications.

Attractive alternatives include other class 2 CRISPR systems such as Type V and VI.

An aspect of the invention is directed to compositions of PEGylated guide RNA(s)-Cas protein complex(es) and their uses as medicinal agents in treatment of viral infectious diseases and as gene regulation, disruption and/or correction based therapeutics. The PEG polymers can be other polymers, ligands for cellular receptors, lipids, oligonucleotides, antibodies, polysaccharides or peptides, conjugated to Cas protein and/or guide RNA(s).

In some embodiments, the crRNAs, sgRNAs and lgRNAs are chemically modified for optimization for better efficiency in cleaving target DNAs such as viral genomic DNAs and for minimizing off-target cleavages of host genomic DNAs with or without engineering Cas proteins.

In some embodiments, the crRNAs, sgRNAs or lgRNAs are chemically modified and conjugated with one or more ssDNA donor templates.

In some embodiments, the lgRNA-Cas protein complex conjugates are administrated to edit pathogenic genes, of which the lgRNA or lgRNA conjugate comprises one or more chemically ligated ssDNA donor template including optional chemical modifications.

In some embodiments, the pathogenic genes are episomal and integrated viral DNA.

In some embodiments, the pathogenic genes are mutated host genes or any genes to be edited.

An aspect of the invention is directed to compositions of viral vectors encoding a tracrRNA-Cas protein binary complex, and chemically modified oligonucleotides of crRNAs or crRNA conjugates, both of which are delivered to the same targeted cells, preparation methods of said compositions, and uses as therapeutic agents in treatment of viral infectious diseases and as gene regulation, disruption and/or correction based therapeutics, and a method to deliver a tracrRNA-Cas protein binary complex in a tissue tropic viral vector and chemically modified crRNA(s) or crRNA conjugate with cell targeting ligands either in an aqueous solution gymnotically or with transfection reagents or in a non-viral carrier by co-injections or separate injections.

Another aspect of the invention is directed to compositions of viral vectors encoding a Cas protein, and chemically modified oligonucleotides of lgRNAs, sgRNAs or lgRNA/sgRNA conjugates delivered to the same targeted cells, and a method to deliver a Cas protein in a tissue tropic viral vector and chemically modified lgRNA(s), sgRNAs or lgRNA/sgRNA conjugates with cell targeting ligands either in an aqueous solution gymnotically or with transfection reagents or in a non-viral carrier by co-injections or separate injections, in treatment of viral infectious diseases and as therapeutics based on gene disruption and/or correction.

Yet another aspect of the invention is directed to compositions of viral vectors encoding a Cas protein, which functions in the absence of a tracrRNA, and chemically modified oligonucleotides of crRNAs or crRNA conjugates, delivered to the same targeted cells, and a method to deliver Cas protein in a tissue tropic viral vector and chemically modified crRNA(s) or crRNA conjugates either in an aqueous solution gymnotically or with transfection reagents or in a non-viral carrier by co-injections or separate injections, in treatment of viral infectious diseases and as therapeutics based on gene disruption and/or correction.

In some embodiments, the crRNA, sgRNA and lgRNA or their conjugates are chemically modified for optimization for better efficiency in cleaving target DNAs such as viral genomic DNAs and for minimizing off-target cleavages of host genomic DNAs with or without engineering Cas proteins.

In some embodiments, the Cas protein is engineered, or a CRISPR-associated protein of smaller size thus more amenable to viral delivery in human cells, for efficient administrations and better dosage forms.

In other embodiments, the said compositions are administrated, either alone or in combination with small molecule therapeutic agents, therapeutic proteins such as antibodies, or nuclei acids such as mRNAs, antisense oligonucleotides and small interfering RNAs.

DEFINITION

Figure 1:
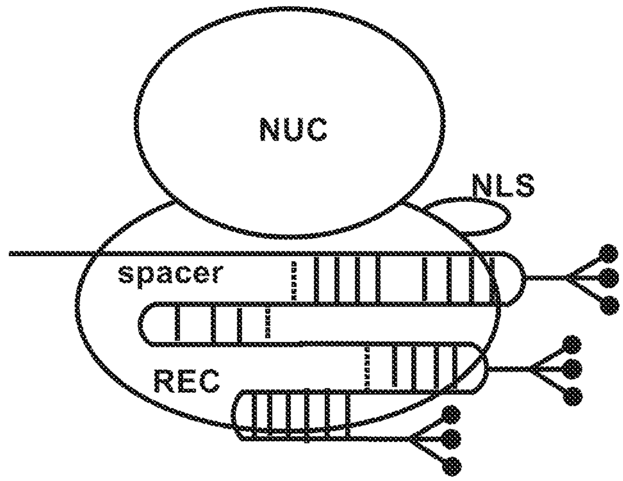
FIG. 1: Schematic structure of a Cas9/lgRNA complex conjugate.
Figure 2:
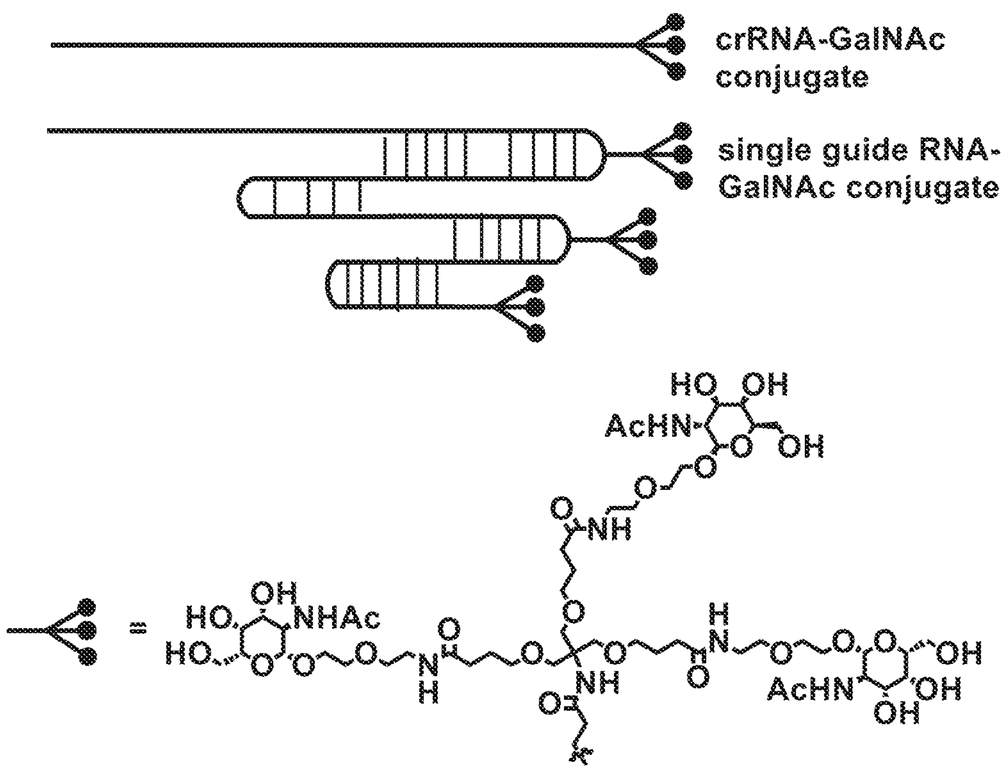
FIG. 2: Schematic structures of guide RNAs conjugated with tris-GalNAc ligand(s).
Figure 3:
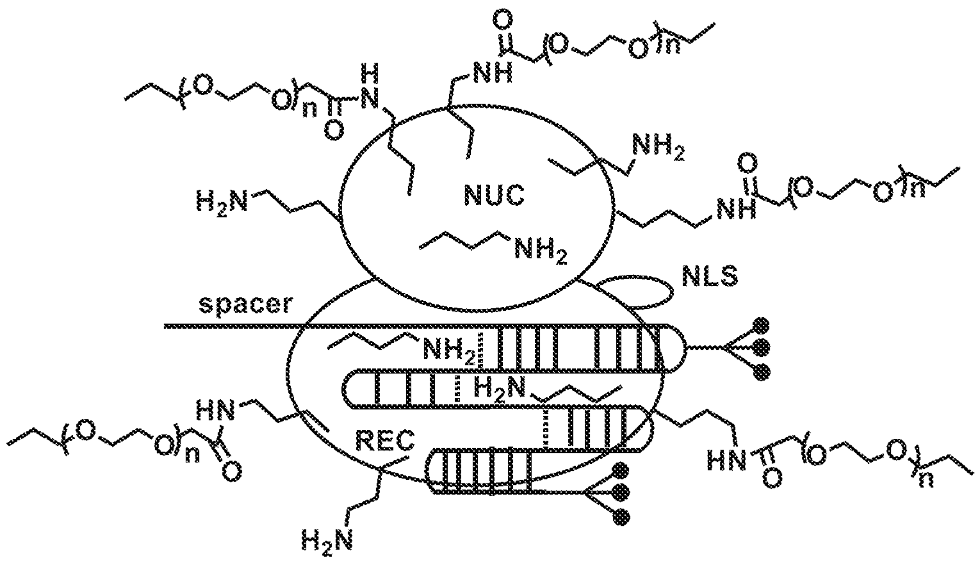
FIG. 3: Schematic structure of a PEGylated Cas9/lgRNA complex with guide RNAs conjugated with tris-GalNAc(s).
Figure 4:
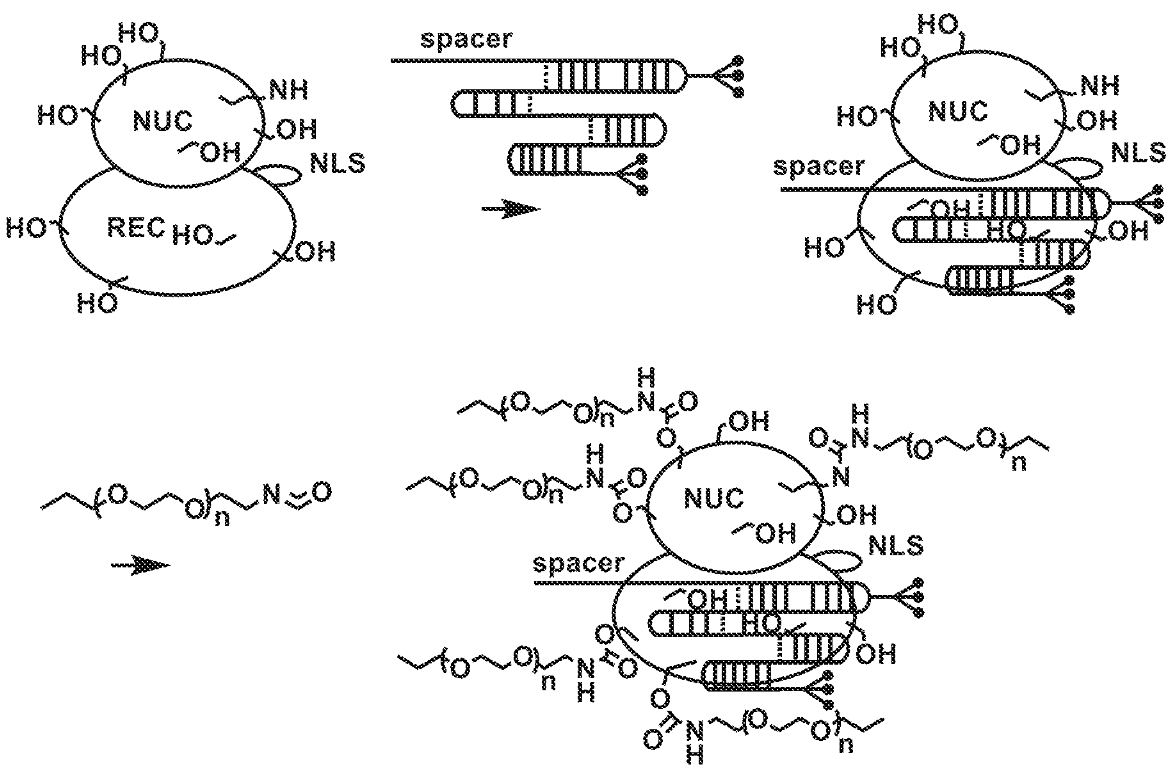
FIG. 4: Method to prepare a PEGylated Cas9/lgRNA complex by selective conjugations at serine and lysine residues of a preformed RNP complex.
Figure 5:
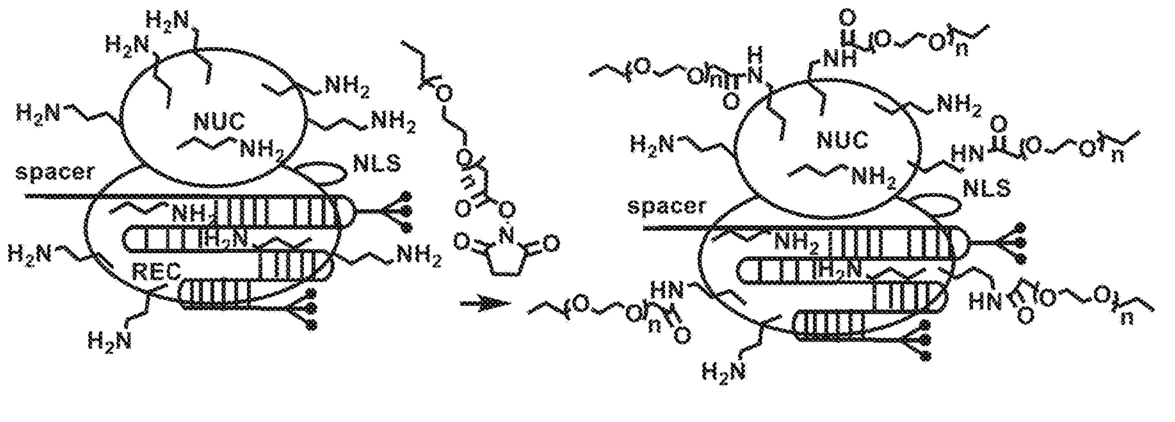
FIG. 5: Method to prepare a PEGylated Cas9/lgRNA complex by selective conjugations at lysine residues of a preformed RNP complex.
Figure 6:
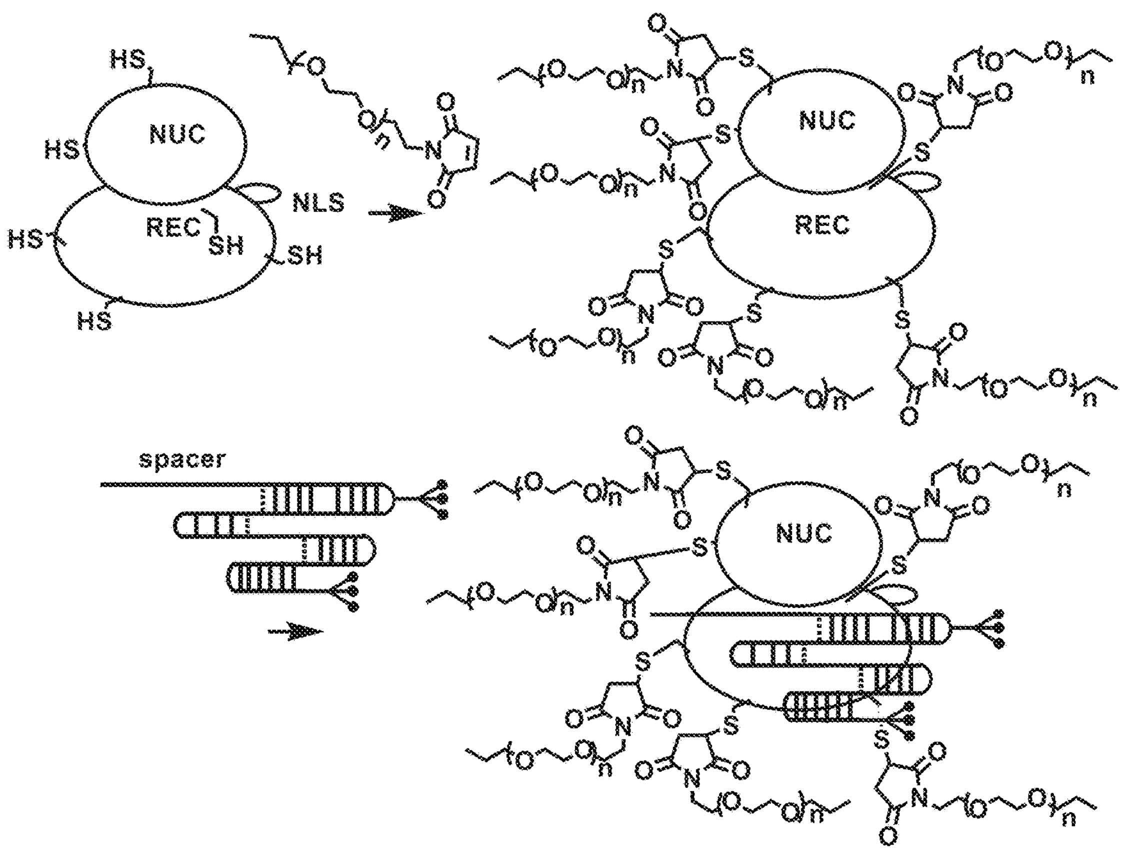
FIG. 6: Method to prepare a PEGylated Cas9/lgRNA complex by selective conjugations at cysteine residues of an engineered Cas protein obtained by site-directed mutagenesis, followed by RNP formation.

The definitions of terms used herein are consistent to those known to those of ordinary skill in the art, and in case of any differences the definitions are used as specified herein instead.

The term "nucleoside" as used herein refers to a molecule composed of a heterocyclic nitrogenous base, containing an N-glycosidic linkage with a sugar, particularly a pentose. An extended term of "nucleoside" as used herein also refers to acyclic nucleosides and carbocyclic nucleosides.

The term "nucleotide" as used herein refers to a molecule composed of a nucleoside monophosphate, di-, or triphosphate containing a phosphate ester at 5'-, 3'-position or both. The phosphate can also be a phosphonate, phosphoramidate, phosphorodiamidate, phosphonoacetate (PACE), thiophosphonoacetate (thioPACE), or phosphoromonothioate.

The term of "oligonucleotide" (ON) is herein used interchangeably with "polynucleotide", "nucleotide sequence", and "nucleic acid", and refers to a polymeric form of nucleotides of any length, either deoxyribonucleotides or ribonucleotides, or analogs thereof. An oligonucleotide may comprise one or more modified nucleotides, which may be imparted before or after assembly of such an oligonucleotide. The sequence of nucleotides may be interrupted by non-nucleotide components.

The term of "CRISPR-Cas system" refers a prokaryotic immune system that confers resistance to foreign genetic elements such as those present within plasmids and phages that provides a form of acquired immunity. RNA harboring the spacer sequence helps Cas (CRISPR-associated) proteins recognize and cut foreign pathogenic DNA. Other RNA-guided Cas proteins cut foreign RNA. CRISPR are found in approximately 50% of sequenced bacterial genomes and nearly 90% of sequenced archaea. The system is being engineered for gene regulation and editing, insertion, disruption and/or correction in eukaryotic cells.

The term of "CRISPR/Cas9" refers to the type II CRISPR-Cas system such as SpCas9 from *Streptococcus pyogenes*. The type II CRISPR-Cas system comprises protein Cas9 and two noncoding RNAs (crRNA and tracrRNA). These two noncoding RNAs were further fused into one single guide RNA via a tetraloop (sgRNA) and a chemically ligated guide RNA via one or more nNt-Linkers (lgRNA). The Cas9/sgRNA or Cas9/lgRNA complex binds double-stranded DNA sequences that contain a sequence match to the first 17-20 nucleotides of the guide RNA(s) and immediately before a protospacer adjacent motif (PAM). Once bound, two independent nuclease domains (HNH and RuvC) in Cas9 each cleaves one of the DNA strands 3 bases (HNH) or more (RuvC) upstream of the PAM, leaving a DNA double stranded break (DSB).

The term of "Cas protein" refers to a class 2 CRISPR-Cas protein.

The term of "off-target effects" refers to non-targeted cleavage of the genomic DNA target sequence by Cas9 or any other Cas protein despite imperfect matches between the gRNA sequence and the genomic DNA target sequence. Single mismatches of the gRNA can be permissive for off-target cleavage by Cas9. Off-target effects were reported for all the following cases: (a) same length but with 1-5 base mismatches; (b) off-target site in target genomic DNA has one or more bases missing ('deletions'); (c) off-target site in target genomic DNA has one or more extra bases ('insertions').

The term of "guide RNA" (gRNA) refers to the RNA component of a CRISPR-Cas system, e.g. crRNA, dual guide RNAs, a synthetic fusion of crRNA and tracrRNA via a tetraloop (GAAA) (defined as sgRNA) or other chemical linkers such as an nNt-Linker (defined as lgRNA), which is used interchangeably with "chimeric RNA", "chimeric guide RNA", "single guide RNA" and "synthetic guide RNA". The gRNA of CRISPR-Cas9 contains secondary structures of the repeat:anti-repeat duplex, stem loops 1-3, and the linker between stem loops 1 and 2.

The term of "dual RNAs" or "dual guide RNAs" refers to a hybridized complex of the short CRISPR RNAs (crRNA) and the trans-activating crRNA (tracrRNA). The crRNA hybridizes with the tracrRNA to form a crRNA:tracrRNA duplex, which is loaded onto a Cas protein to direct the cleavage of cognate DNA sequences bearing appropriate protospacer-adjacent motifs (PAM).

The term of "lgRNA" refers to a guide RNA (gRNA) joined by chemical ligations to form non-nucleotide linkers (nNt-linkers) between a crgRNA and a tracrgRNA, or at other sites.

The terms of "dual lgRNA", "triple lgRNA" and "multiple lgRNA" refer to hybridized complexes of the synthetic guide RNA fused by chemical ligations via non-nucleotide linkers. A dual tracrgRNA is formed by chemical ligation between a tracrgRNA1 and a tracrgRNA2 (RNA segments of ~30 nt), and a crgRNA (~30 nt) is fused with a dual tracrgRNA to form a triple lgRNA duplex, which is loaded onto Cas9 to direct the cleavage of cognate DNA sequences bearing appropriate protospacer-adjacent motifs (PAM). Each RNA segment can be readily accessible by chemical manufacturing and compatible to extensive chemical modifications.

The term "guide sequence" refers to the about 20 bp sequence within the guide RNA that specifies the target site and is herein used interchangeably with the terms "guide" or "spacer". The term "tracr mate sequence" may also be used interchangeably with the term "direct repeat(s)".

The term of "crgRNA" refers to a crRNA equipped with chemical functions for conjugation/ligation. The oligonucleotide may be chemically modified close to its 3'-end, any one or several nucleotides, or for its full sequence. A crgRNA may also be prepared by in vitro transcription at the presence of a RNA polymerase such as bacteriophage T7 RNA polymerase, and the conjugating chemical function, e.g., amine and alkyne, is incorporated at its 5'-end (preferably as 5'-GU . . . or 5'-GC . . . ), and 3'-end from a nucleoside triphosphate analogue, e.g. CTP and UTP:

U-1

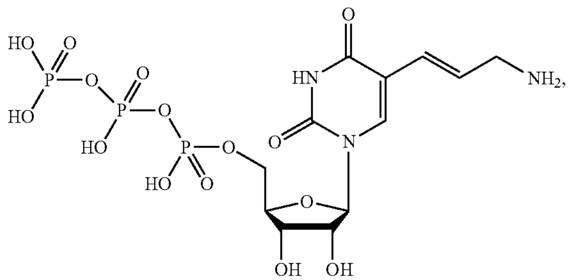

U-2

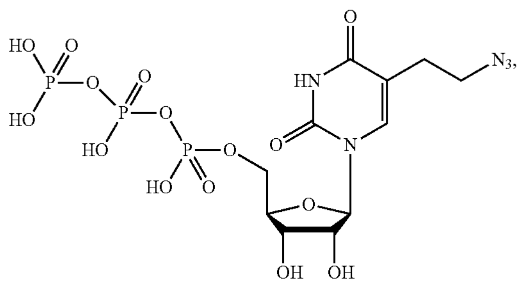

U-3

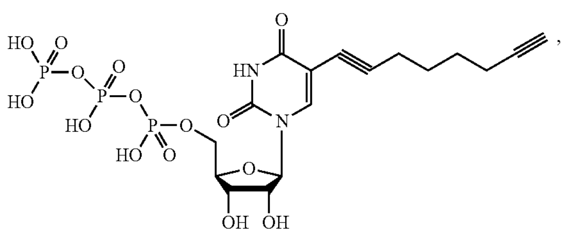

C-1

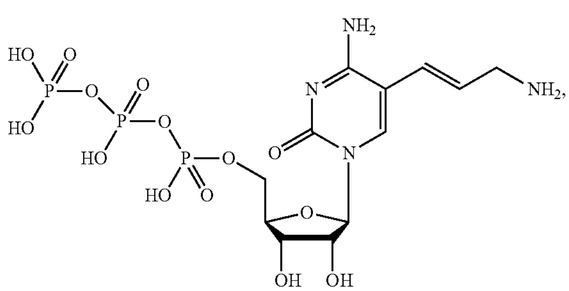

C-2

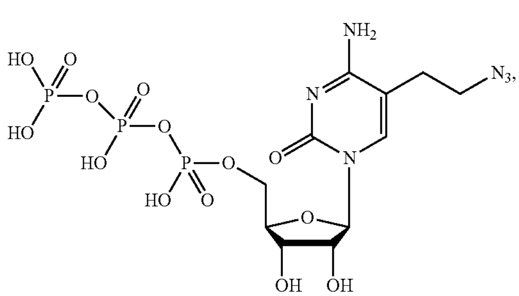

-continued

C-3

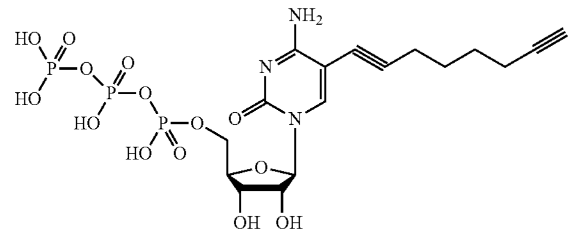

and etc.

The term of "tracrgRNA" refers to a tracrRNA equipped with chemical functions for conjugation/ligation. The oligonucleotide may be chemically modified at any one or several nucleotides, or for its full sequence by chemical synthesis. A tracrgRNA may also be prepared by in vitro transcription at the presence of a RNA polymerase such as bacteriophage T7 RNA polymerase, and the conjugating chemical function, e.g., amine and alkyne, is incorporated at its 5'-end (preferably as 5'-GU . . . or 5'-GC . . . ), and 3'-end from a nucleoside triphosphate analogue, e.g. CTP and UTP.

The term of "the protospacer adjacent motif (PAM)" refers to a DNA sequence immediately following the DNA sequence targeted by Cas9 in the CRISPR bacterial adaptive immune system, including NGG, NNNNGATT, NNAGAA, NAAAC, and others from different bacterial species where N is any nucleotide. In CRISPR-Cas12a system, "PAM" refers to a DNA sequence such as TTTN immediately before the targeted DNA sequence.

The term of "chemical ligation" refers to joining together synthetic oligonucleotides via an nNt-linker by chemical methods such as click ligation (the azide-alkyne reaction to produce a triazole linkage), thiol-maleimide reaction, and formations of other chemical groups.

The term of "complementary" refers to the ability of a nucleic acid to form hydrogen bond(s) with another nucleic acid sequence by either traditional Watson-Crick or other non-traditional types. Cas9 contains two nuclease domains, HNH and RuvC, which cleave the DNA strands that are complementary and non-complementary to the 20 nucleotide (nt) guide sequence in crRNAs, respectively.

The term of "a donor template" refers to a transgene cassette or a gene-editing-sequence flanked with homologous regions to recombine with the host loci and replace the mutated DNA with the correct sequence by HDR/SSTR. A donor template can be an ssDNA or a dsDNA or a plasmid/vector, and may be chemically conjugated to guide RNA(s) or Cas protein via a covalent linker.

A donor template can be chemically synthesized and equipped with chemical functions for conjugations/ligations. A conjugating donor template may also be prepared by in vitro gene synthesis at the presence of a DNA polymerase, with chemical functions, e.g. an amine and an alkyne, enzymatically incorporated at its 5' or 3'-end for chemical conjugation/ligation from a nucleoside triphosphate analogue.

The term of "gene editing sequence", "gene-editing-sequence" or "gene_editing_sequence" refers to the sequence contained in a donor template sequence to introduce expected gene editing, between the two homology arms identical to the DNA fragments flanking the cleavage site.

The term of "Hybridization" refers to a reaction in which one or more polynucleotides form a complex that is stabilized via hydrogen bonding between the bases of the nucleotide residues. The complex may comprise two strands forming a duplex structure, three or more strands forming a multi stranded complex, a single self-hybridizing strand, or any combination of these. A sequence capable of hybridizing with a given sequence is referred to as the "complement" of the given sequence.

The synonymous terms "hydroxyl protecting group" and "alcohol-protecting group" as used herein refer to substituents attached to the oxygen of an alcohol group commonly employed to block or protect the alcohol functionality while reacting other functional groups on the compound. Examples of such alcohol-protecting groups include but are not limited to the 2-tetrahydropyranyl group, 2-(bisacetoxyethoxy)methyl group, trityl group, trichloroacetyl group, carbonate-type blocking groups such as benzyloxycarbonyl, trialkylsilyl groups, examples of such being trimethylsilyl, tert-butyldimethylsilyl, tert-butyldiphenylsilyl, phenyldimethylsilyl, triiospropylsilyl and thexyldimethylsilyl, ester groups, examples of such being formyl, (C1-C10) alkanoyl optionally mono-, di- or tri-substituted with (C1-C6) alkyl, (C1-C6) alkoxy, halo, aryl, aryloxy or haloaryloxy, the aroyl group including optionally mono-, di- or tri-substituted on the ring carbons with halo, (C1-C6) alkyl, (C1-C6) alkoxy wherein aryl is phenyl, 2-furyl, carbonates, sulfonates, and ethers such as benzyl, p-methoxybenzyl, methoxymethyl, 2-ethoxyethyl group, etc. The choice of alcohol-protecting group employed is not critical so long as the derivatized alcohol group is stable to the conditions of subsequent reaction(s) on other positions of the compound of the formula and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and G. M. Wuts, T. W. Greene, "Protective Groups in Organic Synthesis", John Wiley & Sons Inc., Hoboken, New Jersey, 2007, which are hereby incorporated by reference. The related terms "protected hydroxyl" or "protected alcohol" define a hydroxyl group substituted with a hydroxyl protecting group as discussed above.

The term "nitrogen protecting group," as used herein, refers to groups known in the art that are readily introduced on to and removed from a nitrogen atom. Examples of nitrogen protecting groups include but are not limited to acetyl (Ac), trifluoroacetyl, Boc, Cbz, benzoyl (Bz), N,N-dimethylformamidine (DMF), trityl, and benzyl (Bn). See also G. M. Wuts, T. W. Greene, "Protective Groups in Organic Synthesis", John Wiley & Sons Inc., Hoboken, New Jersey, 2007, and related publications.

The term "conjugation", as used herein, refers to a method for covalently crosslinking drug molecules, proteins or nucleic acids to other molecules using crosslinking reagents. The product of conjugation is referred as "conjugate(s)". Traditional pharmaceuticals can be linked to monoclonal antibodies to deliver targeted doses, prevent breakdown, decrease immunogenicity, and increase bioavailability in circulation. CRISPR RNP complex can be chemically modified by linking to other molecules either covalently or non-covalently.

The term "conjugating site", as used herein, refers to a chemical moiety which is directly linked to other molecules by conjugation, and a conjugating site can be an amino acid residue, N-terminus or C-terminus of proteins, a nucleoside, a nucleotide, or a phosphate.

The term "PEG," or "macrogol", as used herein, refers to polyethylene glycol chains, linear, branched, substituted or unsubstituted. A derivatized linear single PEG chain comprises at least 2 PEG subunits.

The term "PEGylation", as used herein, refers to the process of both covalent and non-covalent attachment or amalgamation of polyethylene glycol (PEG) polymer chains to molecules and macrostructures, such as a drug, a CRISPR RNP complex, a therapeutic protein or vesicle, which is then described as PEGylated. PEGylation is routinely achieved by incubation of a reactive derivative of PEG with the target molecule.

The term "glycan", as used herein, refers to polysaccharides or the carbohydrate portion of a glycoconjugate, such as a glycoprotein, glycolipid, or a proteoglycan, even if the carbohydrate is only an oligosaccharide.

The term "polysaccharides", as used herein, refers compounds consisting of a large number of monosaccharides linked glycosidically.

The term "epitope" or "antigenic determinant", as used herein, refers to the part of an antigen that is recognized by the immune system, specifically by antibodies, B cells, or T cells. An epitope can be either conformational or linear.

The term "epitope masking", as used herein, refers to identifying potentially immunogenic peptide sequences and modifying or removing them to prevent detection by the immune system while still maintaining the therapeutic function of the original protein.

The term of "Isotopically enriched" refers to a compound containing at least one atom having an isotopic composition other than the natural isotopic composition of that atom. The term of "Isotopic composition" refers to the amount of each isotope present for a given atom, and "natural isotopic composition" refers to the naturally occurring isotopic composition or abundance for a given atom. As used herein, an isotopically enriched compound optionally contains deuterium, carbon-13, nitrogen-15, and/or oxygen-18 at amounts other than their natural isotopic compositions. Conjugates of CRISPR RNP complexes are optionally isotopically enriched at selected positions to optimize their drug properties based on isotope effects.

As used herein, the terms "therapeutic agent" and "therapeutic agents" refer to any agent(s) which can be used in the treatment or prevention of a disorder or one or more symptoms thereof and are herein used interchangeably with "Pharmaceutical agents". In certain embodiments, the term "therapeutic agent" includes a compound provided herein. In certain embodiments, a therapeutic agent is an agent known to be useful for, or which has been or is currently being used for the treatment or prevention of a disorder or one or more symptoms thereof.

The term of "gene therapy" refers to altering a disease-causing gene in a patient or introducing a healthy copy of a mutated gene to a patient to treat genetic diseases. CRISPR/Cas can potentially be used to introduce site specific gene editing to correct disease-causing mutations, or to deliver a correct gene into human genome to fix a defect gene or a desired gene. CRISPR/Cas can potentially be used to remove and/or deactivate episomal HBV cccDNA and integrated viral genomes such as HIV proviral DNA and integrated HBV DNA to cure these infectious diseases.

It is noted that as used, the singular forms "a," "an," and "the" include plural referents unless the context clearly dictates otherwise. Thus, for example, reference to "a guide RNA(s)-Cas protein (RNP) complex" includes a plurality of such complexes. Reference to "the conjugate" includes reference to one or more conjugates and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Nucleotides

In some embodiments, the crRNA and tracrRNA are truncated at 3'-end and 5'-end, respectively:

(SEQ ID NO: 1 (top) and NO: 2 (bottom))

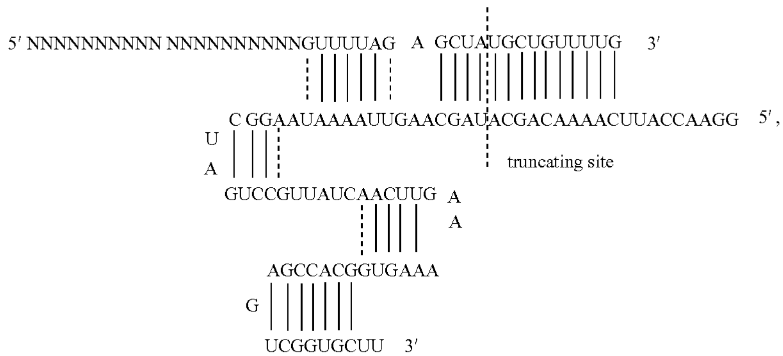

and the duplex ends are rejoined by a small molecule non-nucleotide linker (nNt-linker, ligation1) to form a dual lgRNA:

(SEQ ID NO: 3)

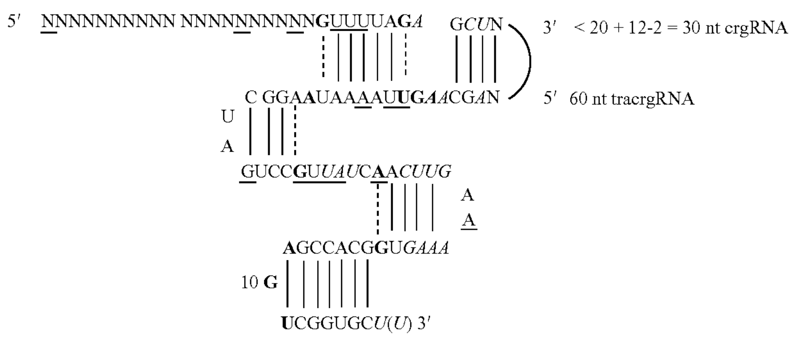

wherein "NNNNNNNNNN NNNNNNNNNN" is a guide sequence of 17-20 nt, and N is preferably a ribonucleotide with intact 2'-OH, and wherein ")" is a chemical nNt-linker.

In some embodiments, the duplex ends are rejoined by a tetraloop (e.g. GAAA) to form an sgRNA:

(SEQ ID NO: 4)

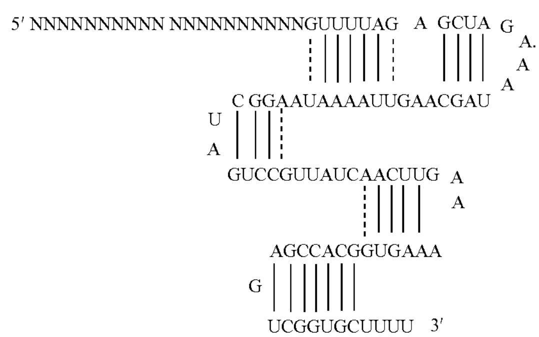

In other embodiments, tracrRNA is a ligated dual oligonucleotide (via ligation2, the inner ligation between tracrgRNA1 and tracrgRNA2), or a multiple oligonucleotide. Non-limiting examples include:

(SEQ ID NO: 5)

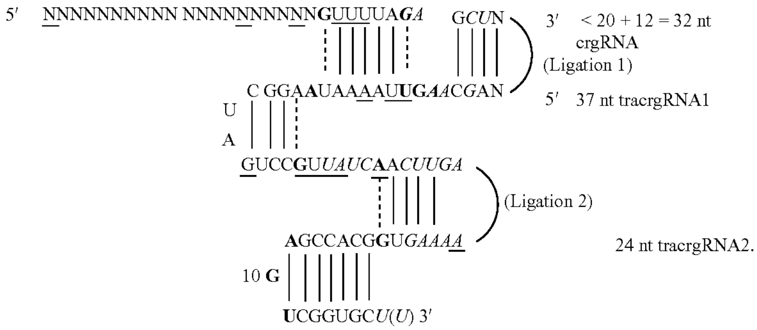

In some embodiments, the crRNA and tracrRNA are further truncated and the ligation site can be located at other positions, as illustrated by non-limiting examples of resulting lgRNAs in U.S. Pat. No. 10,059,940.

In some embodiments, crRNA and tracrRNA are truncated at 3'-end and 5'-end, respectively, and the duplex ends are rejoined by a nucleotide linker such as an aptamer and thus to provide an extended single gRNA with small molecule and protein recognition module(s):

(SEQ ID NO: 6)

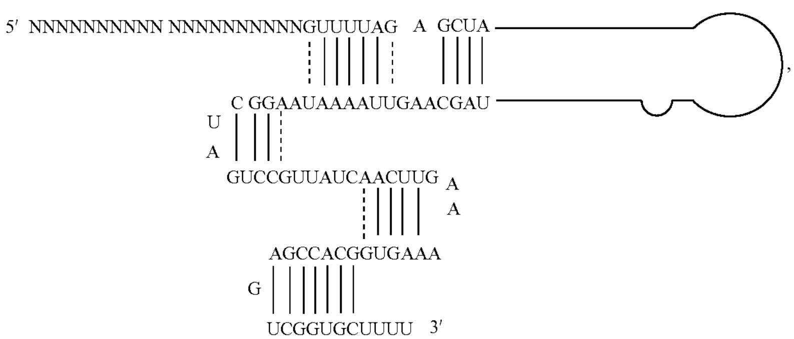

(SEQ ID NO: 7)

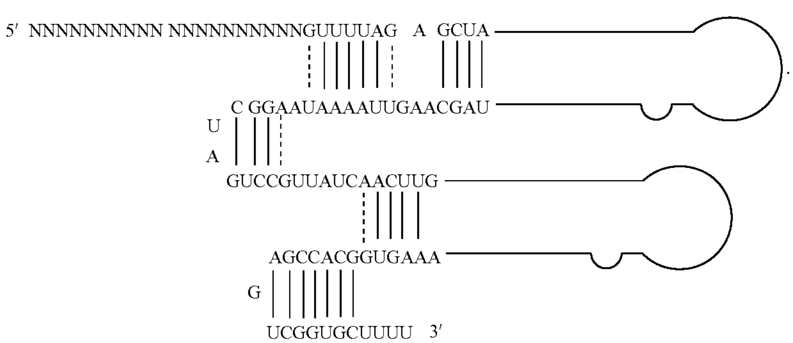

In another embodiment, the crRNA and tracrRNA are truncated at 3'-end and 5'-end, respectively, and the duplex ends are rejoined by a non-nucleotide linker-aptamer conjugate to provide an extended single lgRNA with small molecule and protein recognition module(s):

(SEQ ID NO: 8)

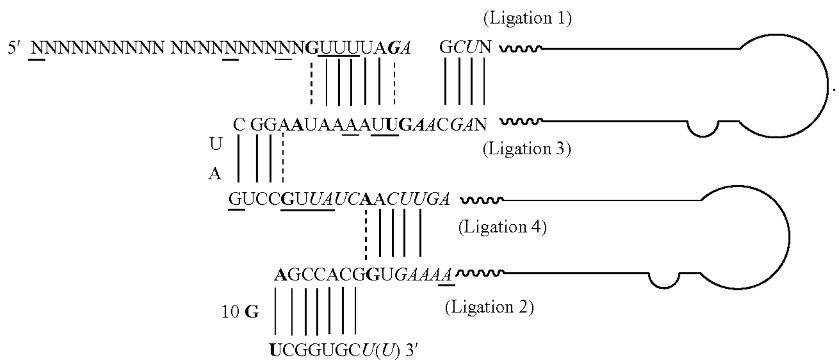

In another embodiment, the stem loop of tracrRNA is split at the GAAA tetraloop, and the duplex ends are rejoined by a non-nucleotide linker-aptamer conjugate to provide an extended tracrRNA with small molecule and protein recognition module(s):

(SEQ ID NO: 9)

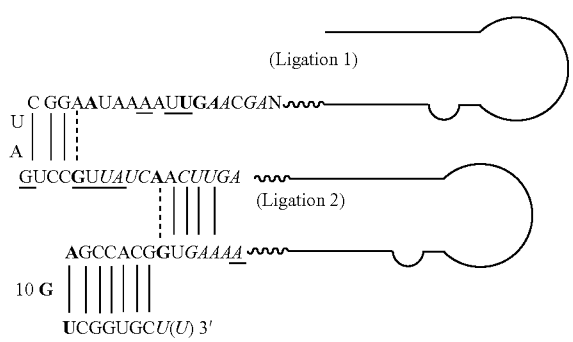

In yet another embodiment, lgRNA is conjugated with an aptamer by a non-nucleotide linker at either of the two GAAA tetraloops or both, or 5'/3'-end of sgRNA, to bind a small molecule or a biopolymer such as a protein or a nucleic acid:

(SEQ ID NO: 10)

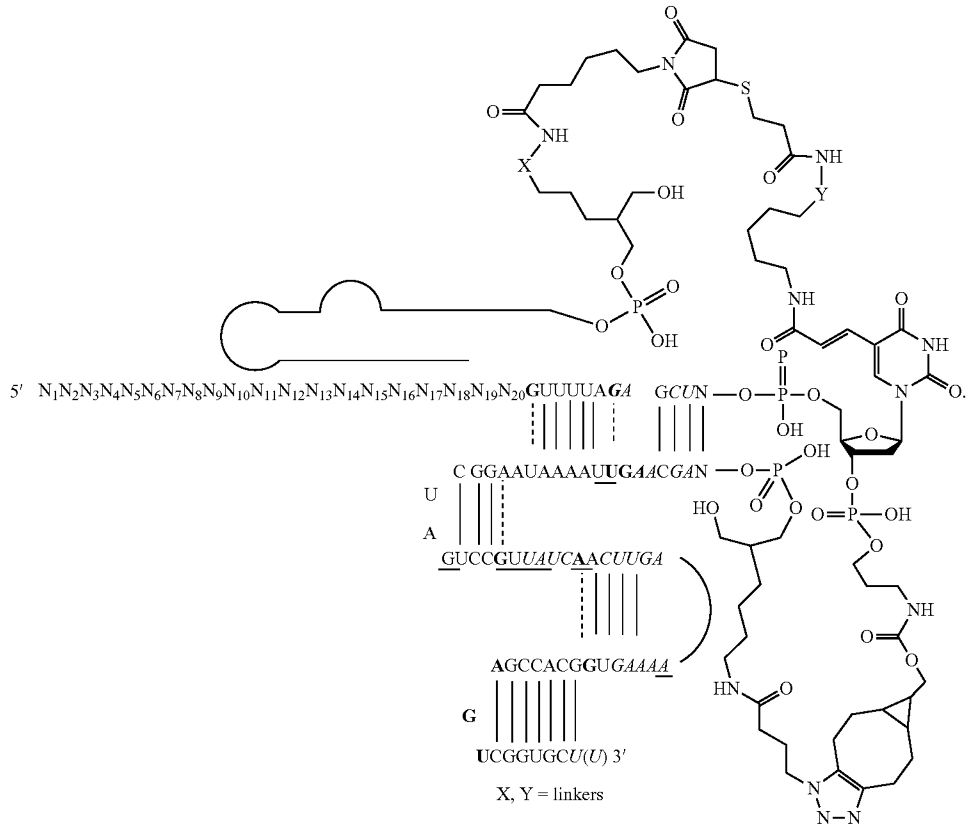

X, Y = linkers

In some embodiments, the crRNA and tracrRNA are shortened by truncation at 3'-end and 5'-end, respectively, and the repeat/anti-repeat duplex comprises a bulge and >12 Watson-Crick base pairs:

(SEQ ID NO: 11)

```
5' NNNNNNNNNN NNNNNNNNNNGUUUUAG  A  GCUAUGCU... 3'
                       ¦||||||¦     ||||||||
                 C GGAAUAAAAUUGAACGAUACGA... 5'.
               U ||||¦
               A ||||¦
```

-continued (SEQ ID NO: 12)

```
GUCCGUUAUCAACUUG A
           ¦||||  A
      AGCCACGGUGAAA
    G |||||||
      UCGGUGCUUUU  3'
```

In some embodiments, the crRNA and tracrRNA are joined at 3'-end of tracrRNA and 5'-end of crRNA by a nucleotide linker or a non-nucleotide linker to form a sgRNA or lgRNA, respectively; and the tracrRNA is optionally a ligated tracrRNA comprising one or more than one non-nucleotide linker:

(SEQ ID NO: 13)
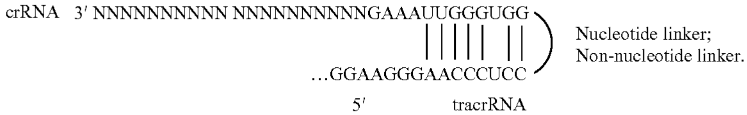
In some embodiments, the dual guide RNAs, sgRNA and lgRNA are conjugates of small molecule ligands, antibodies or aptamers:
(SEQ ID NO: 14)
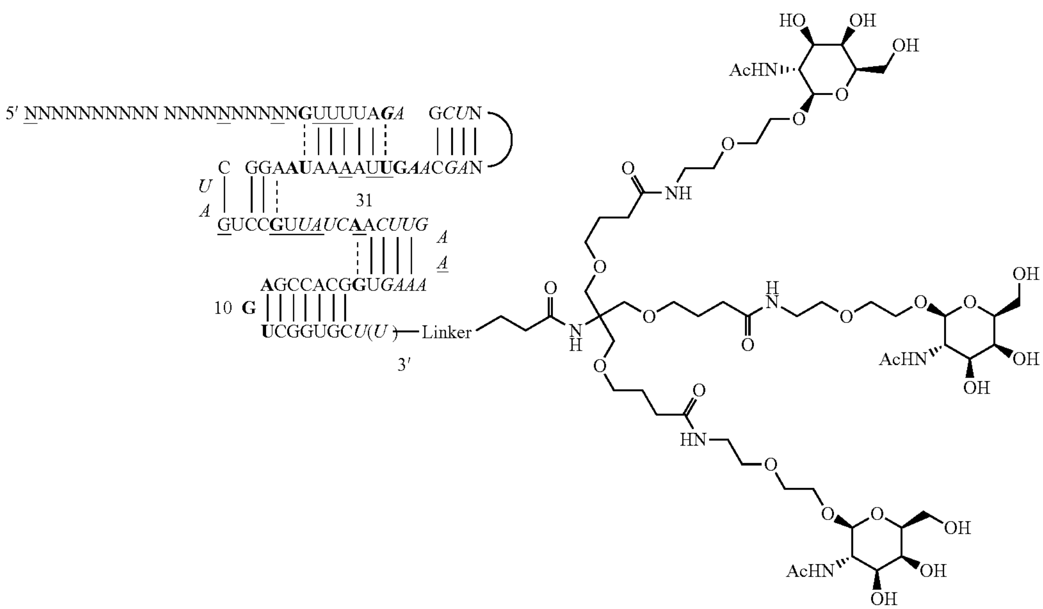
(SEQ ID NO: 15)
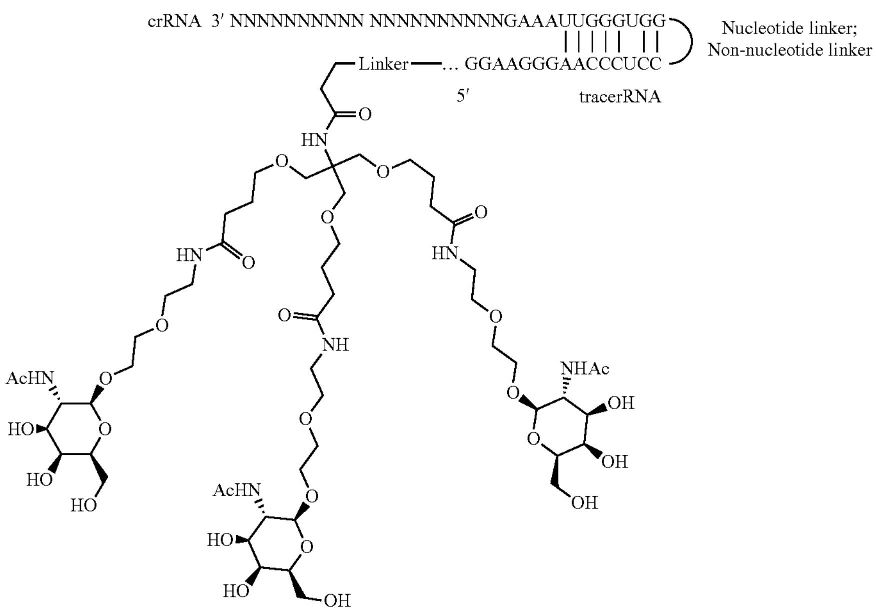

-continued
(SEQ ID NO: 17)
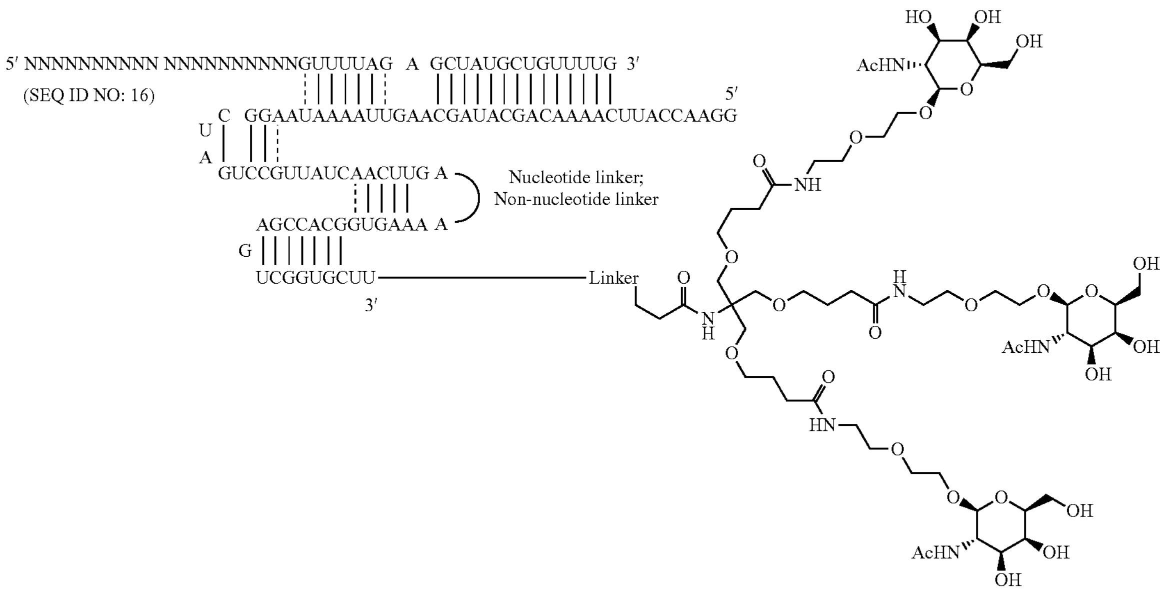
(SEQ ID NO: 18)
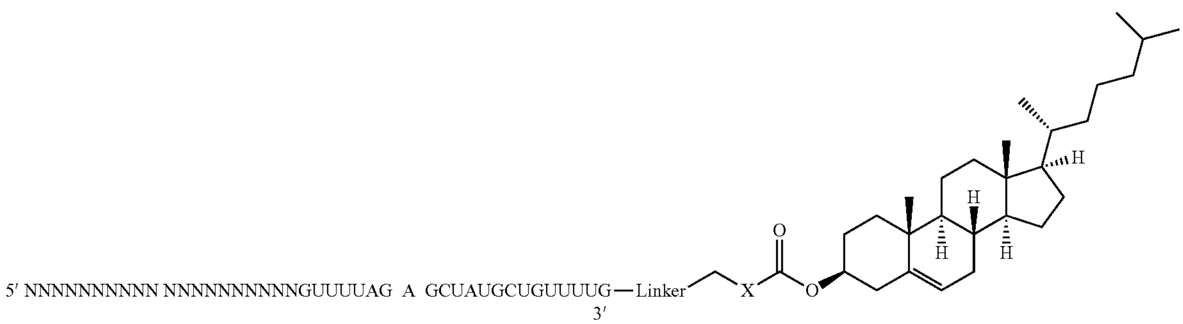
$X = CH_2, NH$
(SEQ ID NO: 19)
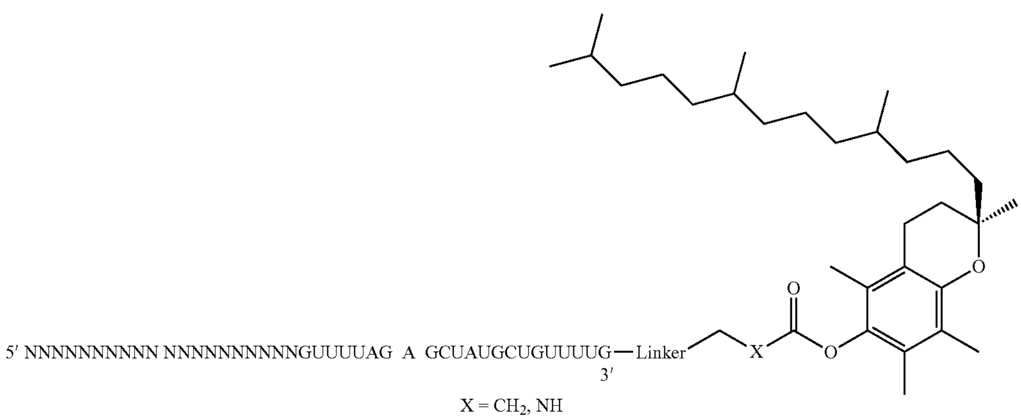
$X = CH_2, NH$
(SEQ ID NO: 20)
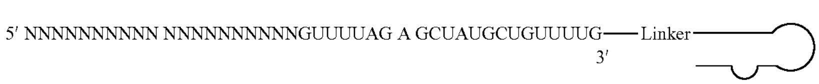
(SEQ ID NO: 21)
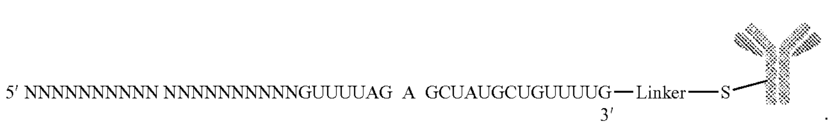

In some embodiments, the crRNA, dual guide RNAs, sgRNA and lgRNA are conjugated with single-stranded template repair (SSTR) donor DNA templates of sequences containing a 5'-homology arm and a downstream gene editing sequence, optionally followed by a 3'-homology arm. Non-limiting such examples are given below:
(SEQ ID NO: 22)
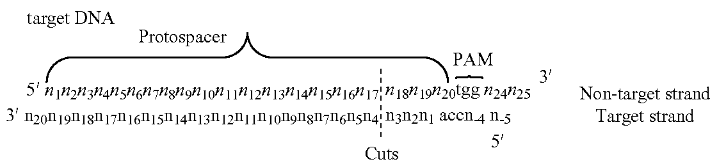
(SEQ ID NO: 23)
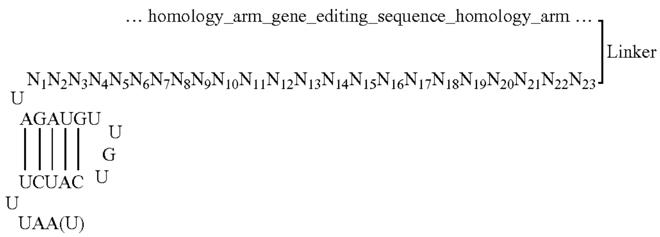
(SEQ ID NO: 24)
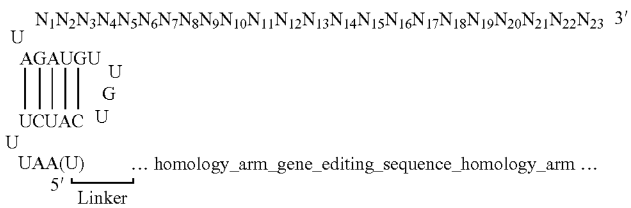
(SEQ ID NO: 25)
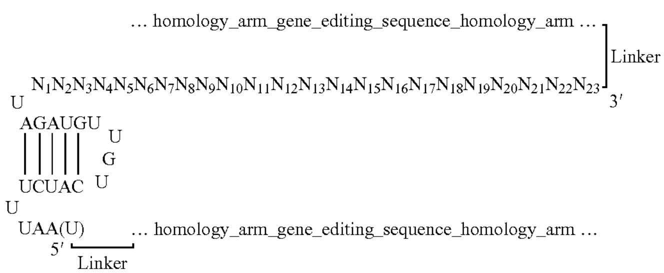
(SEQ ID NO: 26)
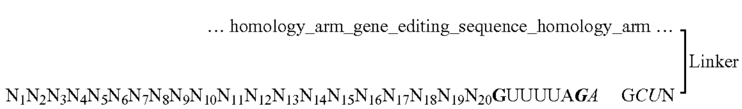
(SEQ ID NO: 27)
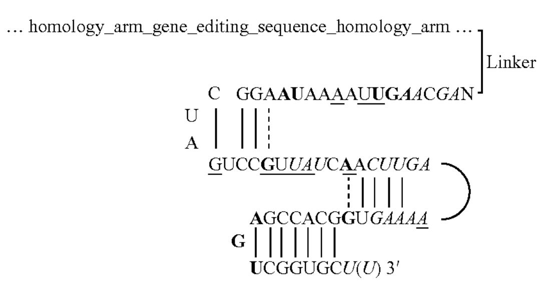

-continued
(SEQ ID NO: 28)
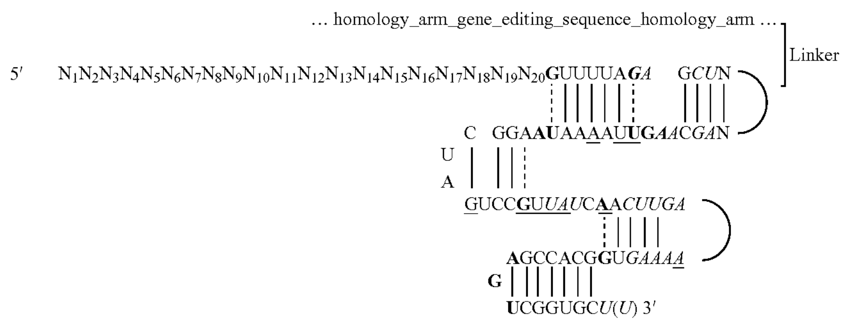
(SEQ ID NO: 29)
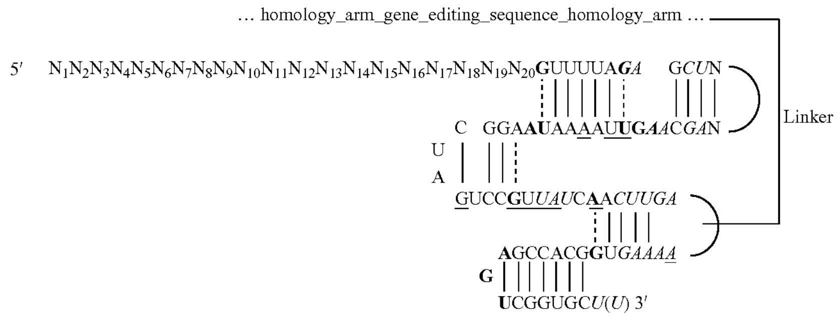
(SEQ ID NO: 30)
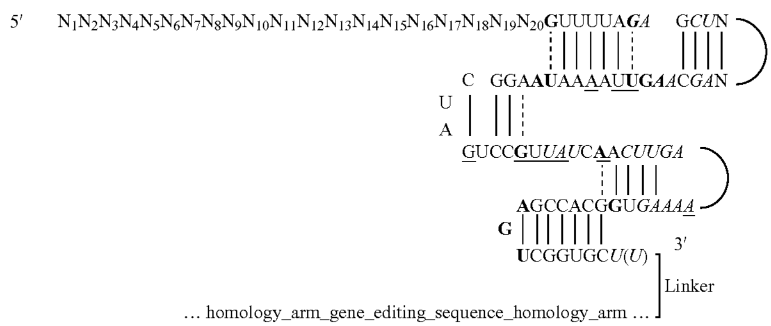
(SEQ ID NO: 31)
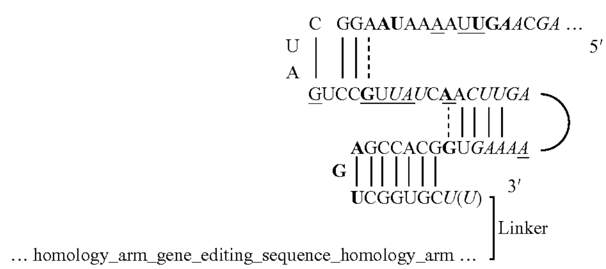
(SEQ ID NO: 32)
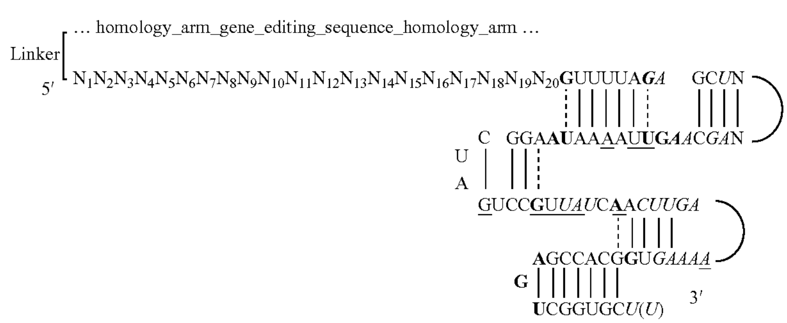

-continued (SEQ ID NO: 33)

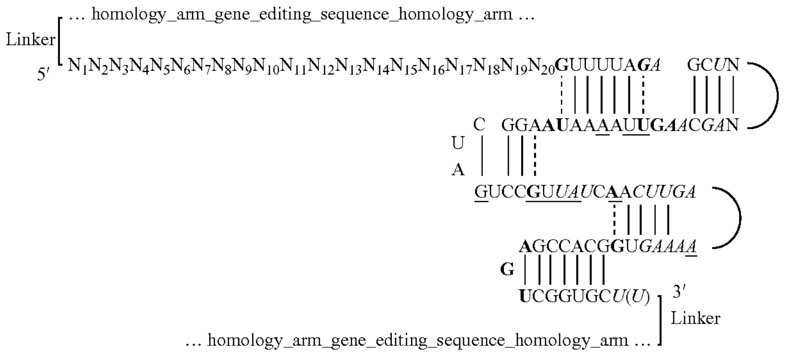

In certain embodiments, the conjugating linker (], Linker) is an oligonucleotide.

In certain embodiments, the conjugating linker is an RNA tetraloop such as ANYA, CUYG, GNRA, UNAC and UNCG, wherein N could be uracil, adenine, cytosine, or guanine, R is either guanine or adenine and Y is either uracil or cytosine.

In certain embodiments, the conjugating linker is an nNt-linker, as described in U.S. Pat. No. 10,059,940, selected from a group comprising a 1,4-disubstituted 1,2,3-triazole formed between an alkyne and an azide via [3+2] cycloaddition catalyzed by Cu(I) or without Cu(I) catalysis (such as strain-promoted azide-alkyne cycloaddition (SPAAC)), a thioether by chemical ligation between a thiol and a maleimide, and other functional groups.

In certain embodiments, homology arms flanking the gene editing sequence overlap with the non-target PAM containing strand of target DNA.

In certain embodiments, homology arms flanking the gene editing sequence overlap with the target strand of target DNA.

In some embodiments, the conjugating site is the 5-position of the nucleoside base U or C, or the 7-position of the nucleoside base 7-deazaguanine or 7-deazaadenine, or the 8-position of the nucleoside base purine.

In other embodiments, the conjugating site is the 2'- or 5'-position of the sugar moiety of the 5'-end nucleotide of crRNA, tracrRNA, a single strand HDR/SSTR donor template (ssDNA), sgRNA or lgRNA.

In other embodiments, the conjugating site is the 2'- or 3'-position of the sugar moiety of the 3'-end nucleotide of crRNA, tracrRNA, a single strand HDR/SSTR donor template (ssDNA), sgRNA or lgRNA.

In certain embodiments, as non-limiting examples, the lgRNA-ssDNA conjugates comprise the following structures:

(SEQ ID NO: 34)

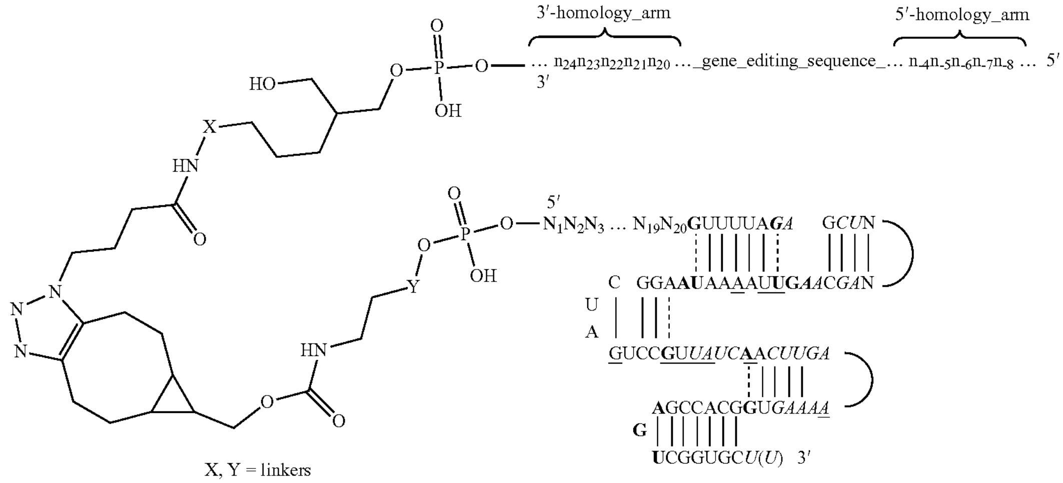

X, Y = linkers

-continued
(SEQ ID NO: 35)
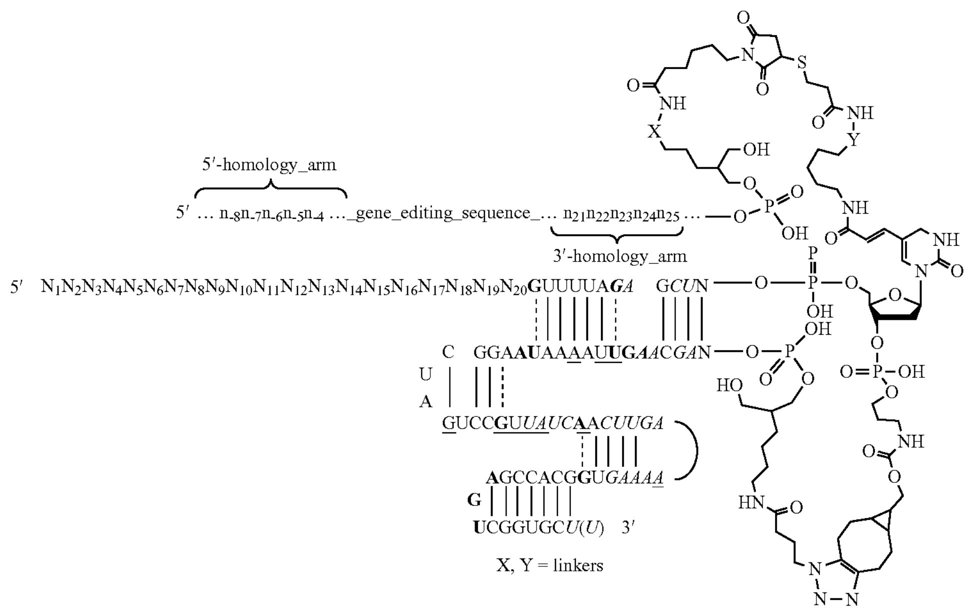
(SEQ ID NO: 36)
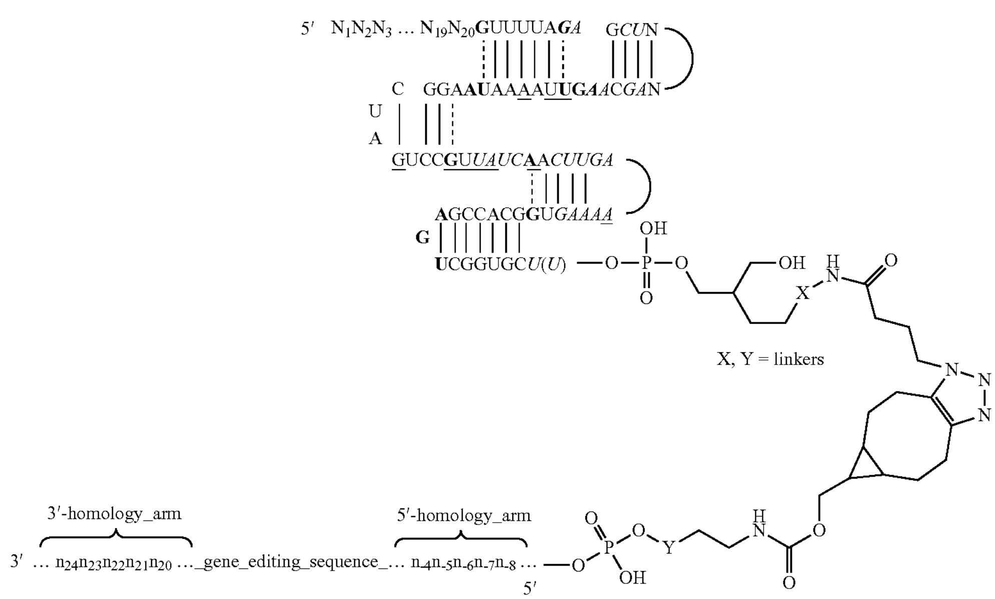

-continued
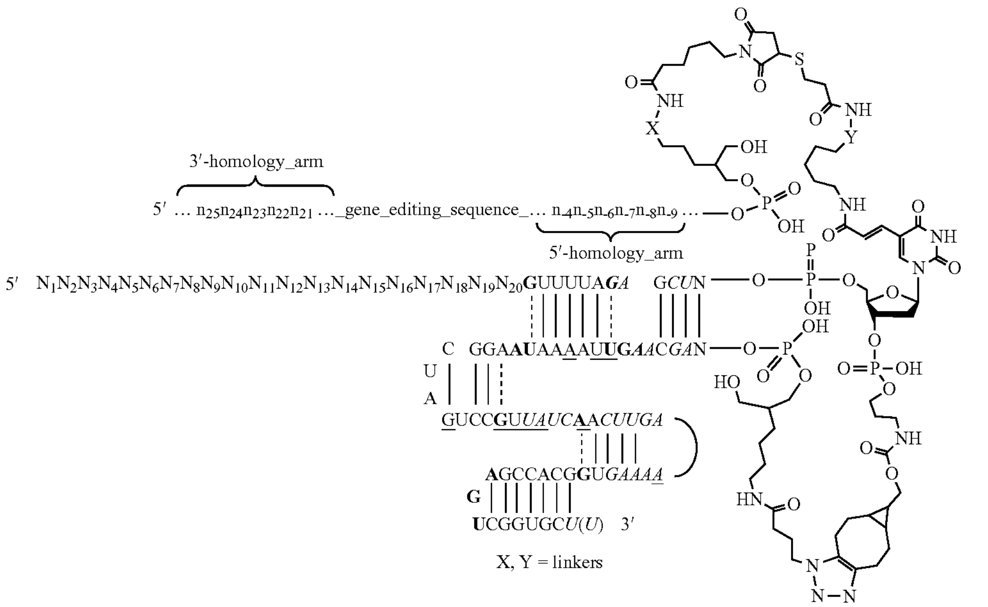
X, Y = linkers
(SEQ ID NO: 38)
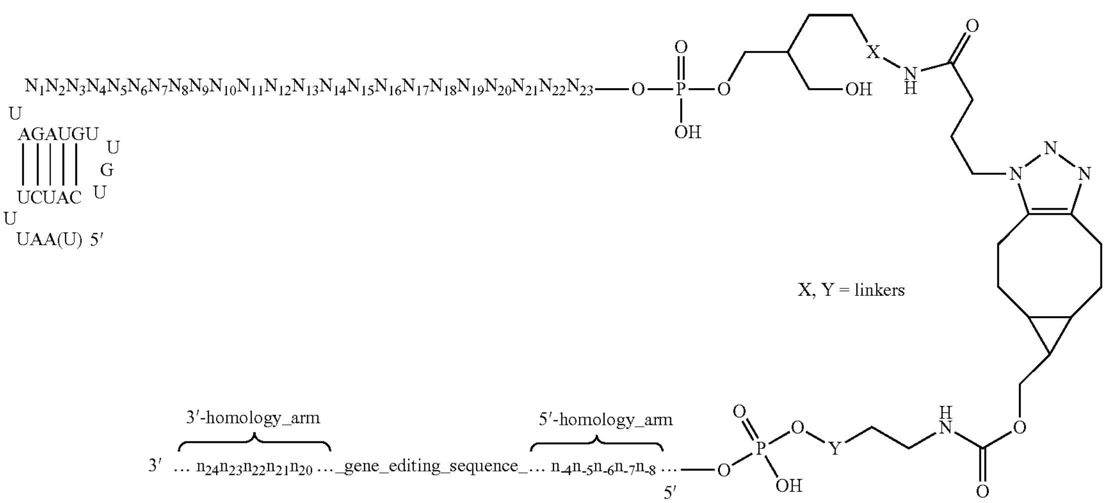
X, Y = linkers
(SEQ ID NO: 39)
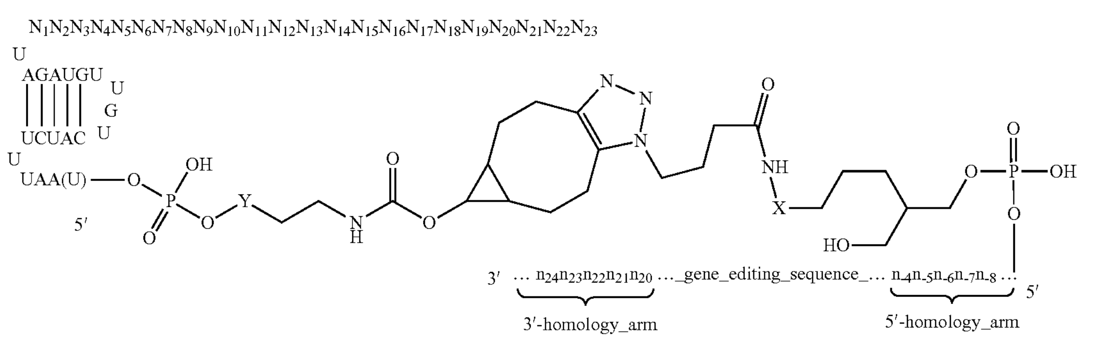
X, Y = linkers -continued
(SEQ ID NO: 40)
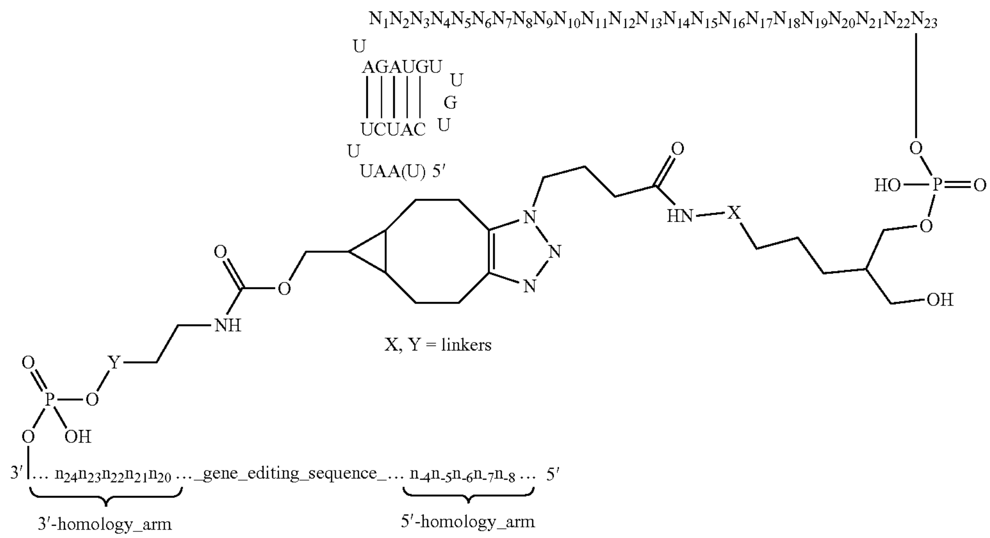
X, Y = linkers
(SEQ ID NO: 41)
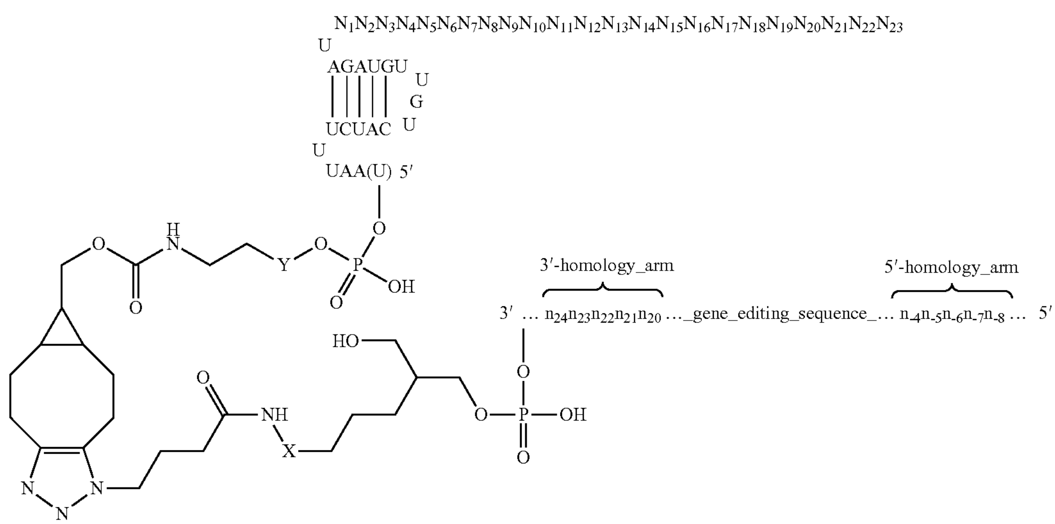
X, Y = linkers -continued (SEQ ID NO: 42)

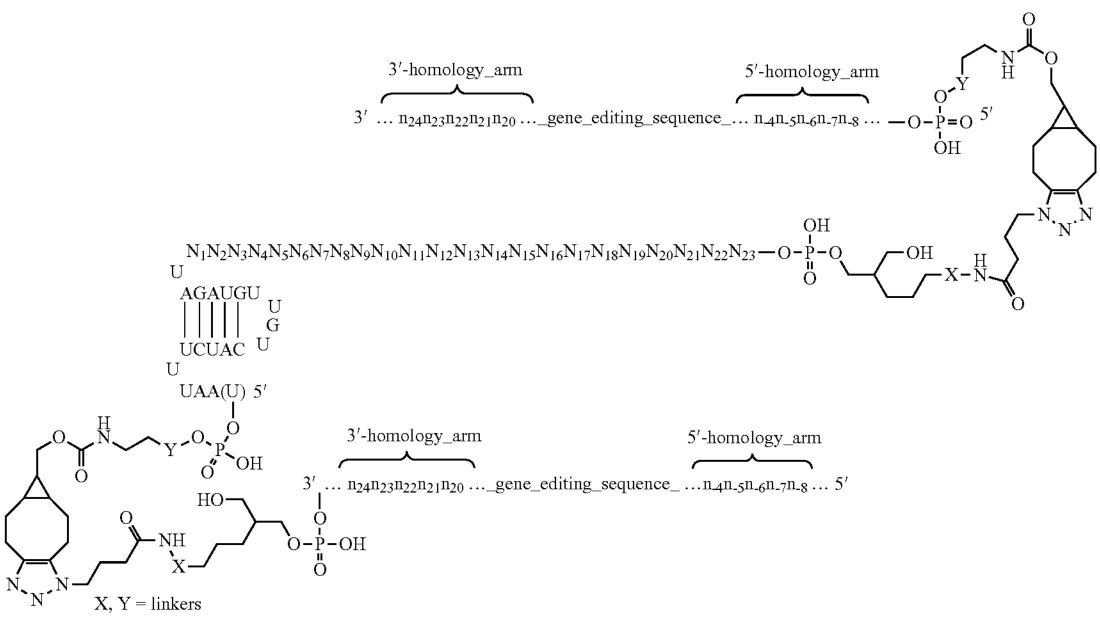

(SEQ ID NO: 43)

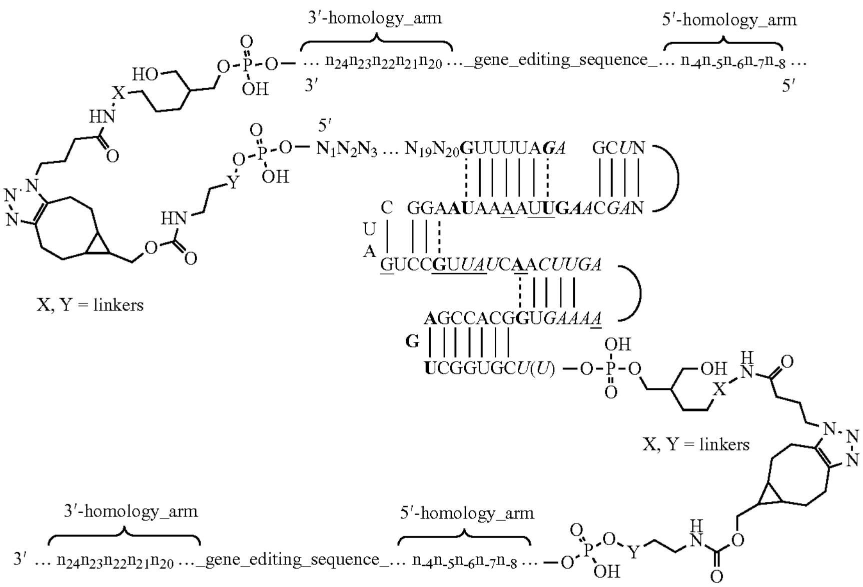

In some embodiments, the "gene-editing-sequence" comprises an oligonucleotide sequence to introduce insertion(s) of one or more stop codons selected from a group comprising 5'-(tga)-3', 5'-(taa)-3', 5'-(tag)-3', 5'-(tga-ntga-ntga)-3' (Sequence No 84), 5'-(tga-ntga-ntaa)-3' (Sequence No 85), 5'-(tga-ntga-ntag)-3' (Sequence No 86), 5'-(tga-ntaa-ntga)-3' (Sequence No 87), 5'-(tga-ntaa-ntaa)-3' (Sequence No 88), 5'-(tga-ntaa-ntag)-3' (Sequence No 89), 5'-(tga-ntga-ntga)-3' (Sequence No 90), 5'-(tga-ntga-ntaa)-3' (Sequence No 91), 5'-(tga-ntga-ntag)-3' (Sequence No 92), 5'-(taa-ntga-ntga)-3' (Sequence No 93), 5'-(taa-ntga-ntaa)-3' (Sequence No 94), 5'-(taa-ntga-ntag)-3' (Sequence No 95), 5'-(taa-ntaa-ntga)-3' (Sequence No 96), 5'-(taa-ntaa-ntaa)-3' (Sequence No 97), 5'-(taa-ntaa-ntag)-3' (Sequence No 98), 5'-(taa-ntga-ntga)-3' (Sequence No 99), 5'-(taa-ntga-ntaa)-3' (Sequence No 100), 5'-(taa-ntga-ntag)-3' (Sequence No 101), 5'-(tag-ntga-ntga)-3' (Sequence No 102), 5'-(tag-ntga-ntaa)-3' (Sequence No 103), 5'-(tag-ntga-ntag)-3' (Sequence No 104), 5'-(tag-ntaa-ntga)-3' (Sequence No 105), 5'-(tag-ntaa-ntaa)-3' (Sequence No 106), 5'-(tag-ntaa-ntag)-3' (Sequence No 107), 5'-(tag-ntga-ntga)-3' (Sequence No 108), 5'-(tag-ntga-ntaa)-3' (Sequence No 109) and 5'-(tag-ntga-ntag)-3' (Sequence No 110), wherein n is any nucleotide, and said more stop codons comprise repetitive said sequence separated by absent or more nucleotides in between or different said sequences separated by absent or more nucleotides in between.

In some embodiments, the "gene-editing-sequence" comprises one or more sequences such as stop codons to deactivate integrated and episomal viral DNAs, oncogenic or pathogenic gene loci in animals and human.

In some embodiments, the "gene-editing-sequence" comprises one or more sequences such as stop codons to deactivate target gene(s) and to eliminate undesirable effects of off-target edits.

In some embodiments, the "gene-editing-sequence" comprises DNA sequence(s) to correct oncogenic or pathogenic gene mutations in animals and human.

Figure 7:
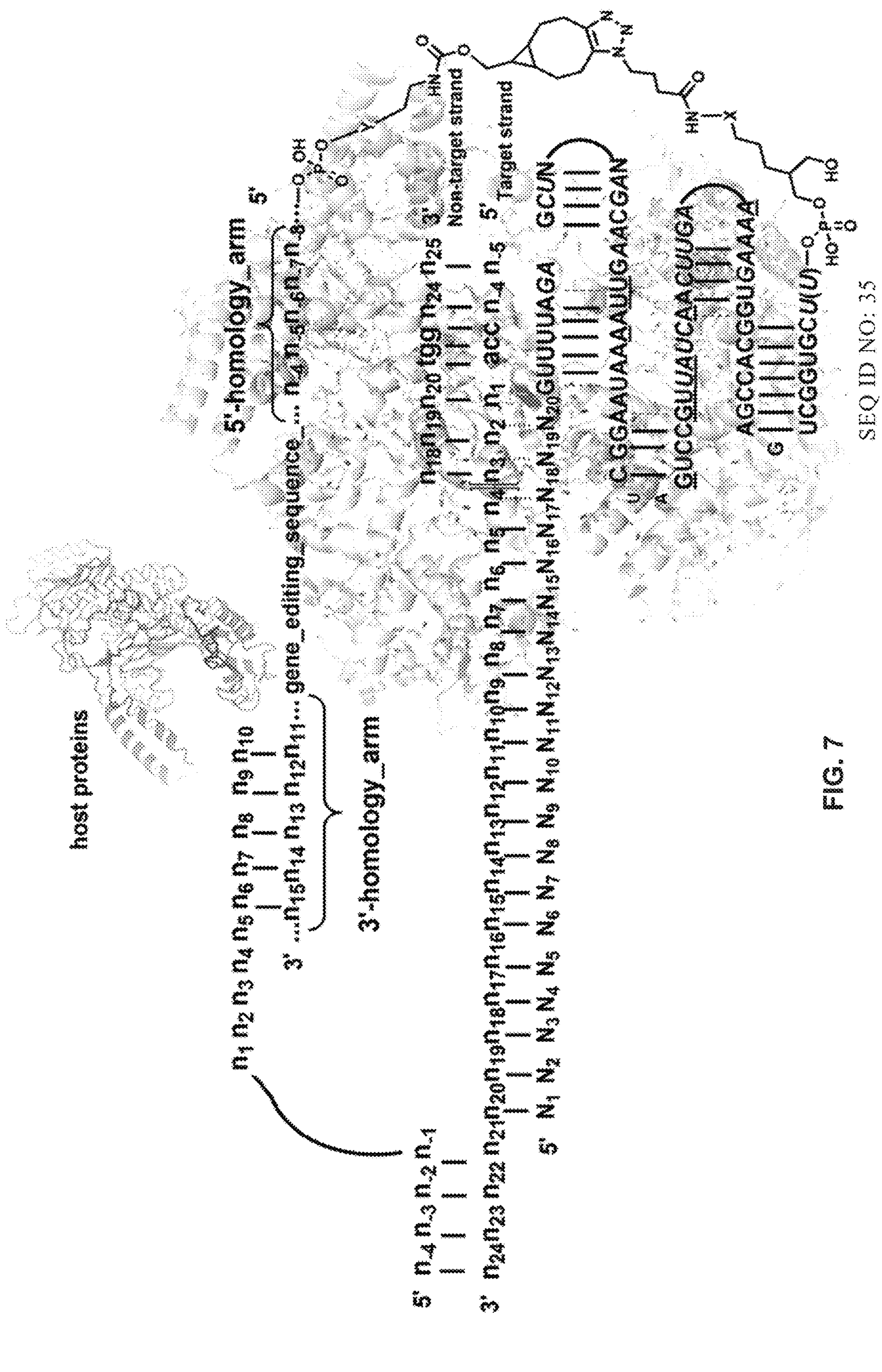
FIG. 7: Model of a Cas9/lgRNA-ssDNA in synchronizing actions with host enzymes. Host DNA polymerase extends the PAM distal strand of the R-loop asymmetrically released from a Cas9:lgRNA:DNA complex (SEQ ID NO: 35) after hybridization with a conjugated ssDNA and uses the ssDNA as the template.
Figure 8:
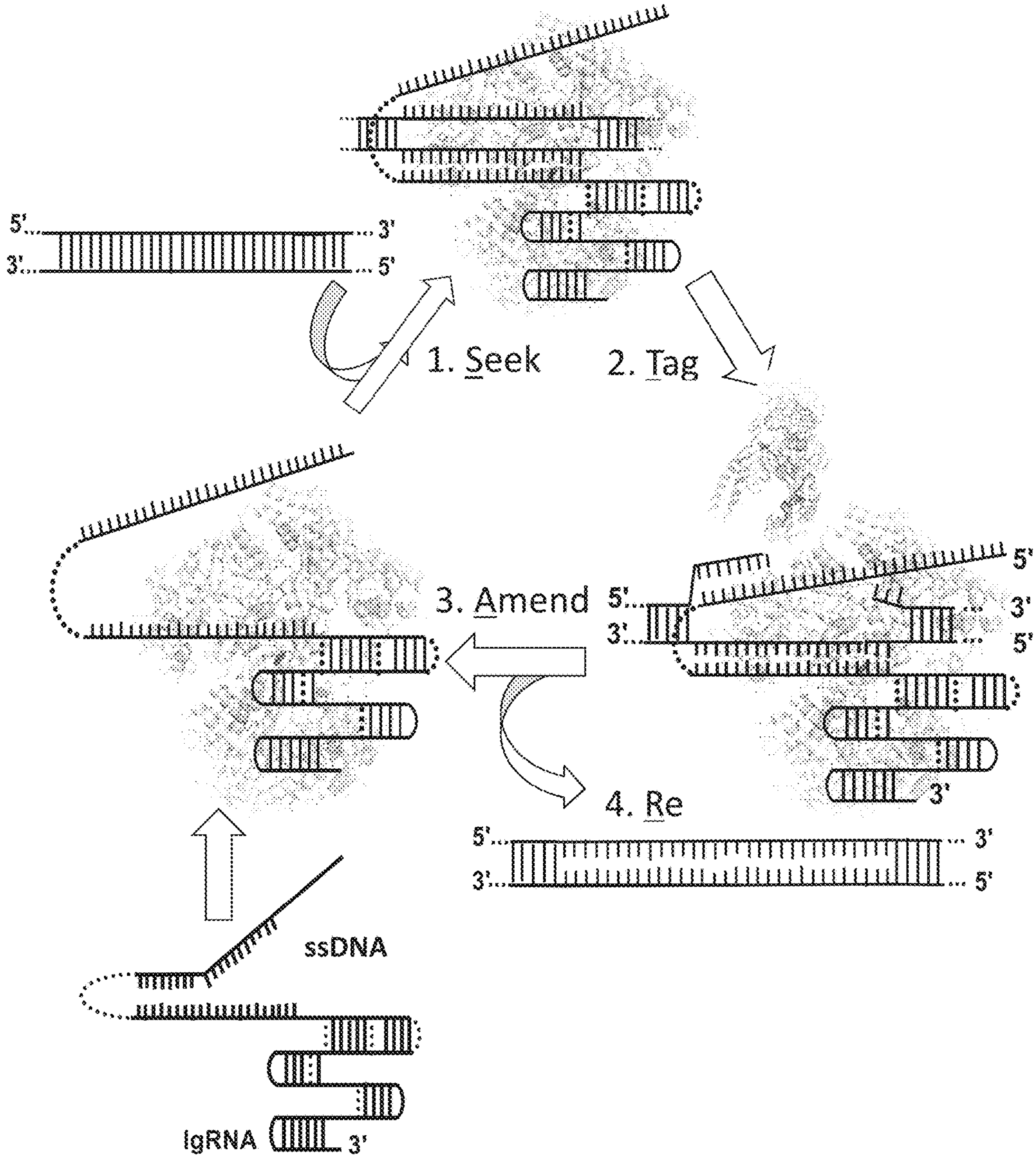
FIG. 8: Multiple-turnover STAR (Seek-Tag-Amend-Release) CRISPR-Cas9 for editing pathogenic genes with enhanced release of the acting RNP complex. 1. Seek: a Cas9/lgRNA-ssDNA complex binds a double-stranded DNA sequence that contains a sequence match to the 17-20 nucleotides of the lgRNA (spacer) and immediately before a protospacer adjacent motif (PAM) to form an R-loop. 2. Tag: HNH cleaves the target strand at the position 3 bases upstream of the PAM, while less precise cleavage and further 3'-end processing by RuvC leave shortened PAM distal strands of various lengths which are asymmetrically released from a Cas9:lgRNA-ssDNA:DNA complex. The released DNA strand acts as a primer and hybridizes with the 3'-homology arm of the conjugated ssDNA, which acts as a template for DNA repair. 3. Amend: the tagged double strand breaks are repaired and the flaps are removed and gaps are ligated by cellular enzymes. 4. Release: Cas9: lgRNA-ssDNA complex is released from the repaired DNA, and is ready for next cycle. The Cas9 protein can be a nickase, e.g. HNH (H840A), and a DNA nick is formed and repaired in a similar way (STAR) to release the dCas9: lgRNA-ssDNA.
Figure 9:
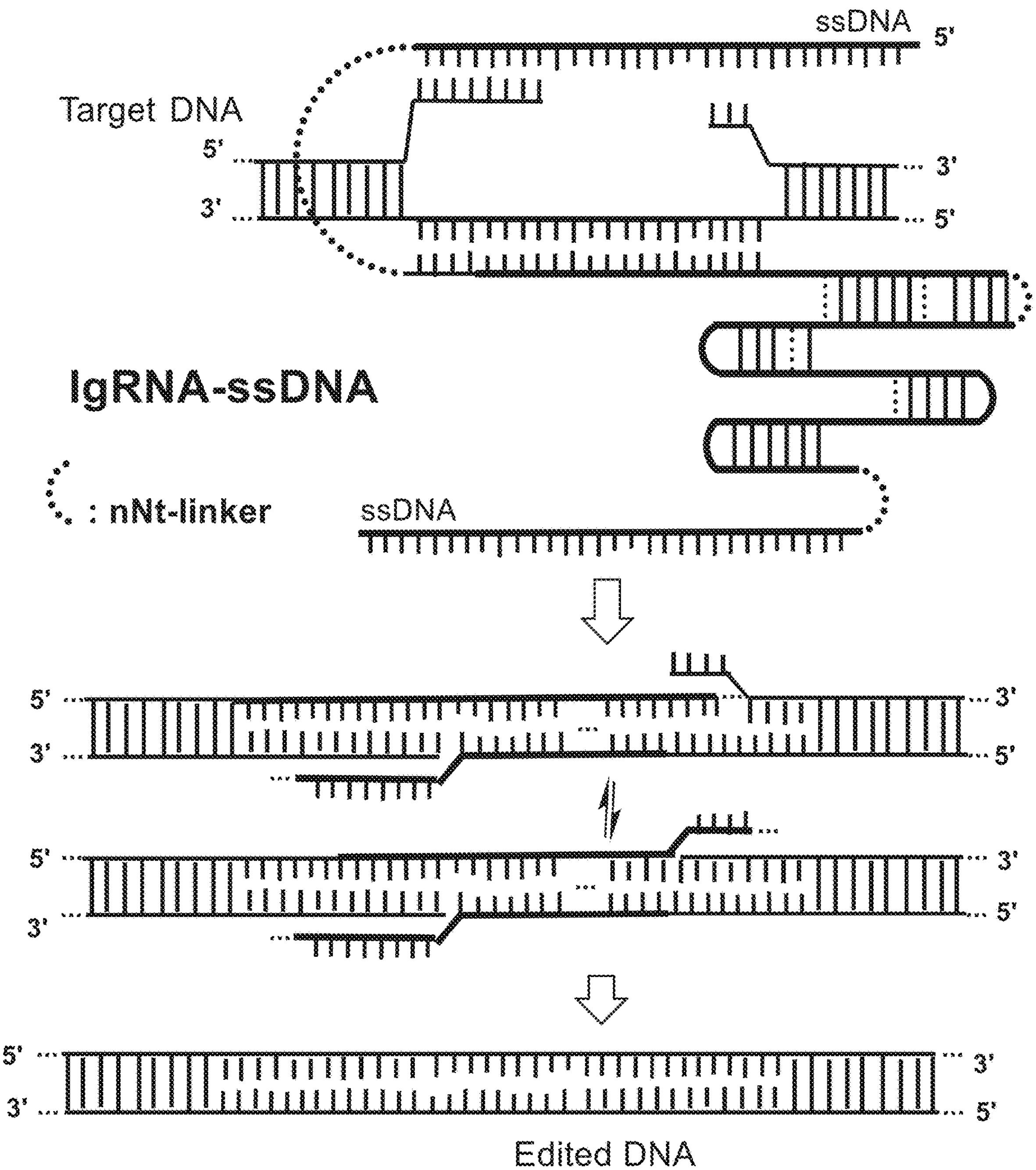
FIG. 9: DNA repair through microhomology-mediated end joining (MHEJ) pathway directed by lgRNA-ssDNA in Cas9-based gene editing.
Figure 10:
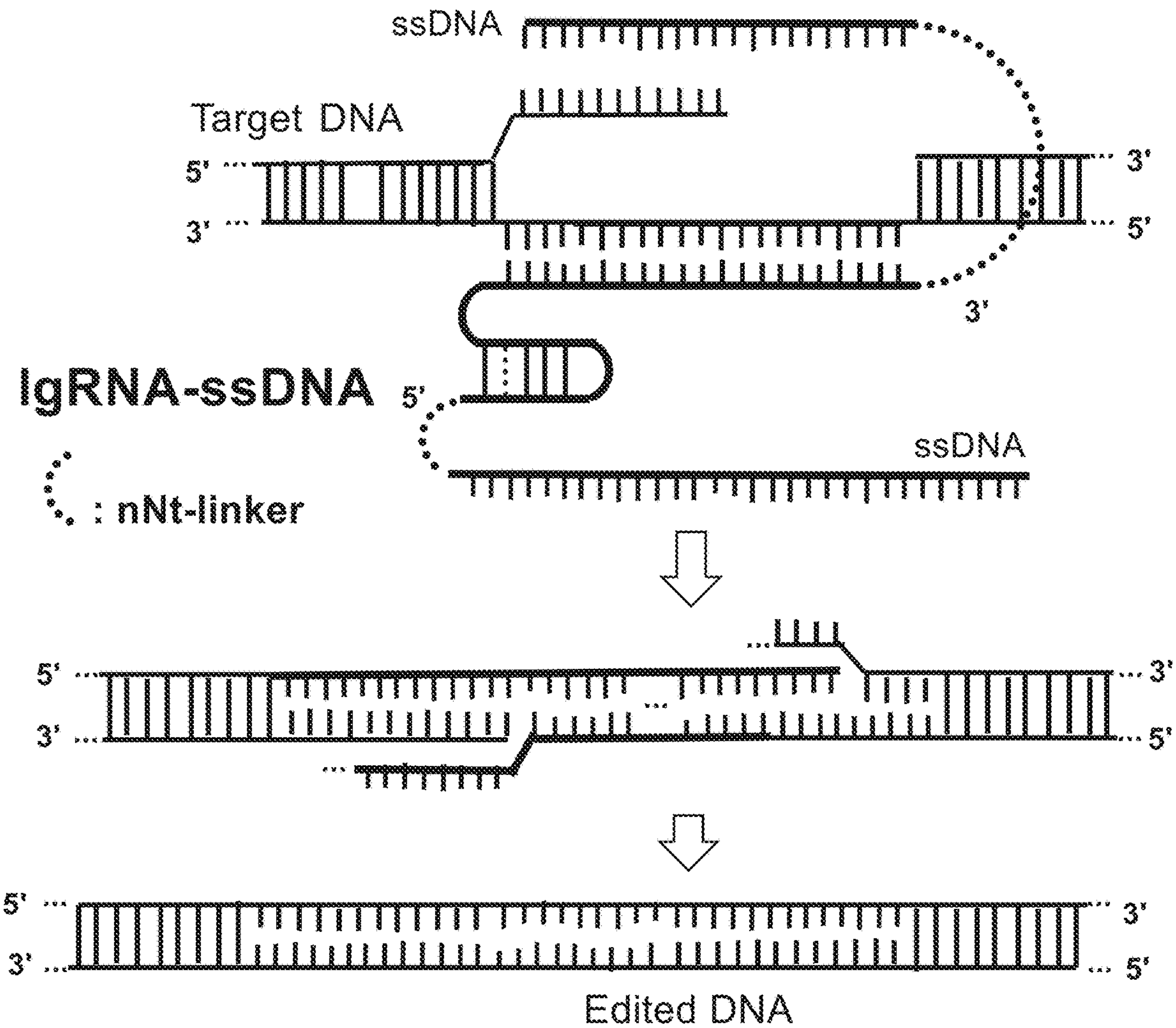
FIG. 10: DNA repair through microhomology-mediated end joining (MHEJ) pathway directed by lgRNA-ssDNA in Cpf1-based gene editing.
Figure 11:
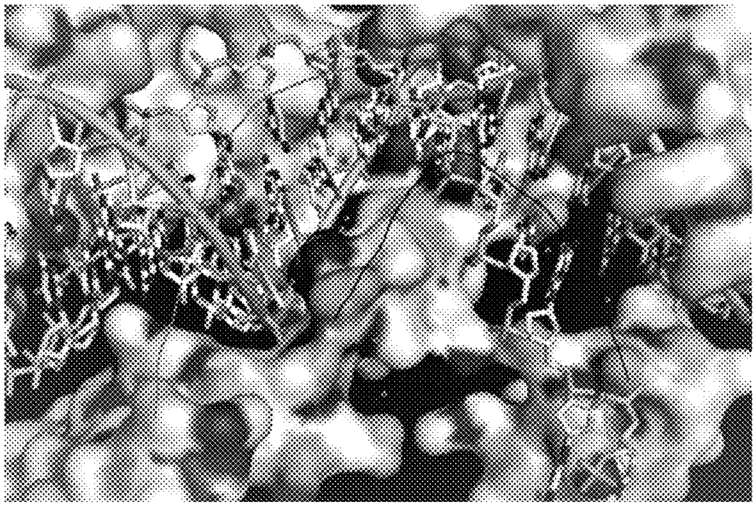
FIG. 11: Shape complementarity of Cas9-gRNA:DNA duplex recognitions.
Figure 12:
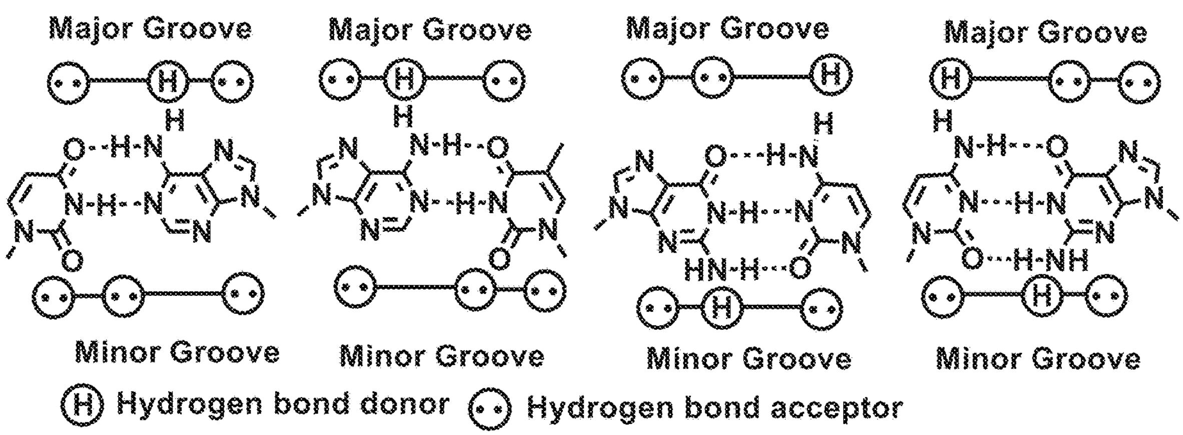
FIG. 12: Binding of Cas9 at major and minor grooves by hydrogen bonds.
Figure 13:
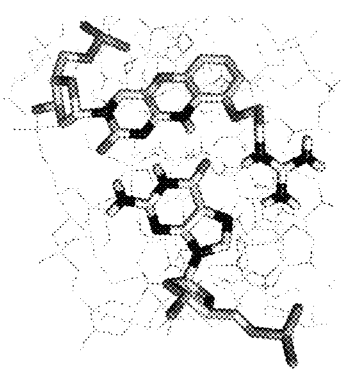
FIG. 13: Example of a bound G-Clamp.
Figure 14:
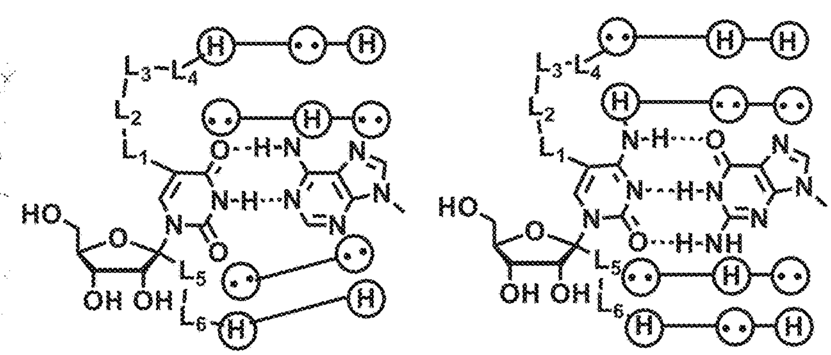
FIG. 14: Complementary hydrogen bonding in major and minor grooves of A-Clamps and G-Clamps.
Figure 15:
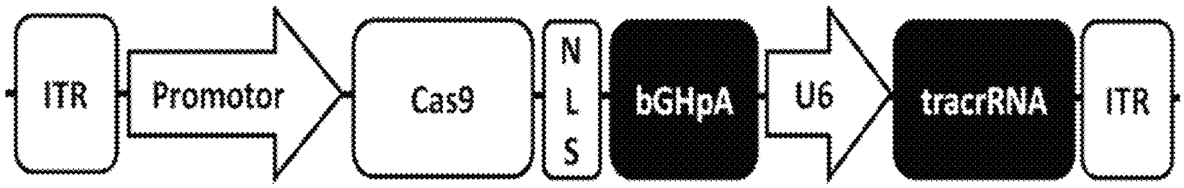
FIG. 15: AAV vector encoding a Cas9:tracrRNA complex. The promotors are tissue selective human promotors, which can be inducible, and Cas9 can be a dCas9-effector fusion protein or Cas9 nickase, or any other Cas protein.
Figure 16:
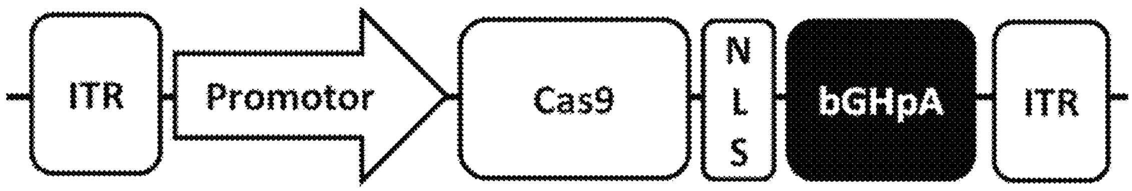
FIG. 16: AAV vector encoding a Cas9 protein. The promotors are tissue selective human promotors, which can be inducible, and Cas9 can be a dCas9-effector fusion protein or Cas9 nickase, or any other Cas protein.
Figure 17:
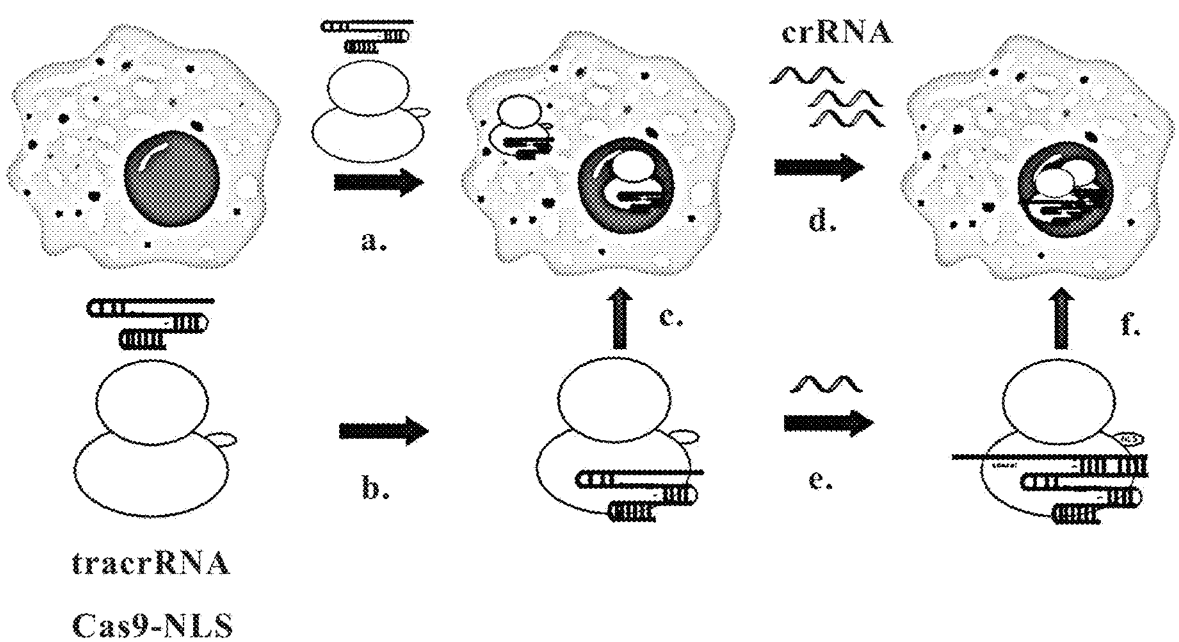
FIG. 17: Division of ternary Cas9:crRNA:tracrRNA RNP complexes into variable crRNA(s) and a fixed binary Cas9: tracrRNA RNP complex for its cellular delivery, and Cas9 can be a dCas9-effector fusion protein or Cas9 nickase, or any other Cas protein. A binary Cas9:tracrRNA RNP complex can be prepared in vitro and delivered to target cells (step b and c) or formed from a Cas9 protein and tacrRNA in target cells (step a). The binary Cas9:tracrRNA RNP complex forms a ternary Cas9:crRNA:tracrRNA RNP complex upon addition of crRNA(s) or its conjugates (step d). Ternary Cas9:crRNA:tracrRNA RNP complexes and their conjugates can also be alternatively prepared in vitro, and are delivered to target cells (step e and f).
Figure 18:
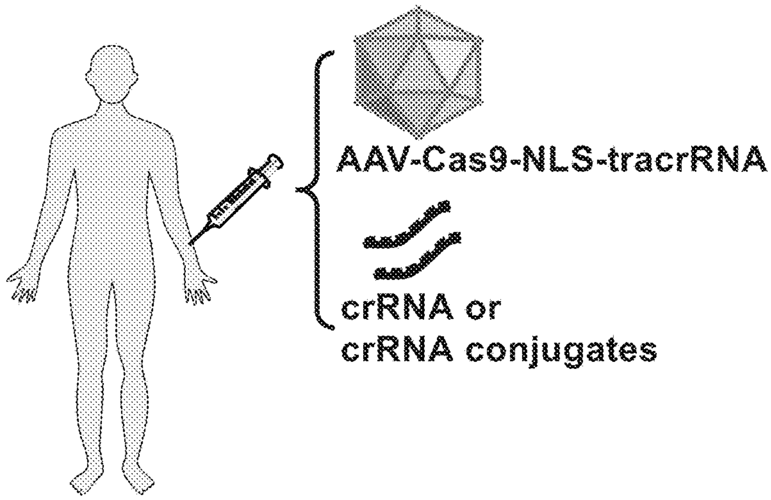
FIG. 18: Schematic depiction of administration of an AAV vector encoding both Cas9-NLS and tracrRNA, and crRNA/crRNA conjugates by injections.
Figure 19:
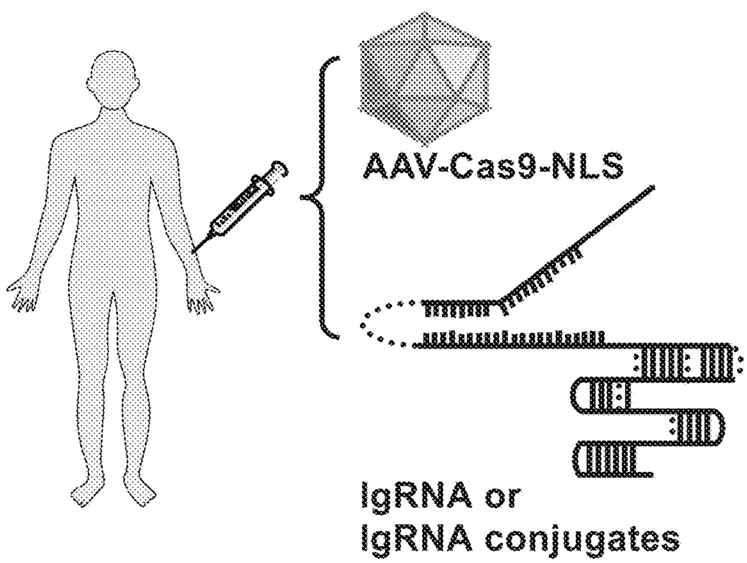
FIG. 19: Schematic depiction of administration of an AAV vector encoding Cas9-NLS, and lgRNA/lgRNA conjugates by injections.
Figure 20:
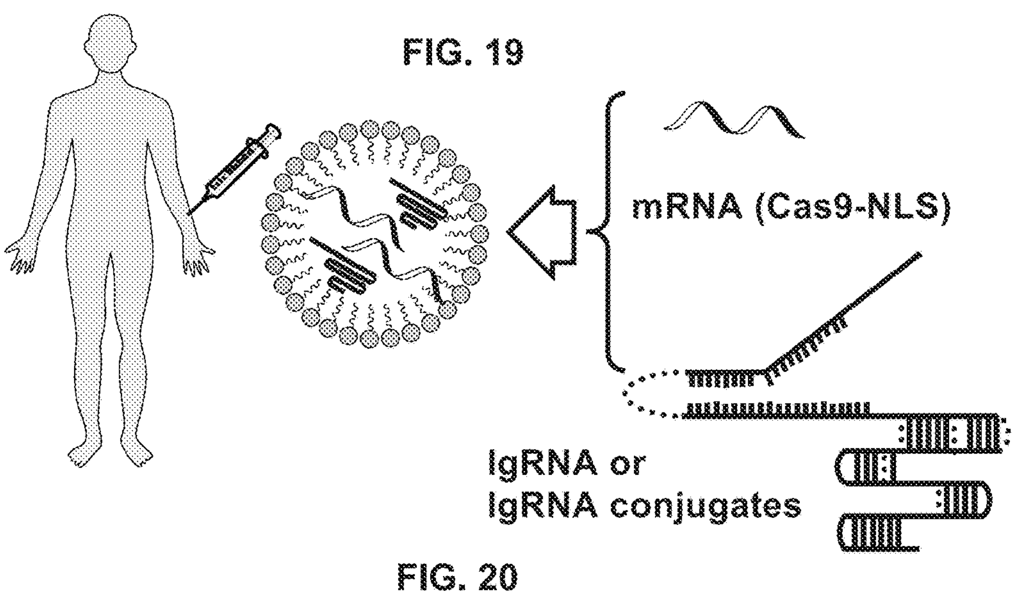
FIG. 20: Schematic depiction of administration of a mixture of mRNA(Cas9-NLS) and lgRNA-conjugates packaged in lipid nanoparticles by injections.
Figure 21:
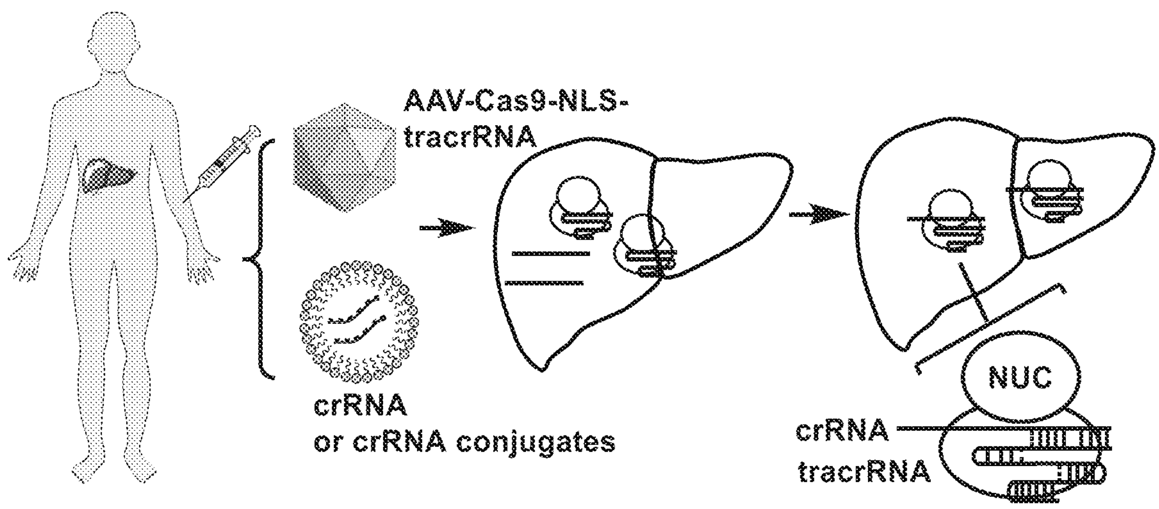
FIG. 21: Schematic depiction of administration of an AAV vector encoding both Cas9-NLS and tracrRNA, and crRNA/crRNA conjugates by IV injections and the formation of RNP complex conjugates in the liver.
Figure 22:
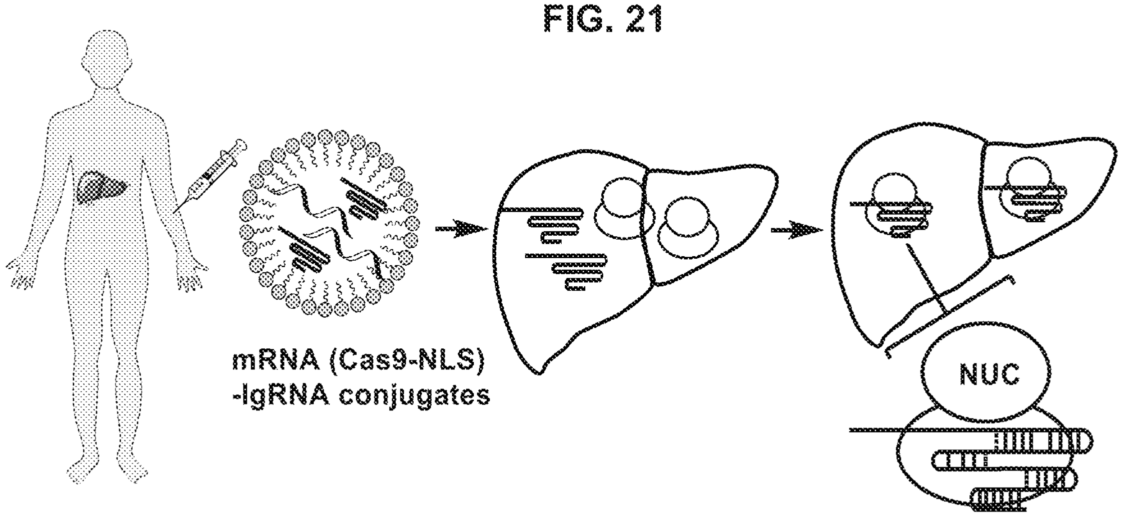
FIG. 22: Schematic depiction of administration of a mixture of mRNA(Cas9-NLS) and lgRNA/lgRNA-conjugates packaged in lipid nanoparticles by IV injections and the formation of RNP complex conjugates in the liver.
Figure 23:
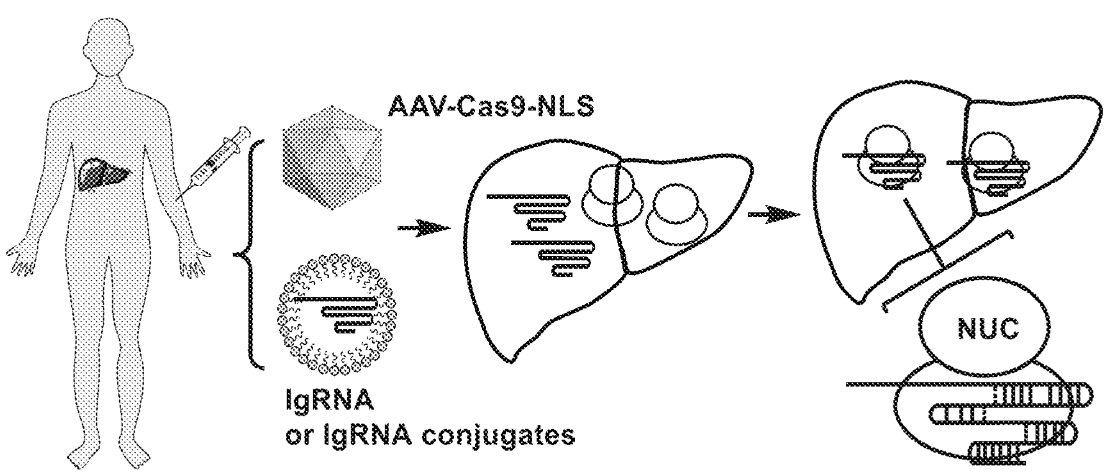
FIG. 23: Schematic depiction of administration of an AAV vector encoding Cas9-NLS, and lgRNA/lgRNA conjugates by IV injections and the formation of RNP complex conjugates in the liver.
Figure 24:
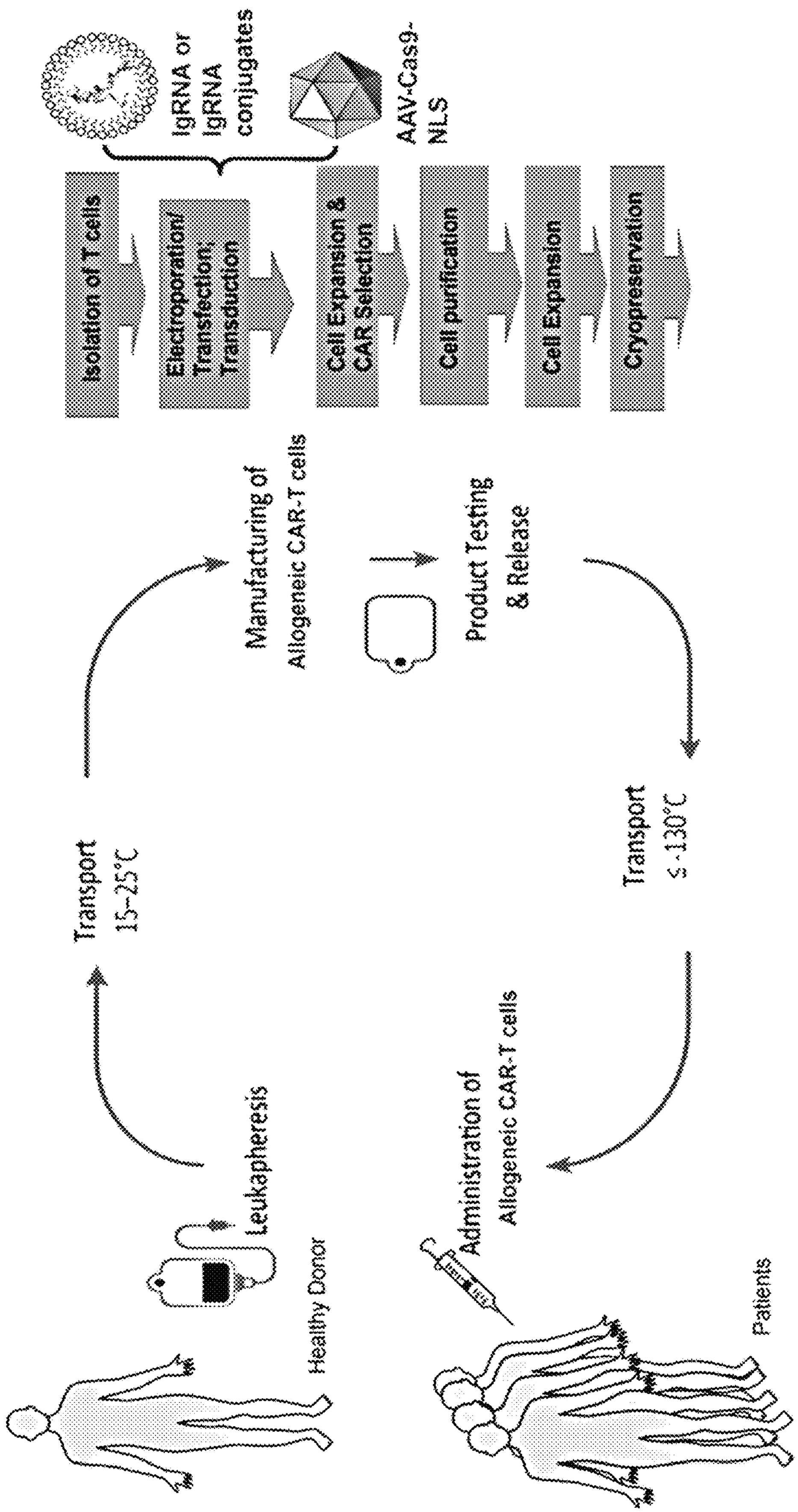
FIG. 24: Schematic depiction of ex vivo adoptive cell therapy (ACT): allogeneic universal CAR-T cells as an example.
Figure 25:
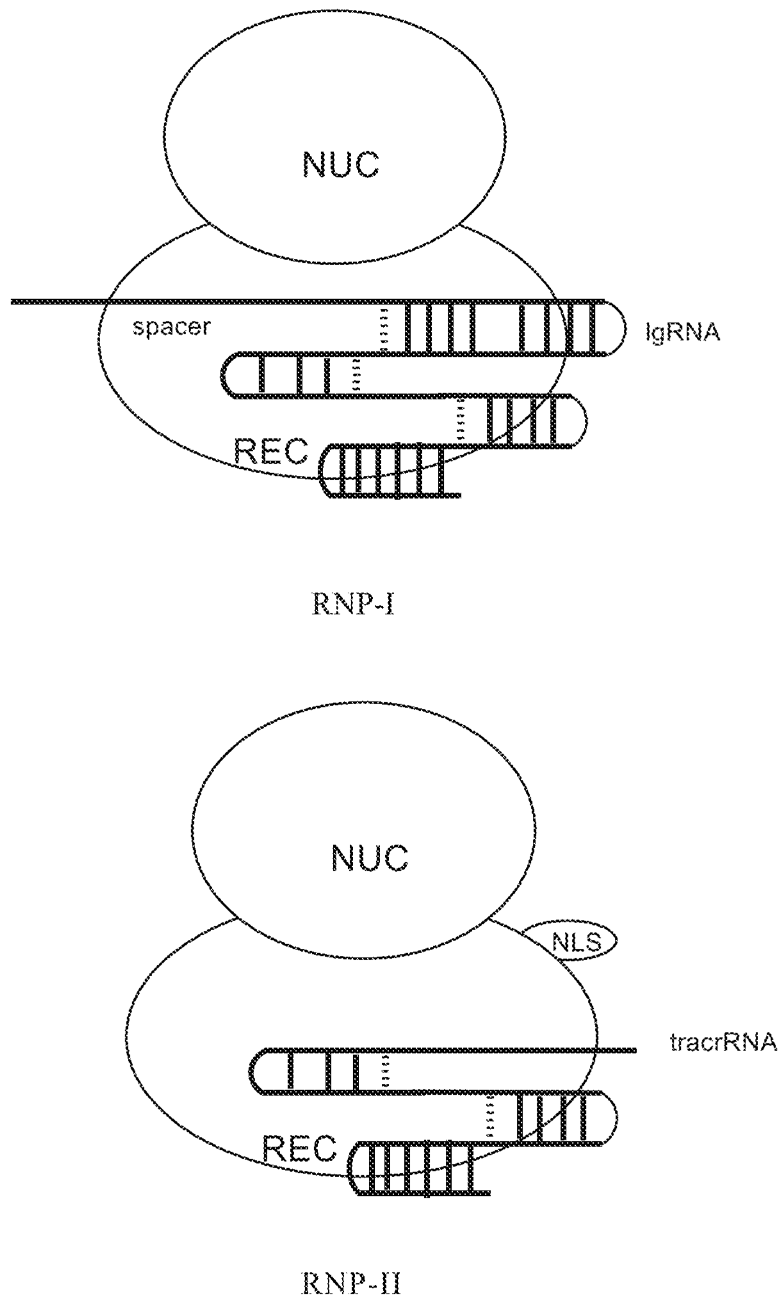
FIG. 25: Schematic depiction of guide RNA-CRISPR-Cas RNPs: RNP-I contains an lgRNA and RNP-II contains a tracrRNA.

In other embodiments, the conjugated single strand HDR/SSTR donor template (ssDNA) forms a duplex with its complementary stand, i.e. HDR donor template is a double strand DNA (dsDNA) covalently linked to guide RNA(s) via a linker to either of its double strands.

arm comprises an optionally chemically modified DNA or chimeric DNA/RNA oligonucleotide segment of 5 to 17 nucleotides complementary to 5'-end segment of the cleaved DNA strand (containing 3'-OH) which is also the primer for chain extension, and is joined at its 5'-end by an oligonucleotide comprising said gene editing sequence and said 5'-homology arm as a template for DNA synthesis (i.e. FIGS. 7-10).

In some embodiments, the said conjugated oligonucleotide is a donor template for DNA repair or serves as a bridging molecule to a second oligonucleotide via complementary hybridization.

(SEQ ID NO: 44)

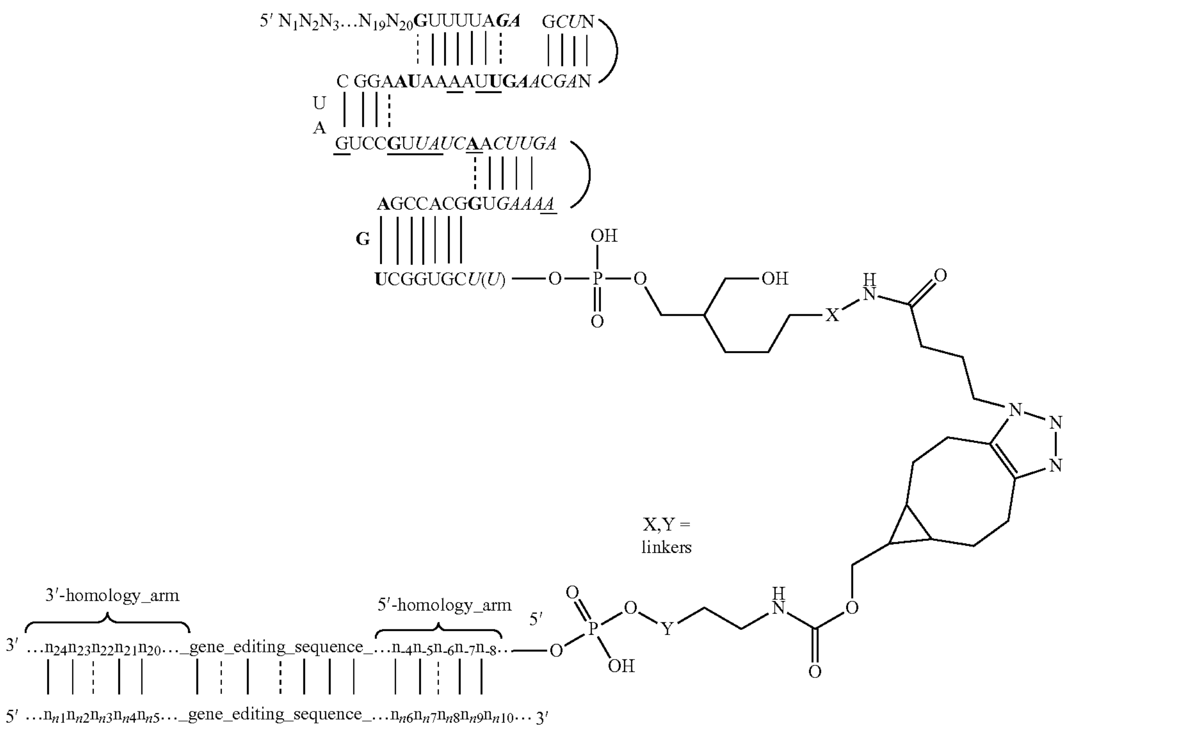

The said linker of X and Y is an L linker, a nucleotide linker or an nNt-linker and can be the same or different.

In some embodiments, the said conjugated oligonucleotide is a donor template which comprises two sequences overlapping with the target strand or with the non-target strand of the DNA duplex to be edited, e.g. 5'- and 3'-homology arms, and a gene editing sequence, and the said two sequences flanking the said gene editing sequence are optionally chemically modified, and the said 3'-homology arm comprises an optionally chemically modified DNA segment of 5 to 17 nucleotides complementary to 5'-end of the spacer of guide RNA, and is joined at its 5'-end by an oligonucleotide comprising said gene editing sequence and said 5'-homology arm as a template for DNA synthesis (i.e. FIGS. 7-10).

In some embodiments, the said conjugated oligonucleotide is a donor template which comprises two sequences overlapping with the target strand or with the non-target strand of the DNA duplex to be edited, e.g. 5'- and 3'-homology arms, and a gene editing sequence, and the said two sequences flanking the said gene editing sequence are optionally chemically modified, and the said 3'-homology In some embodiments, the two donor templates conjugated to guide RNA are for DNA chain extension of the target and non-target DNA strand in CRISPR-Cas mediated cleavage, respectively. DNA repair is directed toward microhomology-mediated end joining (MHEJ) pathway.

Non-Nucleotide Linkers (nNt-Linker)

An nNt-Linker, formed by chemical ligation, comprises an M core structure of Formula M-1 to M-13 as non-limiting examples:

M-1

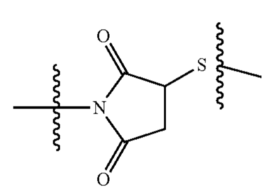

-continued
M-2
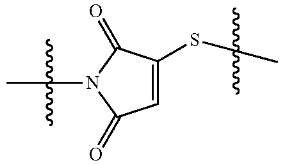
M-3
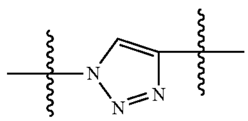
M-4
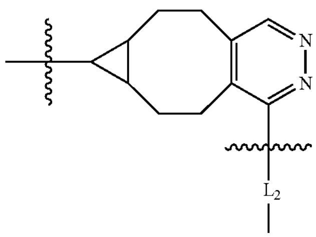
M-5
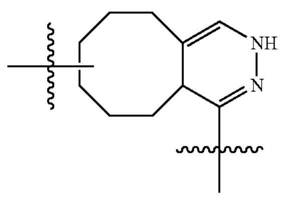
M-6
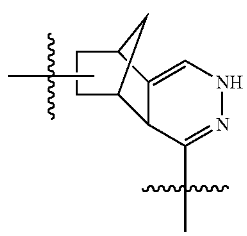
M-7
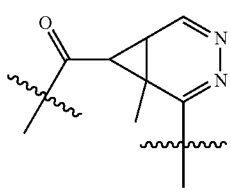
M-8
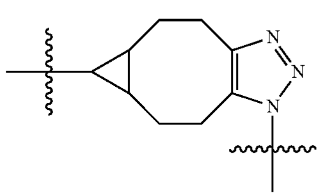
M-9
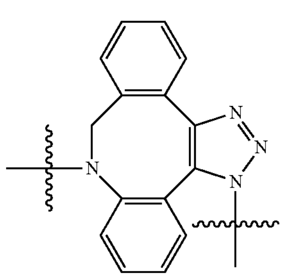
-continued
M-10
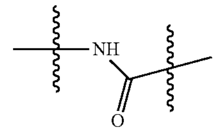
M-11
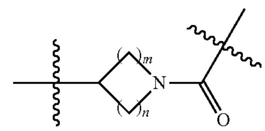
M-12
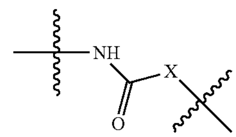
M-13
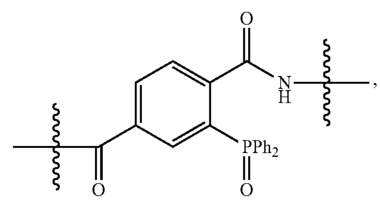,
wherein X=O, S, NH, or $CH_2$, m=0 to 3 and n=0 to 3, and two L linkers comprising Formula L-1 to L-23 as non-limiting examples:
L-1
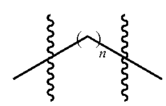
L-2
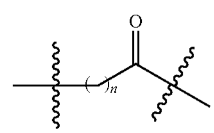
L-3
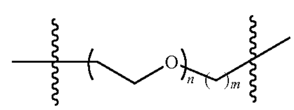
L-4
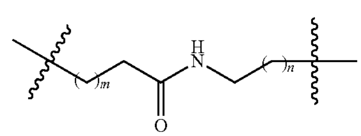
L-5
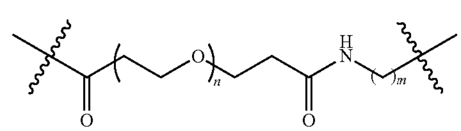
L-6
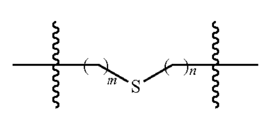

L-7
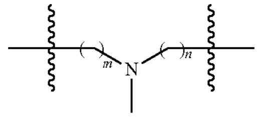
L-8
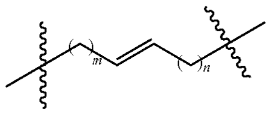
L-9
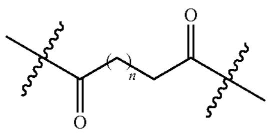
L-10
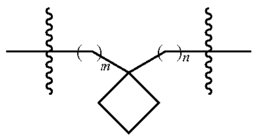
L-11
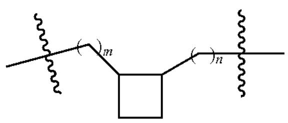
L-12
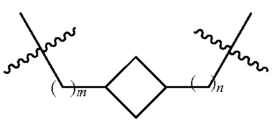
L-13
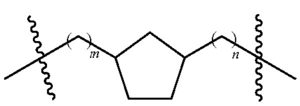
L-14
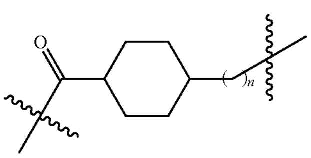
L-15
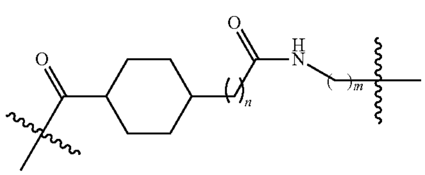
L-16
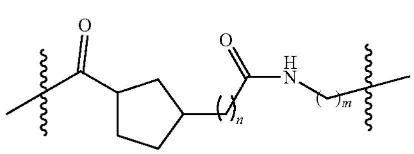
L-17
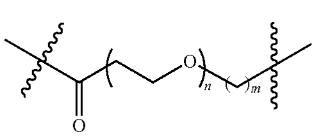
-continued
L-18
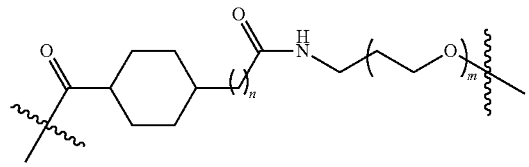
L-19
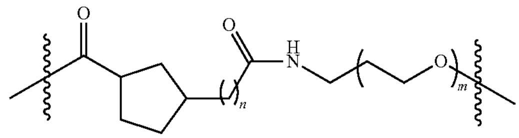
L-20
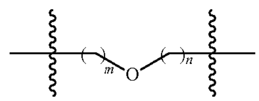
L-21
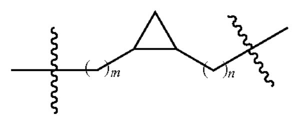
L-22
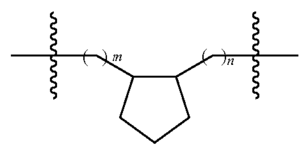
L-23
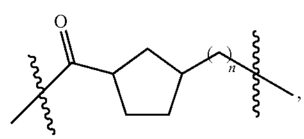
wherein m=0 to 16 and n=0 to 16,
said L linkers and said M core structure are joined as L-M-L, wherein the two L linkers are the same or different, and each L optionally comprises one or more structures of Formula L-1 to L-23 or partial structure (s), and attached to two terminal nucleotides of Formula Nuc-1 to Nuc-18 as non-limiting examples:
Nuc-1
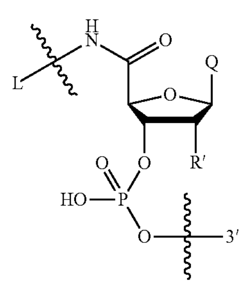

-continued
Nuc-2
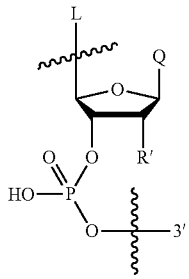
Nuc-3
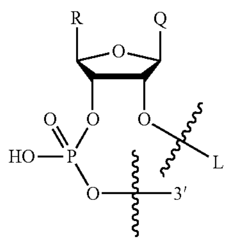
Nuc-4
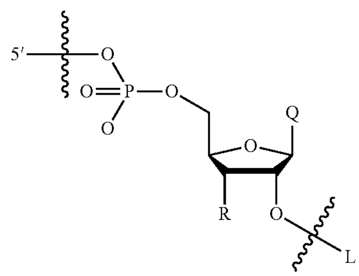
Nuc-5
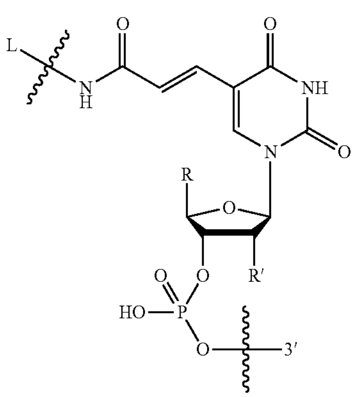
Nuc-6
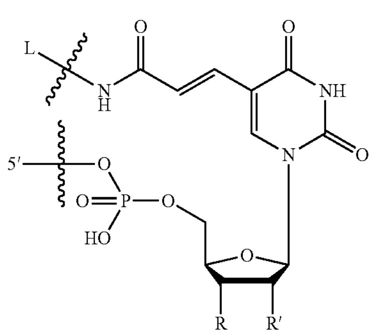
-continued
Nuc-7
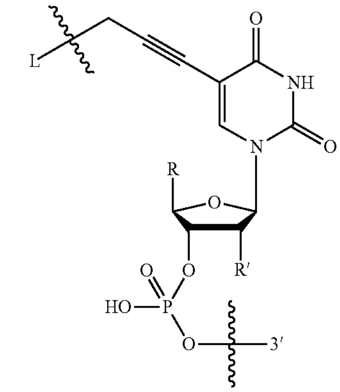
Nuc-8
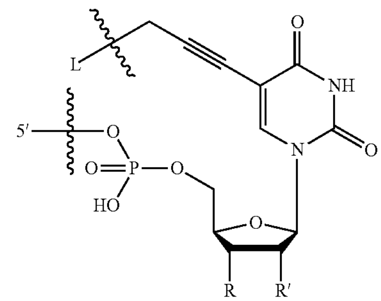
Nuc-9
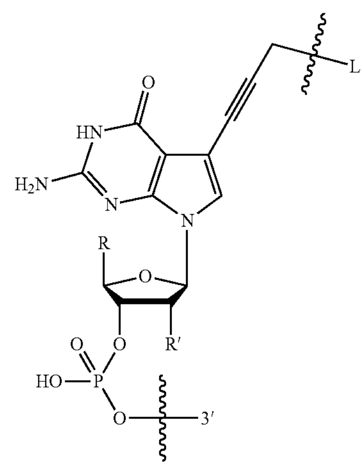
Nuc-10
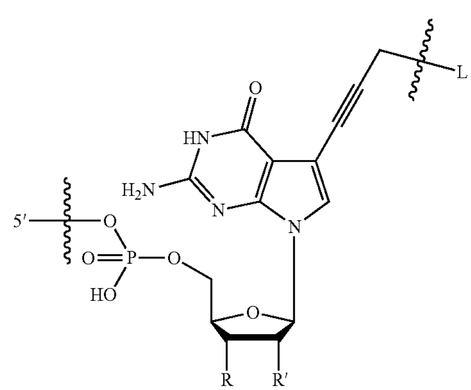

-continued
Nuc-11
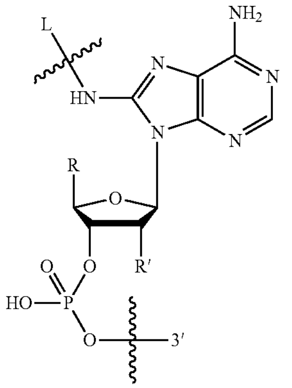
Nuc-12
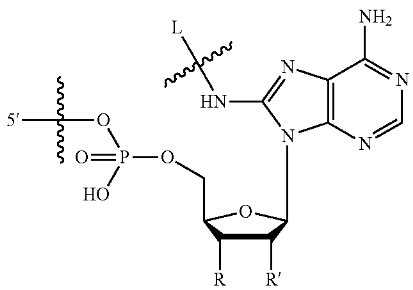
Nuc-13
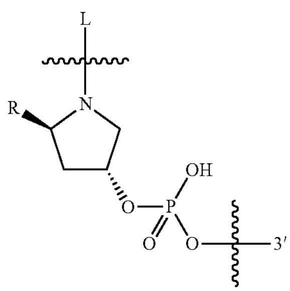
Nuc-14
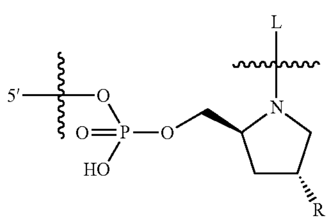
Nuc-15
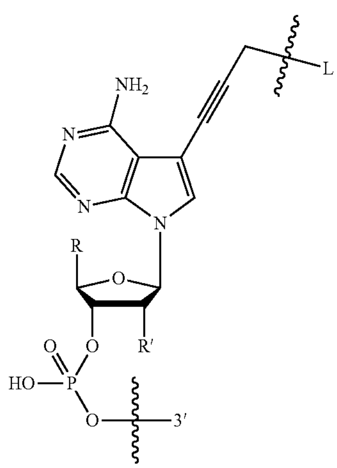
-continued
Nuc-16
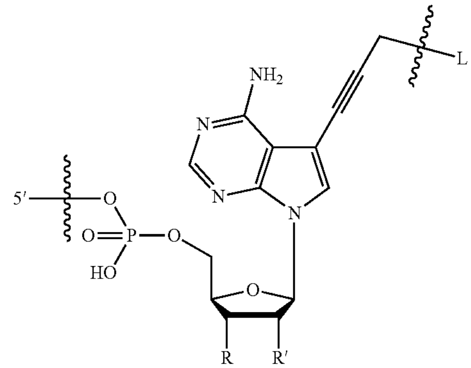
Nuc-17
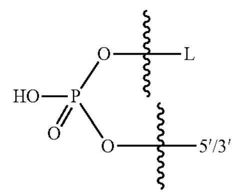
Nuc-18
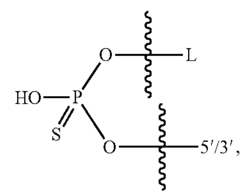
wherein the attached positions are
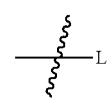
to L-M-L and
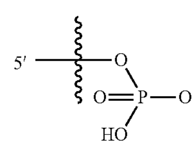
or
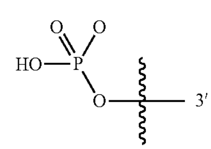
to upstream and downstream oligonucleotides, respectively, and wherein R is H, OH,
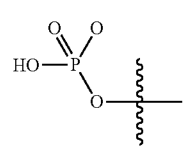
, $CH_2OH$,

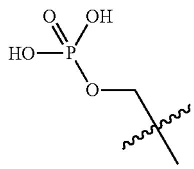
,

F, $NH_2$, OMe, $CH_2OMe$, $OCH_2CH_2OMe$, an alkyl, a cycloalkyl, an aryl, or heteroaryl, R' is H, OH,

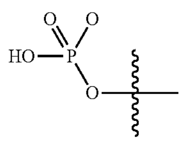
, $CH_2OH$,

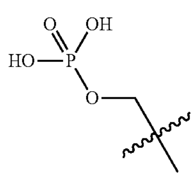
,

F, $NH_2$, OMe, $CH_2OMe$, $OCH_2CH_2OMe$, an alkyl, a cycloalkyl, an aryl, or a heteroaryl, and Q is a natural or a non-natural nucleic acid base.

In some embodiments, the M core structure, L, and terminal nucleotides are optionally modified with substituents such as halogen (F, Cl, Br, I), lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, CN, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, an optionally substituted aryl, an optionally substituted heteroaryl, an optionally substituted sulfonyl, or optionally substituted acyl, which includes but is not limited to C(═O) alkyl, $NR'_2$, CN, $CO_2H$, $CO_2R'$, $CONH_2$, CONHR', $CONR'_2$, CH═$CHCO_2H$, or CH═$CHCO_2R'$, wherein R' is an optionally substituted alkyl, which includes, but is not limited to, H, an optionally substituted $C_1$-$C_{20}$ alkyl, an optionally substituted lower alkyl, an optionally substituted cycloalkyl, an optionally substituted alkynyl of $C_2$-$C_6$, an optionally substituted lower alkenyl of $C_2$-$C_6$, an optionally substituted aryl, an optionally substituted heteroaryl, an optionally substituted sulfonyl, or optionally substituted acyl, which includes but is not limited to C(═O) alkyl, or alternatively, in the instance of $NR'_2$, each R' comprise at least one C atom that are joined to form a heterocycle comprising at least two carbon atoms.

In some embodiments, an nNt-Linker joins the 3'-terminal nucleotide of a crRNA and the 5'-terminal nucleotide of a tracrRNA. In some embodiments, an nNt-Linker joins the 5'-terminal nucleotide of a crRNA and the 3'-terminal nucleotide of a tracrRNA. In some embodiments, an nNt-Linker joins two oligonucleotide segments of tracrRNA.

In some embodiments, one of the two L's in an nNt-linker (L-M-L) is covalently linked to guide RNA(s), and the other is covalently linked to a PEG polymers, a non-PEG polymer, a ligand for cellular receptors, a lipid, an oligonucleotide, an antibody, a polysaccharides or a peptide.

In some embodiments, one of the two L's in nNt-linkers (L-M-L) is covalently linked to an exposed amino acid residue of Cas protein such as lysine, serine, and cysteines, and the other is covalently linked to a PEG polymers, a non-PEG polymer, a ligand for cellular receptors, a lipid, an oligonucleotide, an antibody, a polysaccharides or a peptide.

In some embodiments, the nNt-linkers between the two nucleotides/nucleosides are represented by the following formulas:

nNt-L-01

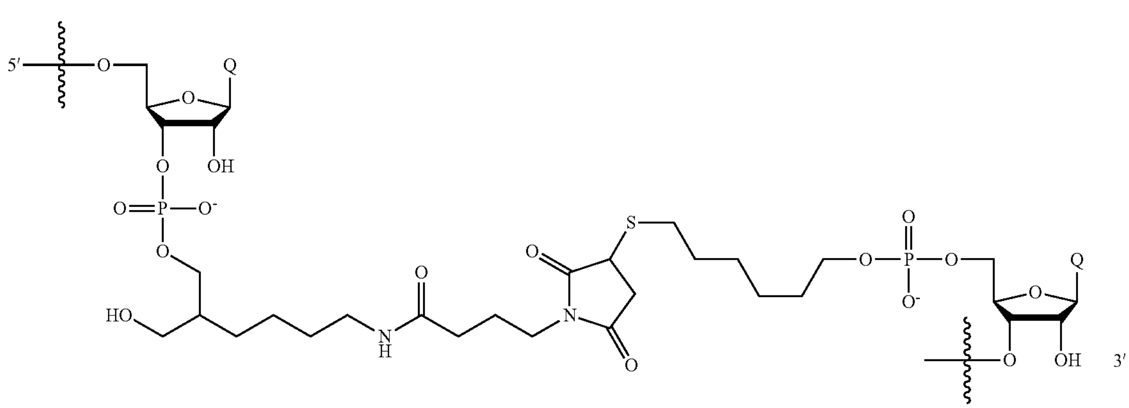

-continued
nNt-L-02
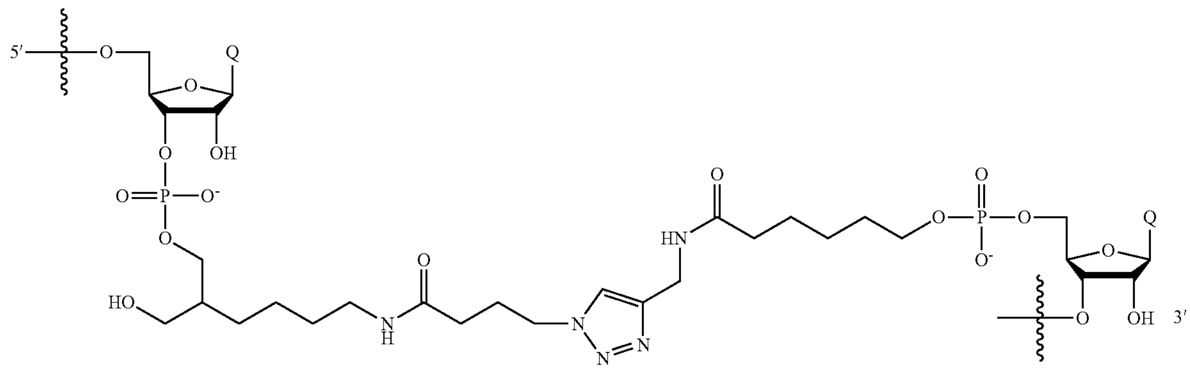
nNt-L-03
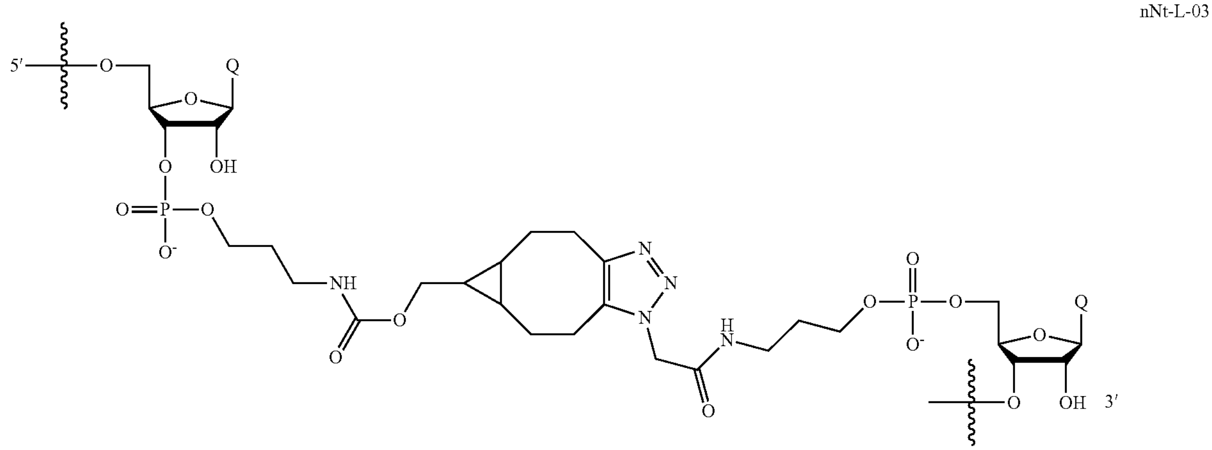
nNt-L-04
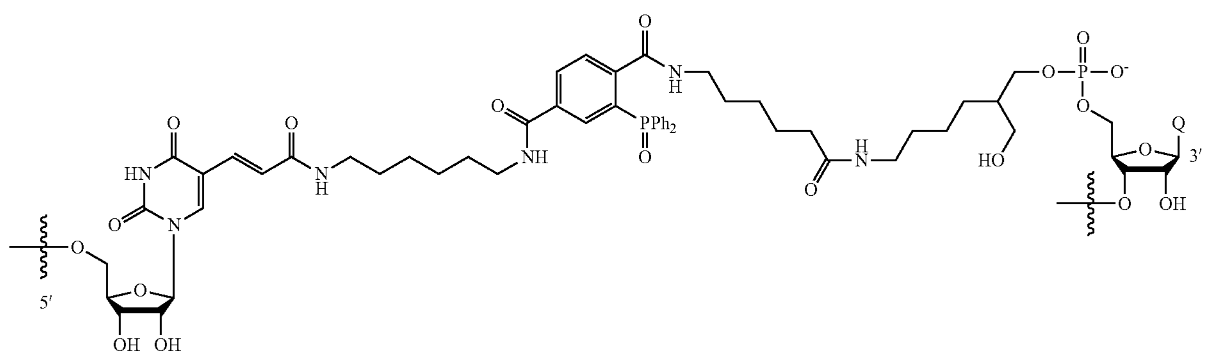
nNt-L-05
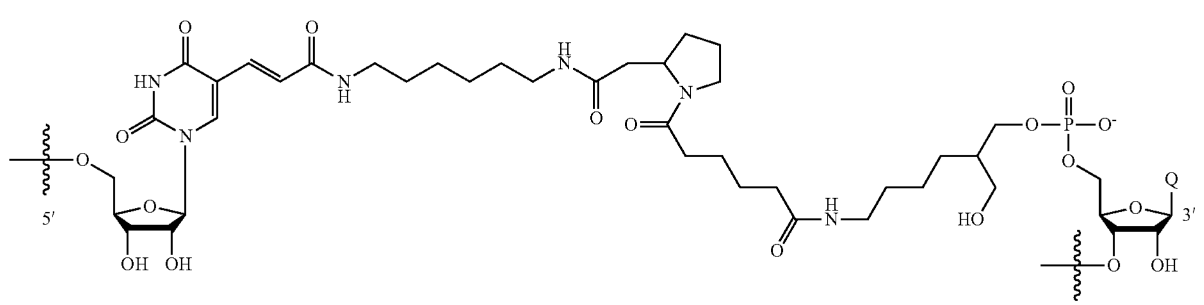

-continued nNt-L-06

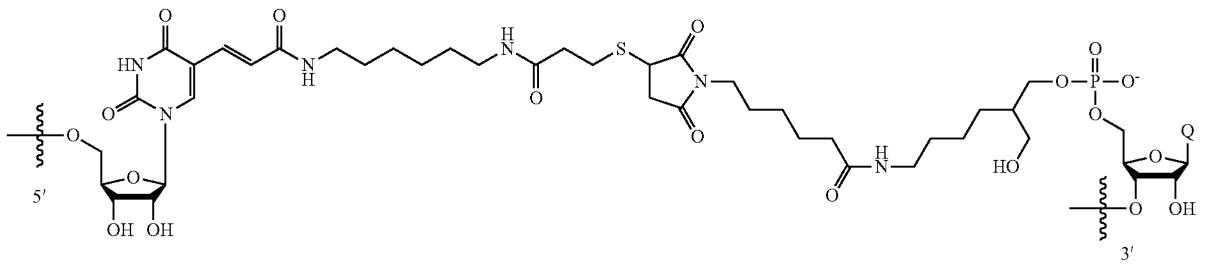

nNt-L-07

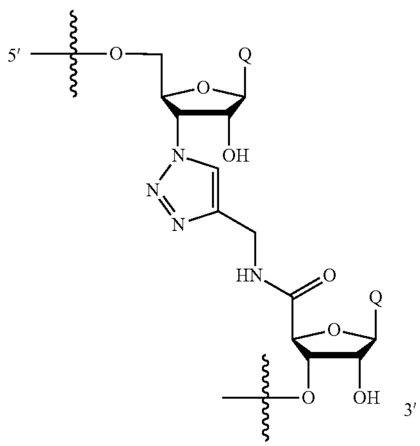

nNt-L-08

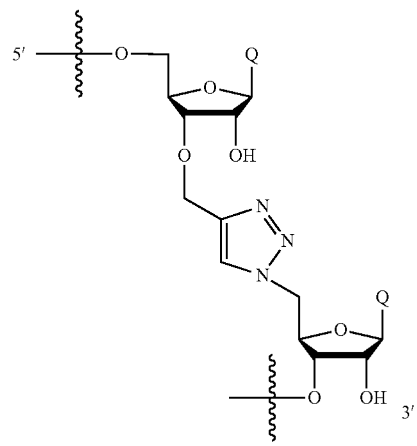

nNt-L-09

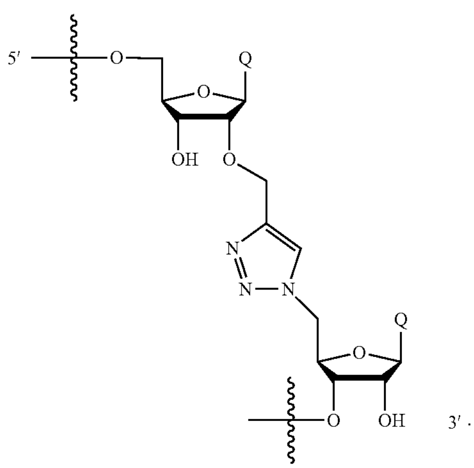

CRISPR Effector Proteins

In some embodiments, CRISPR effector endonuclease is selected from Cas proteins of Type II, Class 2 including *Streptococcus pyogenes*-derived Cas9 (SpCas9, 4.1 kb), smaller Cas9 orthologues, including *Staphylococcus aureus*-derived Cas9 (SaCas9, 3.16 kb), *Campylobacter jejuni*-derived Cas9 (CjCas9, 2.95 kb), *Streptococcus thermophilus* Cas9 (St1Cas9, 3.3 kb), *Neisseria meningitidis* Cas9 (NmCas9, 3.2 kb), and many other variants of engineered Cas9 proteins such as SpCas9-HF1, eSpCas9, and HypaCas9, proteins of Type V, Class 2 including Cas12 (Cas12a (Cpf1), Cas12b (C2c1), Cas 12c, Cas12e, Cas12g, Cas12h, Cas12i, and etc.) and Cas14, and proteins of Type VI, Class 2 such as Cas13a and Cas13b. The said CRISPR effector protein can be a nickase e.g. nCas9 such as a SpCas9-nickase (D10A or H840A), or a catalytically inactive protein e.g. dCas9 coupled/fused with a protein effector such as a DNA polymerase, FokI, transcription activator(s), transcription repressor(s), catalytic domains of DNA methyltransferase, histone acetyltransferase and deacetylase, reverse transcriptase (prime editor), and nucleic acid deaminases (base editor) at its either N- or C-terminal.

In another embodiment, the said CRISPR effector endonuclease is an artificial one comprising one or more functional domains derived from human.

In yet another embodiment, the said CRISPR effector endonuclease is a class 2 CRISPR Cas protein functionalized by site-directed mutagenesis to introduce orthogonal conjugating sites such as cysteines and remove deleterious conjugating sites (e.g. C80 in SpCas9), and corresponding RNP conjugates are prepared by selective conjugations such as PEGylation of cysteines by maleimide chemistry.

In yet another embodiment, the said CRISPR effector endonuclease is a class 2 CRISPR Cas protein fused with a human DNA or RNA polymerase via a peptide linker.

In yet another embodiment, the RNP complex conjugates are synthesized by reactions with crosslinking reagents, or by enzymes such as TGase which catalyzes amine transfer reaction between a primary amine at terminal side of PEG and the carboxamide of glutamine.

Tissue Tropic Viral Vectors Encoding a Cas Protein or a Cas-TracrRNA Complex

In some embodiments, the said viral vector encoding a Cas effector endonuclease such as Cas9, or a Cas9-tracrRNA complex, is a retrovirus, lentivirus, adenovirus, AAV, or baculovirus.

In some embodiments, the said viral vector encoding a Cas effector endonuclease such as Cas9, or a Cas9-tracrRNA complex, is an engineered AAV or AAV chimera to enable high transduction efficiency at a targeted tissue by changing the tropism of AAV capsids and to have low immunogenicity by evading human preexisting anti-AAV capsid neutralizing antibodies.

In some embodiments, the said viral vector encoding a Cas effector endonuclease such as Cas9, or a Cas9-tracrRNA complex, is a native or an engineered AAV to enable brain tissue targeted delivery. Such AAV serotypes include as non-limiting examples AAV1, AAV2/DJ, AAV2/DJ8, AAV2g9, AAV2-retro and scAAV9.

In some embodiments, the said viral vector encoding a Cas effector endonuclease such as Cas9, or a Cas9-tracrRNA complex, is a native or an engineered AAV to enable liver tissue targeted delivery. Such AAV serotypes include as non-limiting examples AAV8 and AAV3.

In some embodiments, the said viral vector encoding a Cas effector endonuclease such as Cas9, or a Cas9-tracrRNA complex, is a native or an engineered AAV to enable muscle tissue targeted delivery. Such AAV serotypes include as non-limiting examples AAV6, AAV8 and AAV9.

In some embodiments, the said viral vector encoding a Cas effector endonuclease such as Cas9, or a Cas9-tracrRNA complex, is a native or an engineered AAV to enable heart tissue targeted delivery. Such AAV serotypes include as non-limiting examples AAV rh74 and AAV9.

In some embodiments, the said viral vector encoding a Cas effector endonuclease such as Cas9, or a Cas9-tracrRNA complex, is a native or an engineered AAV to enable retina tissue targeted delivery. Such AAV serotypes include as non-limiting examples AAV1, AAV2, AAV5, AAV8 and AAV9.

In some embodiments, the said viral vector encoding a Cas effector endonuclease such as Cas9, or a Cas9-tracrRNA complex, is a native or an engineered AAV to enable lung tissue targeted delivery. Such AAV serotypes include as non-limiting examples AAV9.

In some embodiments, the expression of a Cas effector endonuclease such as Cas9, or a Cas9-tracrRNA complex by the said viral vector, is driven by inducible tissue-specific promoters.

In some embodiments, the expression of a Cas effector endonuclease such as Cas9, or a Cas9-tracrRNA complex by the said viral vector, is driven by brain tissue-specific promoters such as pMecp2, hSyn1, TRE3G and EFS as non-limiting examples.

In some embodiments, the expression of a Cas effector endonuclease such as Cas9, or a Cas9-tracrRNA complex by the said viral vector, is driven by liver tissue-specific promoters such as TBG and HCRhAATp or by lung tissue-specific promoters such as EFS, as non-limiting examples.

In some embodiments, the expression of a Cas effector endonuclease such as Cas9, or a Cas9-tracrRNA complex by the said viral vector, is driven by heart tissue-specific promoters such as CMV, Myh6, CB and CK7-miniCMV as non-limiting examples.

In some embodiments, the expression of a Cas effector endonuclease such as Cas9, or a Cas9-tracrRNA complex by the said viral vector, is driven by retina tissue-specific promoters such as EFS, CMV, Spc512, pMecp2, and Picam2 as non-limiting examples.

In some embodiments, the expression of a Cas effector endonuclease such as Cas9, or a Cas9-tracrRNA complex by the said viral vector, is driven by muscle tissue-specific promoters such as CMV, EFS and CK8 as non-limiting examples.

In some embodiments, the said viral vector encoding a Cas effector endonuclease such as Cas9, or a Cas9-tracrRNA complex, is administrated locally or systematically to optimize tissue targeted deliveries in animals and human. The injection site is intravenous, subcutaneous, intramuscular, intradermal, intraperitoneal, intravitreal, intranasal, intratracheal, subretinal, intraocular, or intracardiac, or at other sites. Chemically modified lgRNA(s), sgRNA(s), crRNA(s), or their conjugates are administrated either in an aqueous solution gymnotically or with transfection reagents or in a non-viral carrier by co-injections or separate injections.

In some embodiments, the said viral vector encoding a Cas effector endonuclease such as Cas9, or a Cas9-tracrRNA complex, is administrated to isolated cells including T cells, and chemically modified lgRNA(s), or crRNA(s) are administrated either in an aqueous solution gymnotically by electroporation or microinjection, or with transfection reagents or in a non-viral carrier.

Non-Viral Delivery of RNP Complexes

In some embodiments, guide RNA conjugates, conjugates of guide RNA(s)-Cas protein (RNP) complexes such as PEGylated RNP complexes, or mixed lgRNA conjugate(s) and an mRNA encoding a Cas-NLS protein are delivered with lipids well used in delivery of therapeutic nucleic acids such as DOPE, DOTAP, DOPS, DLin-MC3-DMA, cKK-E12, DSPC, POPE, 503O13, PEG-DMG, bio-reducible lipid 8-O14B, cholesterol, and etc.

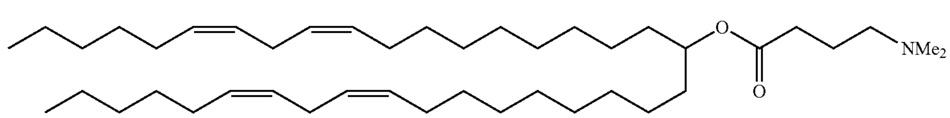

DLin-MC3-DMA

-continued

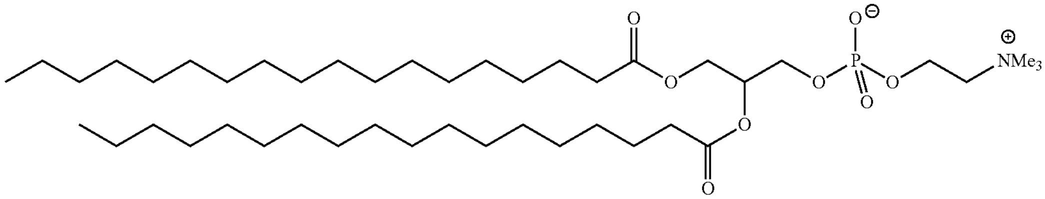

DSPC

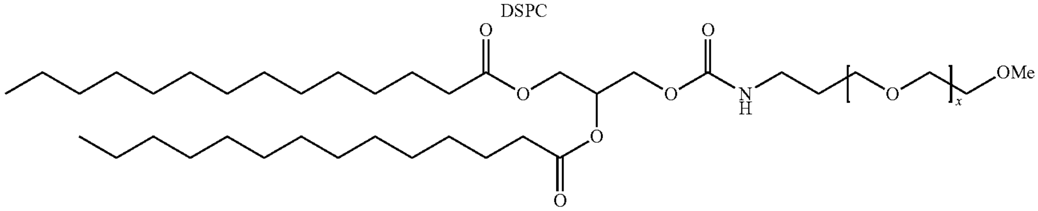

PEG-DMG

In other embodiments, conjugates of guide RNA(s)-Cas protein (RNP) complexes such as PEGylated RNP complexes are delivered within lipid nanoparticles, liposomes, or exosomes.

In yet another embodiment, conjugates of guide RNA(s) and an mRNA encoding a Cas protein are delivered within lipid nanoparticles, liposomes, or exosomes.

In yet another embodiment, conjugates of guide RNA(s) are delivered with lipids or peptides, or within lipid nanoparticles, liposomes, or exosomes to cells stably or inducibly expressing a Cas protein, or to cells with a viral vector encoding a Cas protein co-delivered.

In yet another embodiment, conjugates of crRNA(s) are delivered with lipids or peptides, or within lipid nanoparticles, liposomes, or exosomes to cells stably or inducibly expressing both a Cas9 protein and a tracrRNA, or to cells with a viral vector encoding both a Cas9 protein and a tracrRNA co-delivered.

In some embodiments, the said crRNA(s), or lgRNAs, or sgRNAs, or their conjugates or conjugates of guide RNA (s)-Cas protein (RNP) complexes are administrated by electroporation or microinjection.

Conjugates of RNP Complexes

An aspect of the invention is directed to conjugates of guide RNA(s)-Cas protein (RNP) complexes such as a PEGylated CRISPR Cas protein-guide RNA complex(es), which are prepared by conjugation of a preformed guide RNA-CRISPR-Cas RNP(s) (RNP-I as an example), or prepared by conjugation of a Cas protein engineered for site-selective conjugations followed by complexing with a guide RNA(s) to form an RNP complex, wherein guide RNA(s) is an lgRNA, a crRNA, an sgRNA, or dual guide RNAs, and Cas protein is Cas9 comprising a nuclease lobe (NUC) and a recognition lobe (REC), an engineered Cas9, or a Cas protein other than the example of *S. pyogenes* Cas9 represented here; wherein lgRNA is composed of dual-modules (crRNA and tracrRNA) and a single nNt-linker, dual or multiple nNt-linkers (lgRNA) formed by chemical ligation (s) and the ligation sites are preferably located at tetraloop (A32-U37) and/or stem 2 (C70-G79) (of reported sgRNA engineered for *S. pyogenes* Cas9), while any 3', 5'-phosphodiester of sgRNA can be replaced by an nNt-Linker as a ligation site; and wherein guide RNA(s) is chemically modified and optionally conjugated with one or more molecules selected from a group comprising PEG, non-PEG polymers, ligands for cellular receptors, lipids, oligonucleotides, antibodies, polysaccharides and peptides.

Another aspect of the invention is directed to viral vectors or plasmids, encoding binary CRISPR-Cas9-tracrRNA RNP complexes (RNP-II as an example) which further complex with crRNAs or crRNA conjugates in targeted cells, wherein Cas9 comprising a nuclease lobe (NUC) and a recognition lobe (REC) can be a Cas protein other than the example of *S. pyogenes* Cas9 represented here, and can be an engineered Cas protein.

Another aspect of the invention is directed to a PEGylated CRISPR Cas protein-guide RNA complex(es), wherein the guide RNA(s) is a crRNA, dual guide RNAs, an sgRNA or an lgRNA.

Another aspect of the invention is directed to a CRISPR Cas protein conjugated with one or more molecules selected from a group comprising PEG, non-PEG polymers, ligands for cellular receptors, lipids, oligonucleotides, antibodies, polysaccharides and peptides.

Another aspect of the invention is directed to a conjugate of CRISPR Cas protein-guide RNA complex(es), wherein the guide RNA(s) is a conjugate of a crRNA, dual guide RNAs, an sgRNA or an lgRNA with one or more single strand DNAs (ssDNA) as a donor template for gene editing.

Another aspect of the invention is directed to a conjugate of CRISPR Cas protein-guide RNA complex(es), wherein the said guide RNA(s) is a conjugate of a crRNA, dual guide RNAs, an sgRNA or an lgRNA with one or more single strand DNAs as a donor template for gene editing, and the CRISPR Cas protein is conjugated with one or more molecules selected from a group comprising PEG, non-PEG polymers, ligands for cellular receptors, lipids, oligonucleotides, antibodies, polysaccharides and peptides.

Some non-limiting examples of PEGylating reagents are given below.

PEG-1

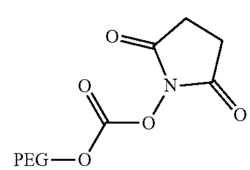

-continued
PEG-2
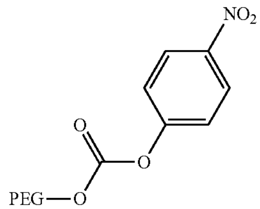
PEG-3
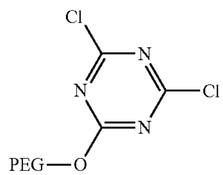
PEG-4
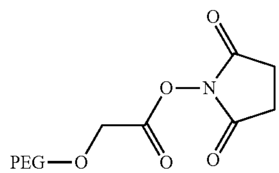
PEG-5
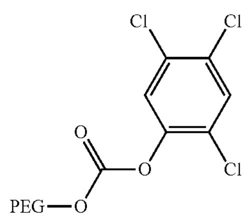
PEG-6
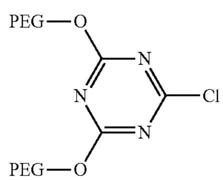
-continued
PEG-7
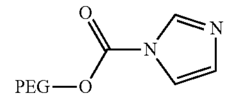
PEG-8
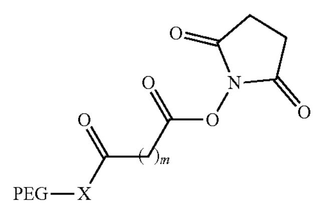
X = O, NH
m = 2, 3
PEG-9
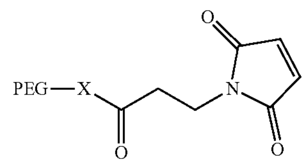
PEG-10
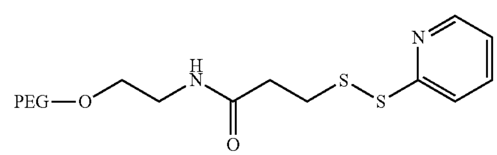
The PEG can be either linear or branched and conjugated at a lysine or cysteine residue:
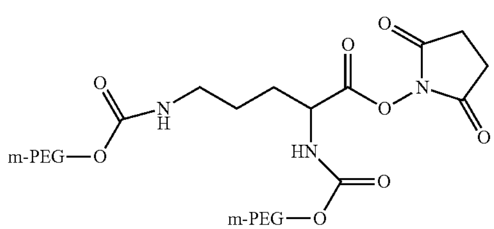
m-PEG-1
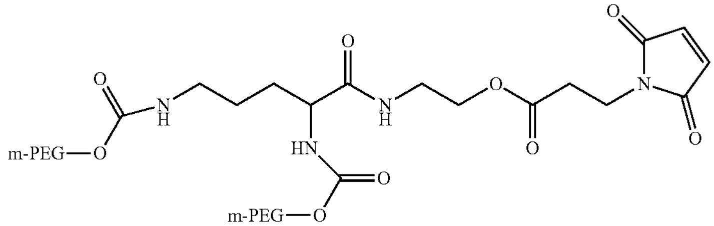
m-PEG-2

-continued

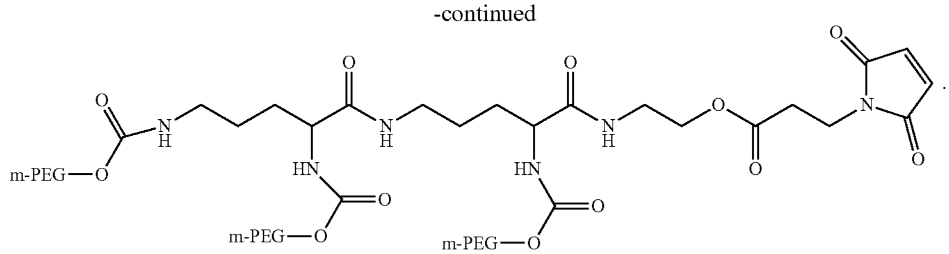

m-PEG-3

Another aspect of the invention is directed to a lipid conjugated Cas protein-guide RNA complex, which is prepared by lipid conjugation of a preformed CRISPR-Cas RNP complex or by lipid conjugation of a Cas protein engineered for site-selective conjugations followed by complexing with a guide RNA to form an RNP complex.

Some non-limiting examples of lipid conjugating reagents are given below:

LIP-1

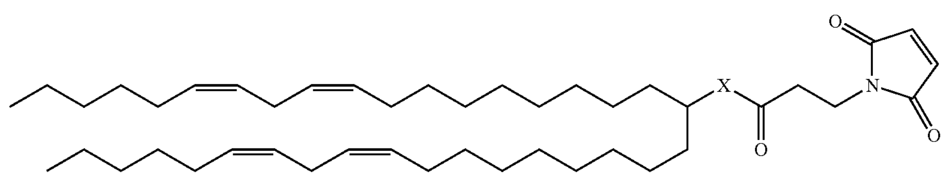

LIP-2

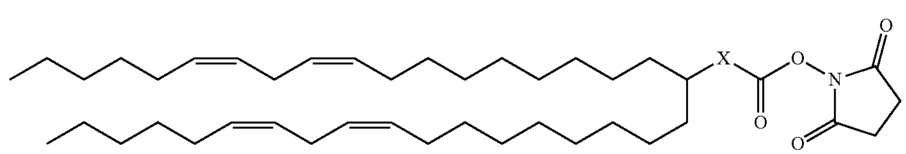

LIP-3

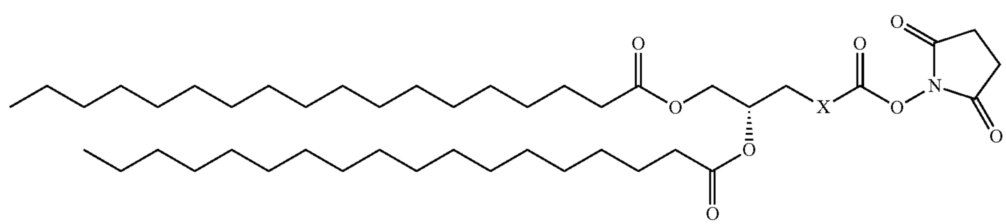

LIP-4

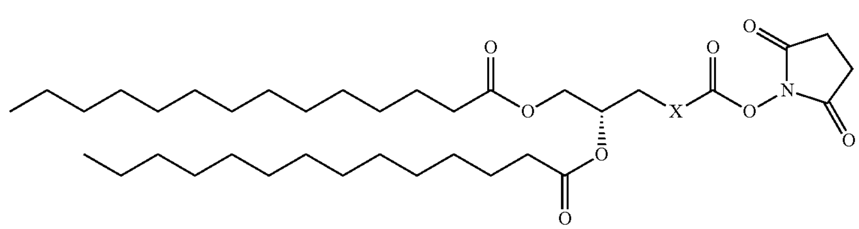

X = O, NH

Another aspect of the invention is directed to a peptide conjugated Cas protein-guide RNA complex, which is prepared by peptide conjugation of a preformed CRISPR-Cas RNP complex or by peptide conjugation of a Cas protein engineered for site-selective conjugations followed by complexing with a guide RNA to form an RNP complex. Non-limiting examples include conjugates of short peptides of nuclear localization signal (NLS).

Another aspect of the invention is directed to a Cas protein-guide RNA complex conjugated with small molecule ligands of cell receptors, which are prepared by ligand conjugation of a preformed CRISPR-Cas RNP complex or by ligand conjugation of a Cas protein engineered for site-selective conjugations followed by complexing with a guide RNA to form a RNP complex. Non-limiting examples include asialoglycoprotein receptor ligands (ASGPrL) such as N-acetylgalactosamine (GalNAc) and lactobionic acid.

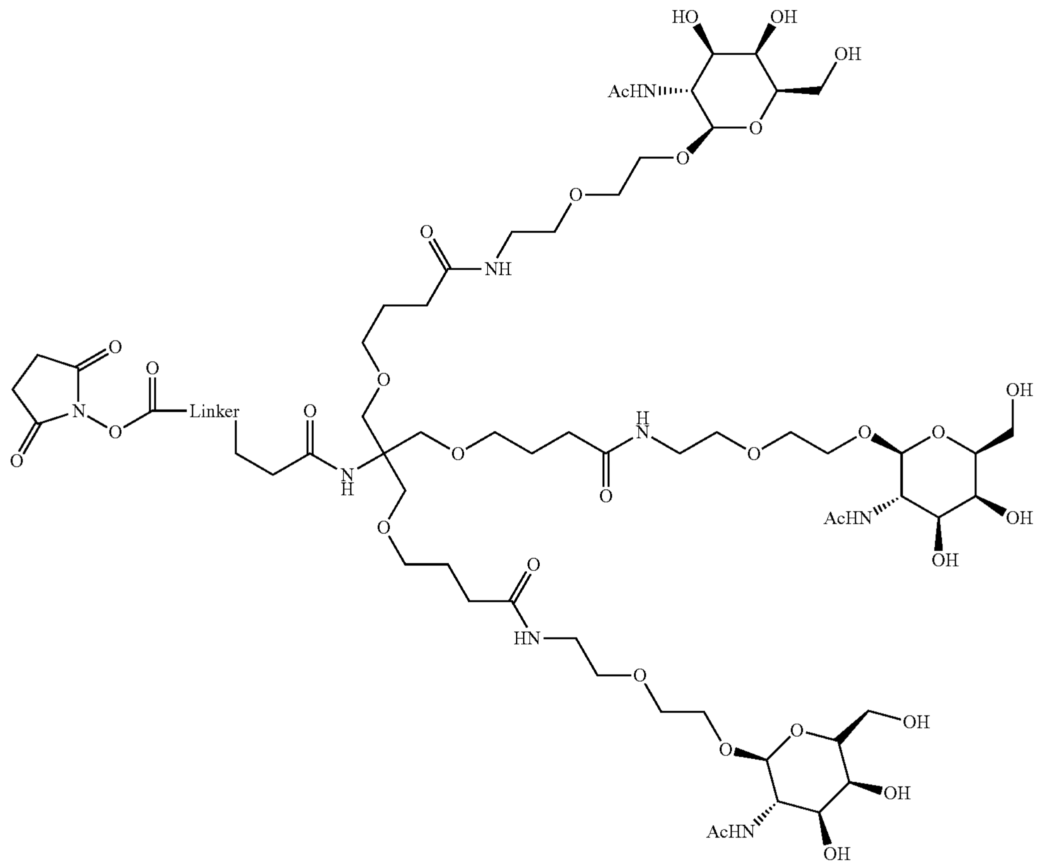

LIGAND-1

Yet another aspect of the invention is directed to a Cas protein-guide RNA complex conjugated with carbohydrates, which is prepared by carbohydrate conjugation of a pre-formed CRISPR-Cas RNP complex or by carbohydrate conjugation of a Cas protein engineered for site-selective conjugations followed by complexing with a guide RNA to form an RNP complex. Non-limiting examples include oligosaccharides and polysaccharides.

Yet another aspect of the invention is directed to conjugates of an engineered Cas9 protein mutated at C80 and incorporating one or more cysteines for site-selective conjugations by site-directed mutagenesis.

The present invention relates to compositions of conjugates of a guide RNA(s)-Cas protein (RNP) complex and their uses as medicinal agents in treatment of viral infectious diseases and as gene regulation, disruption and/or correction-based therapeutics. The conjugate(s) comprises a guide RNA-Cas protein (RNP) complex and one or more molecules selected from a group comprising PEG, non-PEG polymers, ligands for cellular receptors, lipids, oligonucleotides, antibodies, polysaccharides, glycans and peptides and chemically linked to a Cas protein and/or guide RNA(s).

The said uses may optionally include delivering an HDR template, wherein the template provides expression of a normal or less aberrant form of the protein to alleviate or eliminate a condition or disease state. The said HDR template may optionally be conjugated to guide RNA(s) and/or Cas protein.

Some aspects of the invention are directed to a donor template containing a "gene-editing-sequence" comprising one or more gene regulatory sequences or stop codons, and in some embodiments, the donor template(s) is conjugated to guide RNA(s) as part(s) of an lgRNA.

Some aspects of the invention are directed to PEGylated CRISPR-Cas9-lgRNA-conjugate and transfection reagent(s) systems.

Some aspects of the invention are directed to the use of conjugates of a guide RNA(s)-Cas protein (RNP) complex such as a PEGylated CRISPR-Cas9-lgRNA-conjugate system for antiviral therapy targeting against proviral DNAs or integrated viral DNA and episomal circular DNAs.

In some embodiments, non-limiting examples of targeted viral genomic sequences of HBV include:

(SEQ ID NO: 45)
ctctgctagatcccagagtg [aGG], (SEQ ID NO: 46)
gctatcgctggatgtgtctg [cGG], (SEQ ID NO: 47)
tggacttctctcaattttct [a[G[G]G]G]], (SEQ ID NO: 48)
gggggatcacccgtgtgtct [tGG], (SEQ ID NO: 49)
tatgtggatgatgtggtactgg [gGG], -continued

```
(SEQ ID NO: 50)
cctcaccatacagcactc [gGG],

(SEQ ID NO: 51)
gtgttggggtgagttgatgaatc [tGG],
```

wherein nucleotides in [ ] are PAMs, or any sequence of 17-20 nt immediately next to a PAM sequence.

In some embodiments, the therapeutic Cas9-lgRNA RNP conjugates comprise multiple lgRNAs targeting at different sites in viral genome (multiplex editing).

In some embodiments, multiple crgRNAs, including but not limited to sequences of YMDD and its mutations at catalytic domain of HBV polymerase, corresponding to

```
(SEQ ID NO: 52)
tatgtggatgat gtggtactgg [gGG],

(SEQ ID NO: 53)
tatatggatgat gtggtattgg [gGG],

(SEQ ID NO: 54)
tatgtggatgat gtggtattgg [gGG],

(SEQ ID NO: 55)
tatatagatgat gtggtactgg [gGG],
```

are ligated to tracrgRNA to result in a mixture of lgRNAs or lgRNA conjugates, and thus a mixture of Cas9-lgRNA RNP conjugates to target drug resistance in therapies based on direct-acting antiviral agents (DAA).

In some embodiments, non-limiting examples of targeted viral genomic sequences of HIV include:

```
(SEQ ID NO: 56)
gattggcaga actacacacc [aGG],

(SEQ ID NO: 57)
atcagatatc cactgacctt [tGG],

(SEQ ID NO: 58)
gcgtggcctg ggcgggactg [gGG],

(SEQ ID NO: 59)
cagcagttct tgaagtactc [cGG],
```

wherein nucleotides in [ ] are PAMs, or any sequence of 17-20 nt immediately next to a PAM sequence.

In some embodiments, non-limiting examples of targeted viral genomic sequences of herpesviridae virus such as HSV and EBV include:

```
(SEQ ID NO: 60)
gccctggaccaacccggccc [gGG],

(SEQ ID NO: 61)
ggccgctgccccgctccggg [tGG],

(SEQ ID NO: 62)
ggaagacaatgtgccgcca [tGG],

(SEQ ID NO: 63)
tctggaccagaaggctccgg [cGG],

(SEQ ID NO: 64)
gctgccgcggagggtgatga [cGG],

(SEQ ID NO: 65)
ggtggcccaccgggtccgct [gGG],

(SEQ ID NO: 66)
gtcctcgagggggccgtcgc [gGG],
```

wherein nucleotides in [ ] are PAMs, or any sequence of 17-20 nt immediately next to a PAM sequence.

In some embodiments, non-limiting examples of targeted genomic sequences include 17-20 nt of genes encoding endogenous T-cell receptors (TCR), HLA class I (HLA-I) or T-cell inhibitory receptors or signal molecules such as programmed cell death protein 1 (PD1) and cytotoxic T lymphocyte-associate protein 4 (CTLA4), immediately next to a PAM sequence.

Other aspects of the invention are directed to the use of said CRISPR-Cas-guide RNA conjugate systems for gene therapy and treatments of human infectious diseases.

In some embodiments, targeted sequences are human genomic sequences incorporating disease causing mutations, e.g.

```
(SEQ ID NO: 67)
5'-aaa gaa aat atm mmt ggt gtt-3',
```

wherein m is a mutation, and the "gene-editing-sequence" comprises

```
(SEQ ID NO: 68)
5'-aaa gaa aat ate ttt ggt gtt-3'.
```

Non-limiting examples of such human single-gene disorders are given below (Table 1). Other examples include human polygenic disorders such as heart disease and diabetes.

TABLE 1

Examples single-gene disorders and their prevalence

| Disorder | Prevalence (approximate) |
|---|---|
| Autosomal dominant | |
| Familial hypercholesterolemia | 1 in 500 |
| Polycystic kidney disease | 1 in 1250 |
| Neurofibromatosis type I | 1 in 2,500 |
| Hereditary spherocytosis | 1 in 5,000 |
| Marfan syndrome | 1 in 4,000 |
| Huntington's disease | 1 in 15,000 |
| Autosomal recessive | |
| Sickle cell anaemia | 1 in 625 |
| Cystic fibrosis | 1 in 2,000 |
| Tay-Sachs disease | 1 in 3,000 |
| Phenylketonuria | 1 in 12,000 |
| Mucopolysaccharidoses | 1 in 25,000 |
| Lysosomal acid lipase deficiency | 1 in 40,000 |
| Glycogen storage diseases | 1 in 50,000 |
| X-linked | |
| Duchenne muscular dystrophy | 1 in 7,000 |
| Hemophilia | 1 in 10,000 |

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates that may need to be independently confirmed.

This disclosure is not limited to particular embodiments described, as such may vary. It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

EXAMPLES

The following examples further illustrate embodiments of the disclosed invention, which are not limited by these examples.

Example 1

Synthesis of SaCas9 crRNA-GalNAc Conjugate (SEQ ID NO: 69)

5′ GCGUGGCCUG GGCGGGACUGGUUUU AGUAC UCUGU AAUUU UAGGU AUGAG

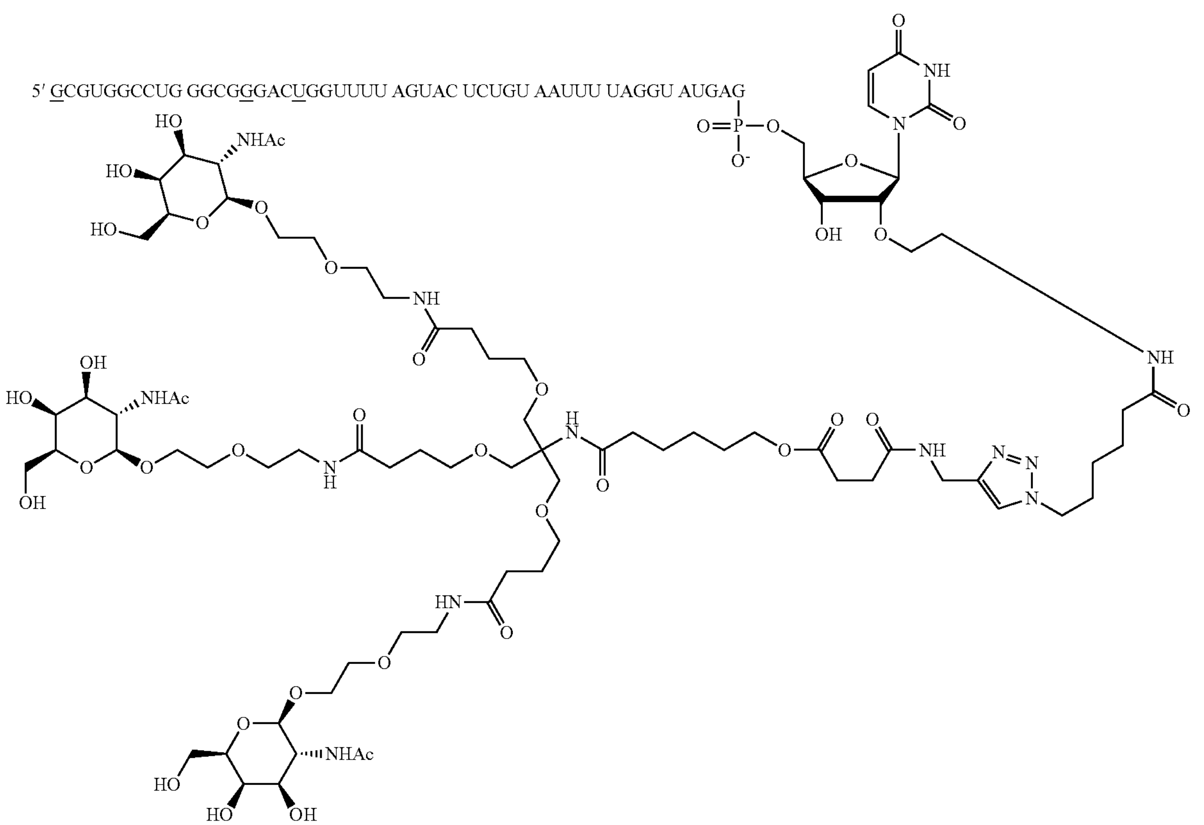

STEP 1. The 3'-amino-crRNA is prepared using 2'-TBS protected RNA phosphoramidite monomers with t-butylphenoxyacetyl protection of the A, G and C nucleobases and unprotected uracil. 0.3 M Benzylthiotetrazole in acetonitrile (Link Technologies) is used as the coupling agent, t-butylphenoxyacetic anhydride as the capping agent and 0.1 M iodine as the oxidizing agent. Oligonucleotide synthesis is carried out on an Applied Biosystems 394 automated DNA/RNA synthesizer using the standard 1.0 μmole RNA phosphoramidite cycle. Uridine on CPG is prepared as before (US20160215275A1) and packed into a twist column. All O-cyanoethyl phosphoramidite monomers are dissolved in anhydrous acetonitrile to a concentration of 0.1 M immediately prior to use. Stepwise coupling efficiencies are determined by automated trityl cation conductivity monitoring and in all cases are >97.5%.

Fmoc is then cleaved by treatment with 20% piperidine in DMF. The resulting 3'-end aminoethyl oligonucleotide is then treated with NHS ester of 6-azido caproic acid in DMF.

Cleavage of oligonucleotides from the solid support and deprotection are achieved by exposure to concentrated aqueous ammonia/ethanol (3/1 v/v) for 2 h at room temperature followed by heating in a sealed tube for 45 min at 55° C. and desilylation in 1.0 M TBAF in THF for 24 h to give 3'-azide-crRNA.

Alternatively, the step of reaction with NHS ester is skipped, and the above resulting fully deprotected oligonucleotide is dissolved in 0.5 M $Na_2CO_3$/$NaHCO_3$ buffer (pH 8.75) and incubated with succinimidyl-6-azidohexanate (20 eq.) in DMSO to give 3'-azide-crRNA.

STEP 2. To a solution of tri-GalNAc-alkyne and 3'-azide-crRNA (0.2 nmol of each) in 0.2 M NaCl (50 μL) at room temperature are added tris-hydroxypropyl triazole ligand (28 nmol in 42 μL 0.2 M NaCl), sodium ascorbate (40 nmol in 4 μL 0.2 M NaCl) and $CuSO_4.5H_2O$ (4 nmol in 4.0 μL 0.2

M NaCl), under argon. The reaction mixture is kept under argon at room temperature for the desired time, and formamide (50 μL) is added. The reaction is analyzed by loading directly onto a 20% polyacrylamide electrophoresis gel, and purified by reversed-phase HPLC to give the crRNA-tri-GalNAc conjugate.

Example 2: Cas9::crRNA-GalNAc::tracrRNA Complex

Cas9 Protein:

Recombinant Cas9 protein is available from New England BioLabs, Inc. and other providers or is expressed and purified from *E. coli* by a routinely used protocol (Anders, C. and Jinek, M. Methods Enzymol. 2014, 546, 1-20). The purity and concentration of Cas9 protein are analyzed by SDS-PAGE.

Cas9::crRNA-GalNAc::tracrRNA Complex:

tracrRNA is synthesized on an Applied Biosystems 394 automated DNA/RNA synthesizer as reported. Cas9, crRNA-GalNAc and tracrRNA are preincubated in a 1:5:5 molar ratio in the cleavage buffer to reconstitute the Cas9::crRNA-GalNAc::tracrRNA (RNP) complex.

Alternatively, tracrRNA is prepared by in vitro transcription at the presence of a RNA polymerase such as bacteriophage T7 RNA polymerase.

Example 3: PEGylation of CRISPR-Cas RNP Complex

The RNP (guide RNA-Cas protein) PEGylation is performed at different concentrations of m-PEG-pNP or m-PEG-NHS. RNP at 2 mg/mL in saline is incubated with varying concentrations of m-PEG-pNP or m-PEG-NHS (0.5, 1, 2, 4 and 6 mg/mL) in 1.5-mL microfuge tubes. The reaction is allowed to proceed at 30° C. for 3 hours. The PEGylated RNP complex(es) is used for in vitro DNA cleavages according to reported procedures without further purification.

Alternatively, before its storage at −80° C. or uses, size exclusion chromatography (SEC) of PEGylated RNP complex(es) is performed on a Akta Purifier using a HiLoad 16/60 S200 Superdex™ column with gel filtration buffer (20 mM HEPES pH 7.5, 150 mM KCl, 10% (v/v) glycerol) with a flow rate of 1 mL/min. PEGylated RNP complex(es) is loaded in volumes no greater than 1 mL.

Example 4: Expression and Purification of SpCas9 (Cys-SpCas9: M1C, C80A, S145C, S204C, S469C, S1159C)

SpCas9 expression plasmid containing amino acid substitutions are generated by standard PCR and molecular cloning.

The primers are synthesized on an Applied Biosystems 394 automated DNA/RNA synthesizer using the standard 1.0 μmole DNA phosphoramidite cycle. Nucleoside on CPG support is packed into a twist column. All β-cyanoethyl phosphoramidite monomers are dissolved in anhydrous acetonitrile to a concentration of 0.1 M immediately prior to use. Stepwise coupling efficiencies are determined by automated trityl cation conductivity monitoring and in all cases are >99%.

The Cys-SpCas9 is expressed in *E. coli* strain Rosetta 2 DE3 cells, and the protein is isolated and purified as described (Anders, et al. Methods Enzymol. 2014, 546, 1-20).

Example 5: PEGylation of Cys-SpCas9 Protein

PEGylation of Cys-SpCas9 protein is performed at different concentrations of m-PEG-Maleimide. Protein at 2 mg/mL in saline is incubated with varying concentrations of m-PEG-Maleimide (0.5, 1, 2, 4 and 6 mg/mL) in 1.5-mL microfuge tubes. The reaction is allowed to proceed at 30° C. for 3 hours.

Before its storage at −80° C. or uses, size exclusion chromatography (SEC) of PEGylated RNP complex(es) is performed on a Akta Purifier using a HiLoad 16/60 S200 Superdex™ column with gel filtration buffer (20 mM HEPES pH 7.5, 150 mM KCl, 10% (v/v) glycerol) with a flow rate of 1 mL/min. PEGylated RNP complex(es) is loaded in volumes no greater than 1 mL.

Example 6: Cys-SpCas9::lgRNA Complex

The PEGylated Cys-SpCas9 protein and lgRNA are preincubated in a 1:2 molar ratio in the cleavage buffer to reconstitute the Cas::lgRNA complex. The PEGylated RNP complex(es) is used for in vitro DNA cleavages according to reported procedures without further purification.

Example 7: ON-1 (SEQ ID NO: 70)

(SEQ ID NO: 70)

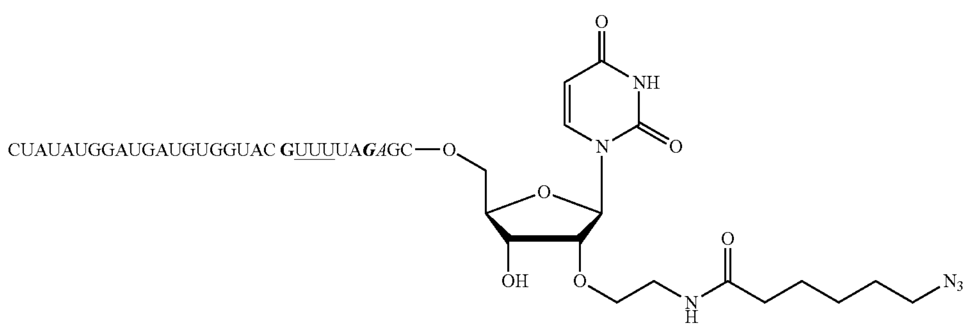

ON-1 is synthesized in a way similar to the synthesis of 3'-azide-crRNA in EXAMPLE 1, except the oligonucleotide is truncated at its 3'-end. The oligonucleotide is cleaved off the solid phase and fully deprotected, and purified as described in EXAMPLE 1.

Example 8: ON-2

(SEQ ID NO: 71)

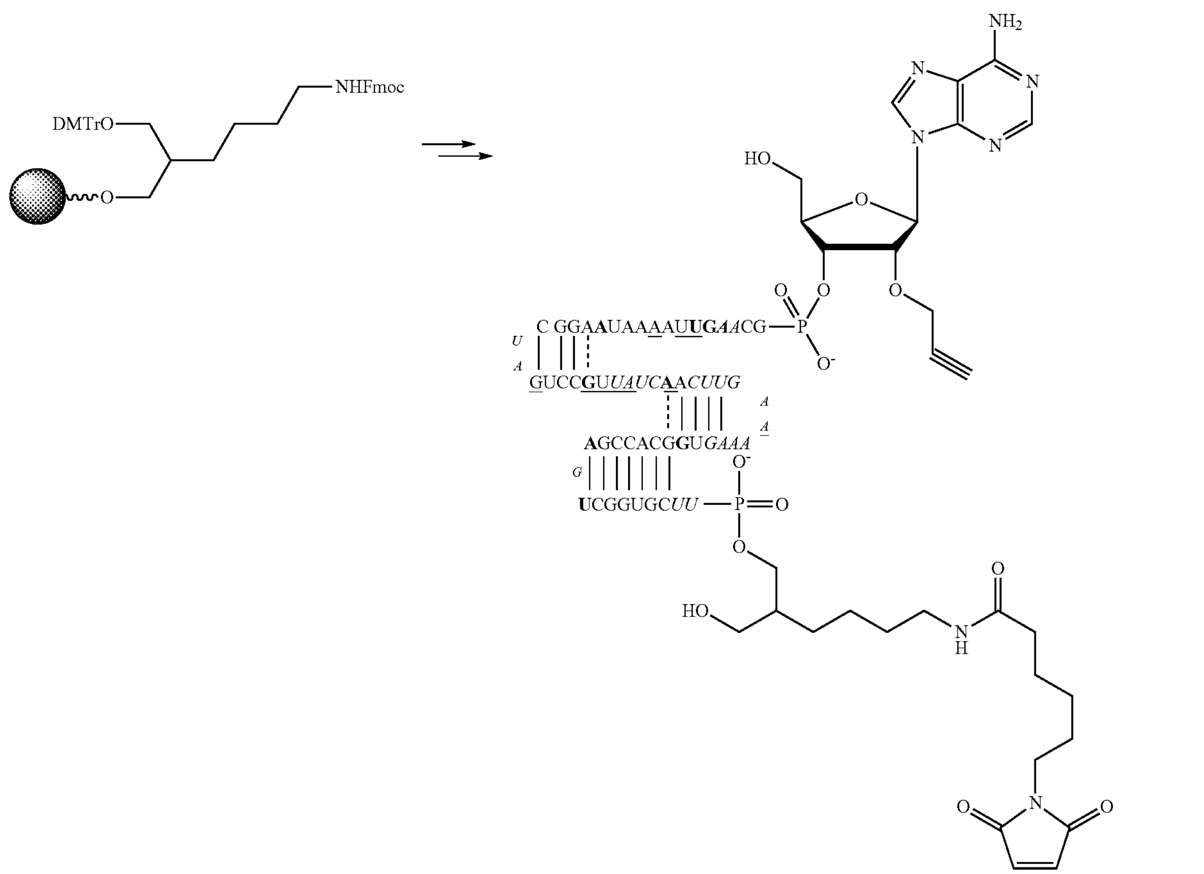

ON-2

ON-2 is synthesized in a way similar to the synthesis of ON-1, except that a solid phase support linked to Fmoc-hexylamine is used, and 2'-propargyl adenosine phosphoramidite is used to introduce an alkyne.

Fmoc is then cleaved by treatment with 20% piperidine in DMF. The resulting 3'-end aminohexyl oligonucleotide is then treated with NHS ester of 6-maleimide caproic acid in DMF.

Cleavage of oligonucleotides from the solid support and full deprotection are achieved by exposure to concentrated aqueous ammonia/ethanol (3/1 v/v) for 2 h at room temperature followed by heating in a sealed tube for 45 min at 55° C. and desilylation in 1.0 M TBAF in THF for 24 h.

Alternatively, the step of reaction with NHS ester is skipped, and the above resulting fully deprotected oligonucleotide is dissolved in 0.5 M $Na_2CO_3/NaHCO_3$ buffer (pH 8.75) and incubated with NHS ester of 6-maleimide caproic acid (20 eq.) in DMSO to give ON-2.

Example 9: ON-3 (SEQ ID NO: 72)

(SEQ ID NO: 72)

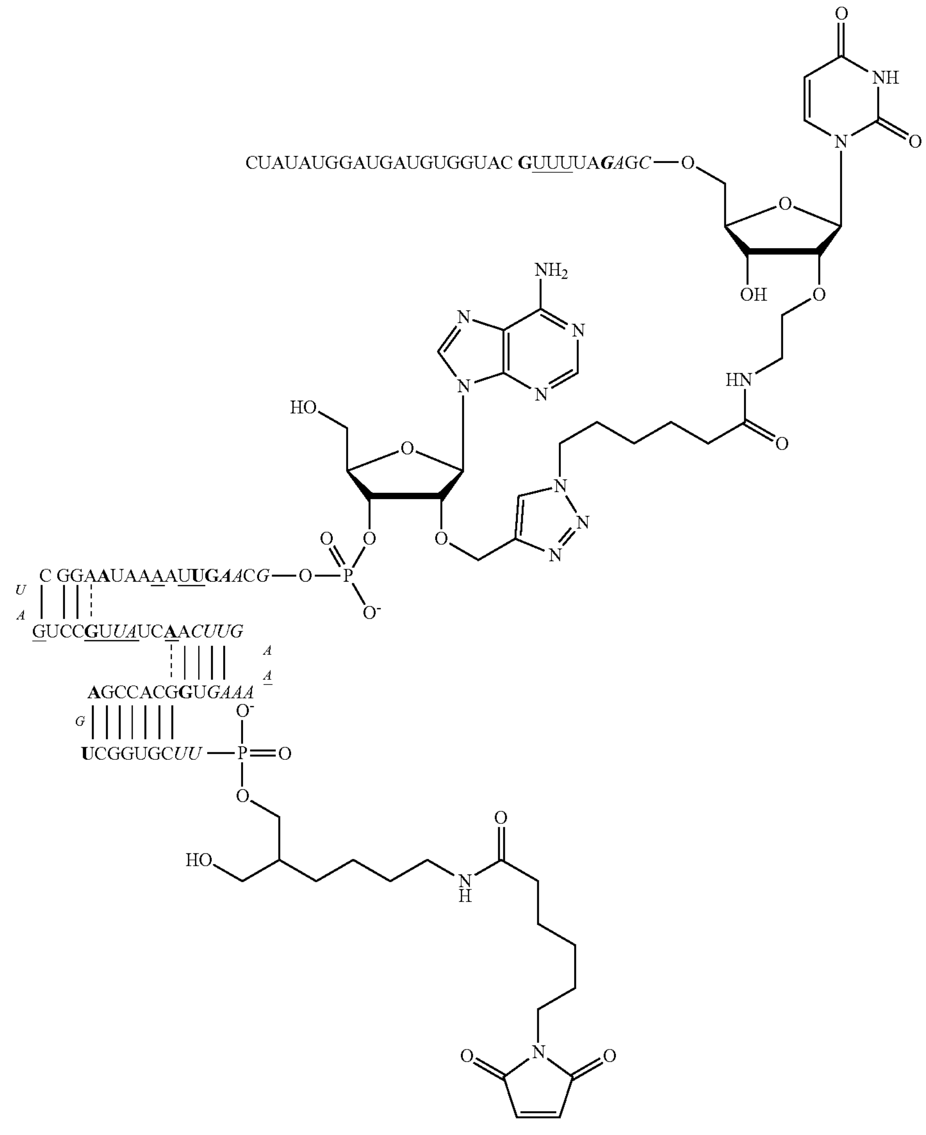

A solution of alkyne ON-1 and azide ON-2 (0.2 nmol of each) in 0.2 M NaCl (50 μL) is annealed for 30 min at room temperature. In the meantime, tris-hydroxypropyl triazole ligand (28 nmol in 42 μL 0.2 M NaCl), sodium ascorbate (40 nmol in 4 μL 0.2 M NaCl) and $CuSO_4.5H_2O$ (4 nmol in 4.0 μL 0.2 M NaCl), are added under argon. The reaction mixture is kept under argon at room temperature for the desired time, and formamide (50 L) is added. The reaction is analyzed by loading directly onto a 20% polyacrylamide electrophoresis gel, and purified by reversed-phase HPLC.

Example 10: ON-4 (SEQ ID NO: 73)
(SEQ ID NO: 73)
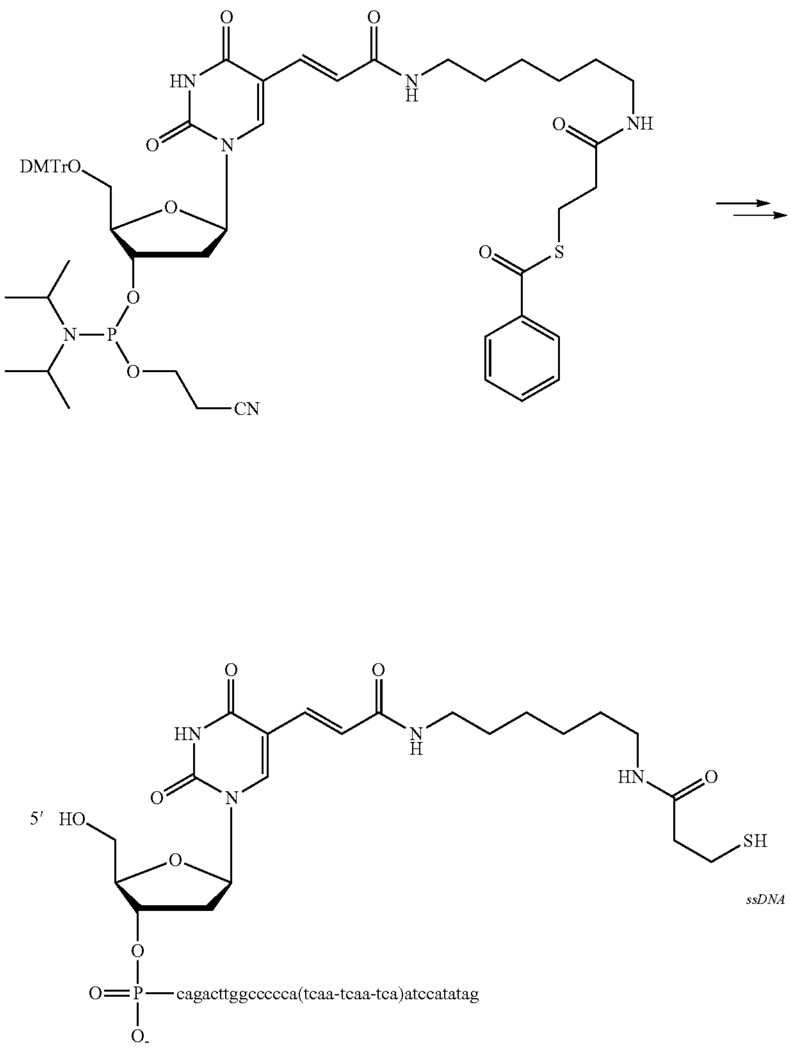
ON-4 is synthesized in a way similar to the synthesis of primers in Example 4.
Cleavage of oligonucleotides from the solid support and deprotection are achieved by exposure to concentrated aqueous ammonia/ethanol (3/1 v/v) for 2 h at room temperature followed by heating in a sealed tube for 45 min at 55° C.

Example 11: lgRNA(-3', 5'-)ssDNA (SEQ ID NO: 74) and sgRNA(-3', 5'-)ssDNA (SEQ ID NO: 75)
(SEQ ID NO: 74)
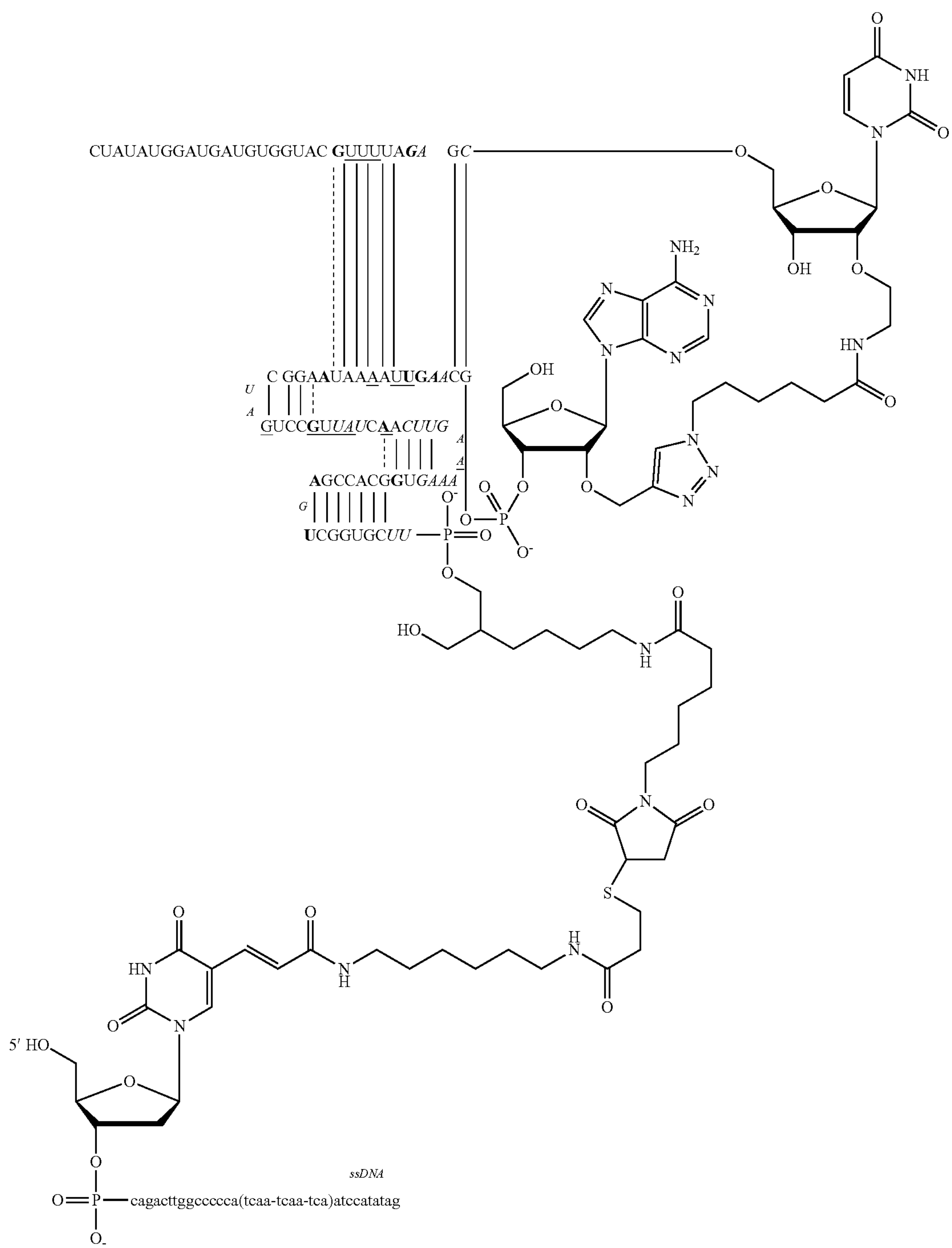
The ON-3 oligonucleotide carrying a maleimido group is incubated with 5'-SH-oligonucleotide (ON-4, 1:1 molar ratio) in 0.1 M triethylammonium acetate (TEAA) at pH 7.0 overnight at room temperature. The reaction mixture is analyzed and separated by HPLC to give the lgRNA-ssDNA.

(SEQ ID NO: 75)

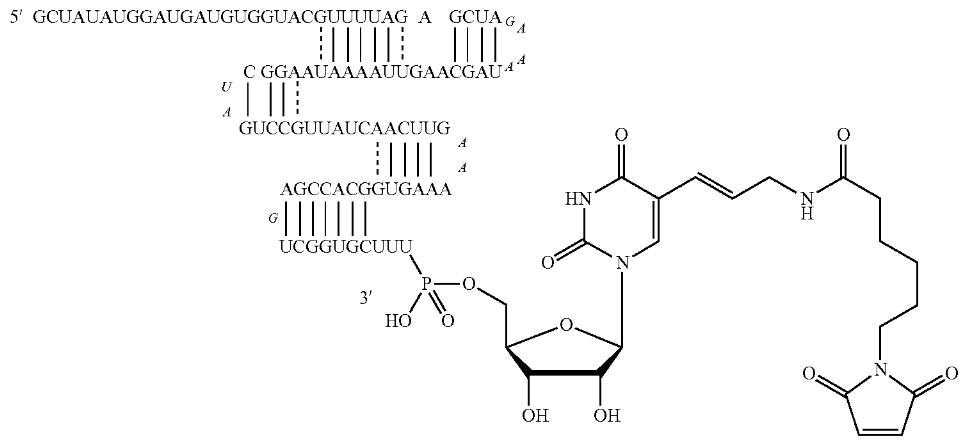

Alternatively, ON-3 oligonucleotide is substituted with an sgRNA carrying a maleimido group (ON-5 (SEQ ID NO: 75)) prepared from an sgRNA (incorporated an amine at its 3'-end) by enzymatic single nucleotide addition at the presence of a terminal deoxyribonucleotidyl transferase (TdT), followed by reacting the amine to introduce a maleimido group via NHS chemistry. The said amine at the 3'-end is incorporated from a uridine triphosphate analogue.

(SEQ ID NO: 76)

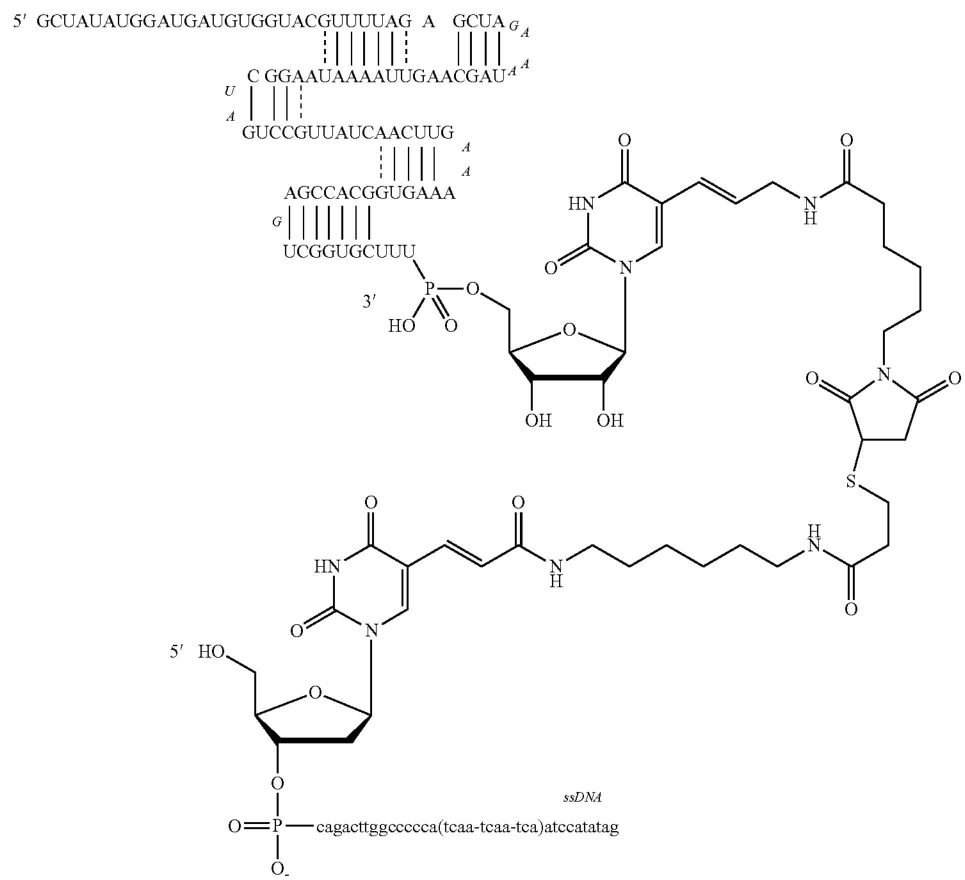

The ON-5 oligonucleotide carrying a maleimido group is incubated with 5'-SH-oligonucleotide (ON-4, 1:1 molar ratio) in 0.1 M triethylammonium acetate (TEAA) at pH 7.0 overnight at room temperature. The reaction mixture is analyzed and separated by HPLC to give the sgRNA-ssDNA.

Example 12: ssDNA(-3', 5'-)lgRNA (SEQ ID NO: 77)

The ssDNA oligonucleotide carrying a maleimido group at its 3'-end is incubated with the 5'-SH-lgRNA (1:1 molar ratio) in 0.1 M triethylammonium acetate (TEAA) at pH 7.0 overnight at room temperature. The reaction mixture is analyzed and separated by HPLC to give the lgRNA-ssDNA.

(SEQ ID NO: 77)

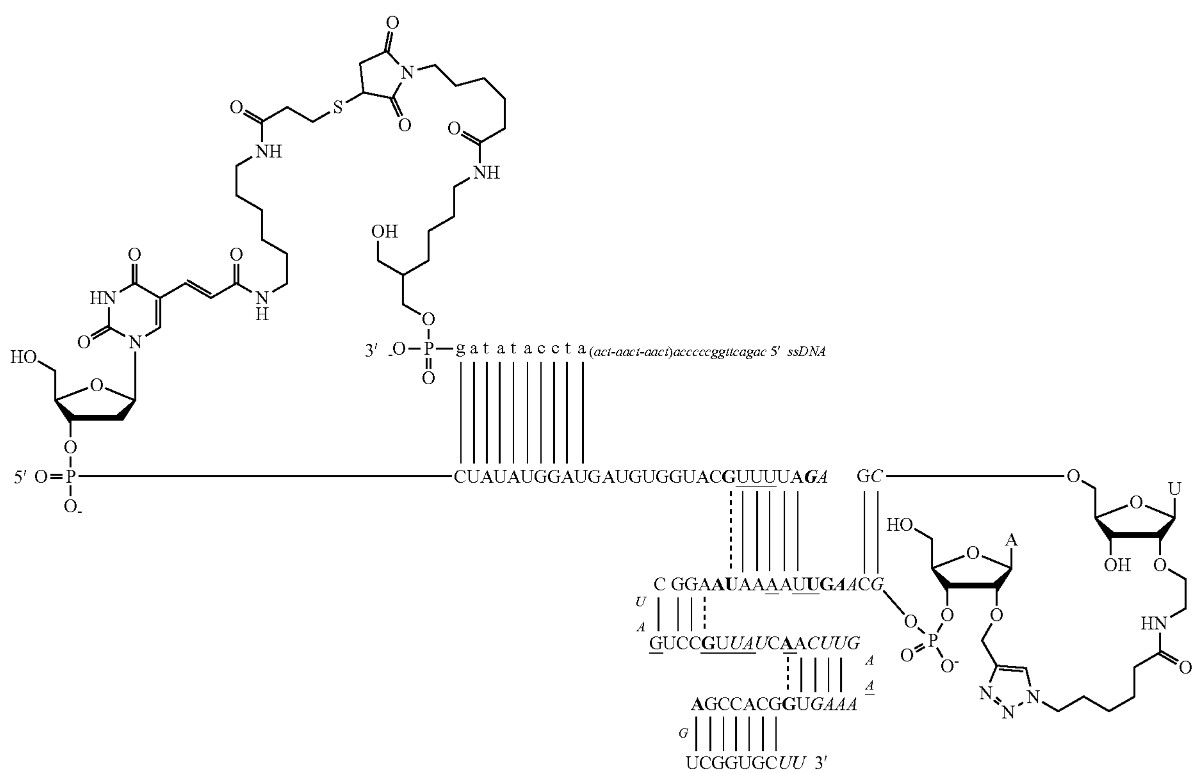

Example 13: lgRNA(-3', 5'-)ssDNA (SEQ ID NO: 78)

The RNA/DNA chimeric 5'-SH-tracrgRNA2-ssDNA oligonucleotide is synthesized on an Applied Biosystems 394 automated DNA/RNA synthesizer in a way similar to EXAMPLE 4 and 10. The tracrgRNA1 carrying a maleimido group at its 3'-end is synthesized in a way similar to the synthesis of ON-2 (SEQ ID NO: 71), and then ligated with ON-1 (SEQ ID NO: 70), as illustrated in EXAMPLE 9. The resulting oligonucleotide (crgRNA-tracrgRNA1) is incubated with the 5'-SH-tracrgRNA2-ssDNA (1:1 molar ratio) in 0.1 M triethylammonium acetate (TEAA) at pH 7.0 overnight at room temperature. The reaction mixture is analyzed and separated by HPLC to give the lgRNA-ssDNA.

(SEQ ID NO: 78)

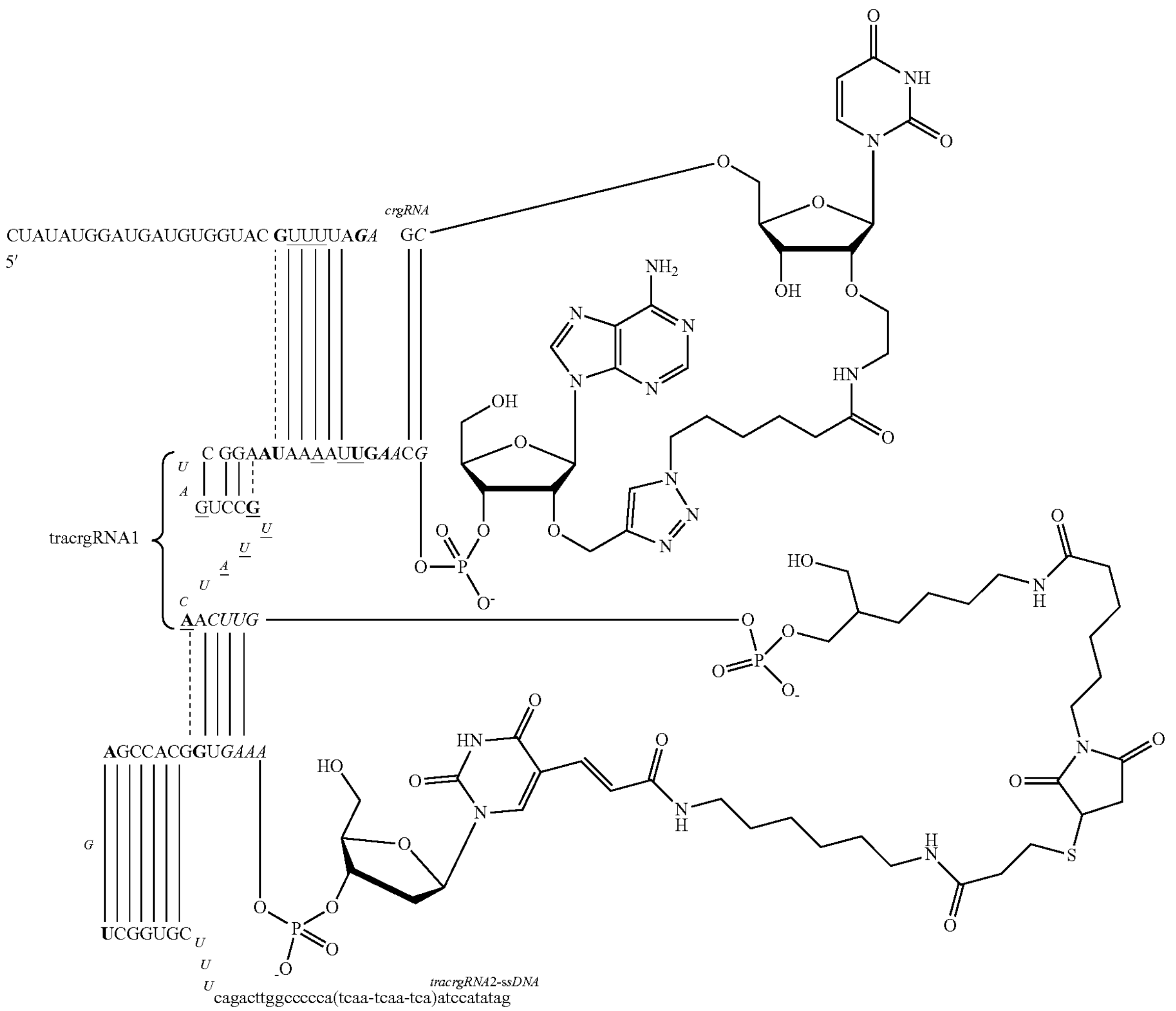

Example 14: Cys-SpCas9/lgRNA-ssDNA Complex

The PEGylated Cys-SpCas9 protein and lgRNA-ssDNA are preincubated in a 1:2 molar ratio in the cleavage buffer to reconstitute the Cas9/lgRNA-ssDNA complex. The PEGylated RNP complex(es) is used for DNA cleavages/editing according to reported procedures without further purification.

Example 15: Cys-SpCas9-Nickase (H840A)/lgRNA-ssDNA Complex

A Cys-SpCas9-nickase (H840A) conjugate and lgRNA-ssDNA are preincubated in a 1:2 molar ratio in the cleavage buffer to reconstitute the Cas9/lgRNA-ssDNA complex. The RNP complex(es) is used for DNA cleavages/editing according to reported procedures without further purification.

Example 16: Cellular Transfections, and Assays of Cas9/lgRNA-ssDNA a. Transfection with Cationic Lipids (Liu, D. Et al. Nature Biotechnology 2015, 33, 73-80):

Purified synthetic lgRNA-ssDNA or a mixture of synthetic lgRNA-ssDNAs is incubated with purified Cas9 protein for 5 min, and then complexed with the cationic lipid reagent in OPTIMEM media. The resulting mixture is applied to the cells for 4 h at 37° C.

b. Transfection with Cell-Penetrating Peptides (Kim, H. Et al. Genome Res. 2014, 24: 1012-1019):

Cell-penetrating peptide (CPP) is conjugated to a purified recombinant Cys-Cas9 protein by dropwise mixing of 1 mg Cas9 protein (2 mg/mL) with 50 μg 4-maleimidobutyryl-GGGRRRRRRRRRLLLL (SEQ ID NO: 83) (m9R; 2 mg/mL) in PBS (pH 7.4) followed by incubation on a rotator at room temperature for 2 h. To remove unconjugated m9R, the samples are dialyzed against DPBS (pH 7.4) at 4° C. for 24 h using 50 kDa molecular weight cutoff membranes. Cys-Cas9-m9R protein is collected from the dialysis membrane and the protein concentration is determined using the Bradford assay (Biorad).

Synthetic lgRNA-ssDNA or a mixture of synthetic lgRNA-ssDNAs is complexed with CPP: lgRNA-ssDNA (1 μg) in 1 μl of deionized water is gently added to the C3G9R4LC peptide (9R) in lgRNA:peptide weight ratios that range from 1:2.5 to 1:40 in 100 μl of DPBS (pH 7.4). This mixture is incubated at room temperature for 30 min and diluted 10-fold using RNase-free deionized water.

150 μl Cys-Cas9-m9R (2 M) protein is mixed with 100 μl lgRNA-ssDNA:9R (10:50 μg) complex and the resulting mixture is applied to the cells for 4 h at 37° C. Cells can also be treated with Cys-Cas9-m9R and lgRNA-ssDNA:9R sequentially.

Example 17: Anti-HBV in Cells

The antiviral assay is performed according to reported procedures (Hu, W. et al. Proc Natl Acad Sci USA 2014, 110: 11461-11466; Lin, Su. et al. Molecular Therapy—Nucleic Acids, 2014, 3, e186). Delivery to cell lines is either cationic lipid or CPP based delivery of Cys-Cas9/lgRNA-ssDNA complexes instead of plasmid transfection/transduction using gRNA/Cas9 expression vectors.

Alternatively, cells are treated with lgRNA-ssDNA and mRNA encoding Cas9 protein (lgRNA-ssDNA/mRNA-10:1) either as a mixture or sequentially in LNPs formulated with an amine-to-RNA-phosphate ratio of about 3-6 (N:P), or cells are treated with lgRNA-ssDNA in LNPs formulated with an amine-to-RNA-phosphate ratio of about 3-6 (N:P) and AAV vector encoding Cas9 protein.

Example 18: Anti-HBV in Chimeric Mice

The antiviral assay in HBV infected chimeric mice is performed according to a reported procedure except conjugates of Cys-Cas9/lgRNA-ssDNA RNP complexes are administrated instead of small interfering RNAs (Thi, E. P. et al. ACS Infec. Dis. 2019, 5, 725-737). All animals are bred under specific pathogen-free conditions in accordance with the ethical guidelines set forth by the National Institutes of Health for care of laboratory animals. The cDNA-uPA/SCID (cDNA-uPA (+/wt)/SCID (+/+)) hemizygote mice are generated as described. Cryopreserved human hepatocytes (2-year-old female, Hispanic, BD195, BD Biosciences) are transplanted into 2-4-week-old hemizygous cDNA-uPA/SCID mice via the spleen under anesthesia. The human hepatocytes are allowed to expand for 10-12 weeks and the replacement index are tested by measuring human albumin (h-Alb) in blood collected from tail vein using clinical chemistry analyzer (BioMajesty Series JCA-BM6050, JEOL Ltd.) with latex agglutination immunonephelometry (LZ Test "Eiken" U-ALB, Eiken Chemical Co., Ltd.). Male chimeric mice with more than 7.0 mg/mL h-Alb concentration in blood are judged as PXB mice whose replacement index is more than 70%.

PXB mice (>70% replacement index, 13-15 weeks old) are infected with HBV by intravenous injection through the tail vein with $1\times10^5$ copies of HBV containing serum from previously infected animals. Eight weeks post infection, animals with HBV DNA titers greater than $1.0\times10^6$ copies/mL and h-Alb greater than 7.0 mg/mL are selected (n=5 per group). Cys-Cas9/lgRNA-ssDNA complexes are dosed via the lateral tail vein in a volume of 0.2 mL per animal. Animals are euthanized at various time points by exsanguination under isoflurane anesthesia. Liver tissue is collected from the median or left lateral lobe from each animal for DNA extraction and for NGS. Editing efficiency and off-targets are determined as described (Finn, J. D. et al. Cell Reports 2018, 22, 2227-2235; Tsai, S. Q. et al. Nat. Methods 2017, 14, 607-614).

Blood is collected into serum separator tubes. Serum HBV DNA is assayed by qPCR and serum HBsAg measured by chemiluminescence enzyme immunoassay (ARCHITECT, Abbott). Serum HBeAg is also assessed using a chemiluminescence enzyme immunoassay (ARCHITECT, Abbott). Liver total and 3.5 kb HBV (pg)RNA at day 42 (study termination) are analyzed by Quantigene 2.0 b DNA assay (Affymetrix), and data is normalized to human glyceraldehyde-3-phosphate dehydrogenase (GAPDH) mRNA. Immunohistochemical analysis for HBcAg is conducted on liver sections at day 42.

Alternatively, lgRNA-ssDNA and mRNA encoding Cas9 protein (lgRNA-ssDNA/mRNA~10:1) are administrated either as a mixture or sequentially in LNPs formulated with an amine-to-RNA-phosphate ratio of about 3-6 (N:P), or AAV vector encoding Cas9 protein and lgRNA-ssDNA in LNPs formulated with an amine-to-RNA-phosphate ratio of about 3-6 (N:P) are administrated sequentially.

Example 19: Anti-HIV in Humanized Mice

The antiviral assay in HIV infected humanized mice is performed according to a reported procedure except Cys-Cas9/lgRNA-ssDNA RNP complexes are administrated instead of the AAV9-CRISPR-Cas9 vector (Dash, P. K. et al. Nat. Comm. 2019, 10, 1-20).

CD34+HSC are enriched from human cord blood or fetal liver cells using immune-magnetic beads. CD34+ cell purity was >90% by flow cytometry. Cells are transplanted into newborn mice irradiated at 1 Gy using a RS-2000×-Ray Irradiator by intrahepatic (i.h.) injection of 50,000 cells/mouse in 20 μl phosphate-buffered saline (PBS) with a 30-gauge needle. At 18 weeks of age, NSG-hu mice are infected intraperitoneally (i.p.) with HIV-$1_{NL4-3}$ at $10^4$ tissue culture infective $dose_{50}$ ($TCID_{50}$)/ml.

Cys-Cas9/lgRNA-ssDNA complexes are dosed via the lateral tail vein in a volume of 0.2 mL per animal. HIV-1 nucleic acids are detected by ddPCR and editing efficiency and off-targets are determined as described.

Alternatively, lgRNA-ssDNA and mRNA encoding Cas9 protein (ssDNA-lgRNA/mRNA-10:1) are administrated either as a mixture or sequentially in LNPs formulated with an amine-to-RNA-phosphate ratio of about 3-6 (N:P), or AAV vector encoding Cas9 protein and lgRNA-ssDNA in LNPs formulated with an amine-to-RNA-phosphate ratio of about 3-6 (N:P) are administrated sequentially.

Example 20: AAV-EFS_CMV::NLS-SaCas9-NLS-polyA; U6-tracrRNA Plasmid

```
5'-caccact tatac ctaaa attac agaat ctact aaaac
aaggc aaaat gccgt gttta tctcg tcaac ttgtt ggcga
gattt tt-3' (top, SEQ ID NO: 79)
```

-continued

```
5'-ggccaa aaatc tcgcc aacaa gttga cgaga taaac

acggc atttt gcctt gtttt agtag attct gtaat tttag

gtata agt-3' (bottom, SEQ ID NO: 80)
```

The top and bottom strands of oligonucleotides for cDNA encoding tracrRNA of SaCas9 system are synthesized using DNA phosphoramidite monomers with routine protection of the A, G and C nucleobases and unprotected thymine. 0.45 M tetrazole in acetonitrile is used as the coupling agent, acetic anhydride as the capping agent and 0.1 M iodine as the oxidizing agent. Oligonucleotide synthesis is carried out on an Applied Biosystems 394 automated DNA/RNA synthesizer using the standard 1.0 mole DNA phosphoramidite cycle. Nucleoside on CPG support is packed into a twist column. All (3-cyanoethyl phosphoramidite monomers are dissolved in anhydrous acetonitrile to a concentration of 0.1 M immediately prior to use. Stepwise coupling efficiencies are determined by automated trityl cation conductivity monitoring and in all cases are >99%.

Viral plasmids are produced utilizing standard recombinant DNA cloning techniques.

The above cDNA strands (1:1) are phosphorylated and annealed, and cloned into a linearized pX601-AAV-EFS_CMV::NLS-SaCas9-NLS-polyA3×HA-bGHpA; U6::BsaI-sgRNA expression plasmid vector (Addgene gene plasmid #61591) as following. The AAV vector is digested with BsaI and NotI to remove the insert of sgRNA scaffold, treated with antarctic phosphatase, and purified with a Quick nucleotide removal kit (QIAGEN). An equal amount of complementary oligonucleotide is mixed in T4 polynucleotide kinase (PNK) buffer for annealing. These annealed seed pairs are phosphorylated with T4 PNK and ligated into the BsaI- and NotI digested AAV using T7 DNA ligase.

Example 21: Virus Production

The AAV::SaCas9 virus is packaged using a triple plasmid transfection method as described (Chew, et al. Nature Methods, 2016). 293FT cells (Life Technologies) are plated in growth media consisting of DMEM+glutaMAX+pyruvate+10% FBS (Life Technologies), supplemented with 1×MEM non-essential amino acids (Gibco) in 150 mm plates. Confluency at transfection is between 70-90%, 20 μg of pHelper plasmid, 10 μg of pRepCap plasmid (encoding capsid proteins), and 10 μg of AAV plasmid carrying the construct of interest are mixed in 500 μL of DMEM, and 200 μg of PEI MAX® (Polysciences) (40 kDa, 1 mg/mL in H2O, pH 7.1) are added for PEI:DNA mass ratio of 5:1. The mixture is incubated for 15 minutes, and transferred dropwise to the cell media. The day after transfection, media is changed to DMEM+glutamax+pyruvate+2% FBS. Cells are harvested 48-72 hours after transfection by scrapping or dissociation with 1×PBS (pH7.2)+5 mM EDTA, and pelleted at 1500 g for 12 min. Cell pellets are resuspended in 1-5 mL of lysis buffer (Tris HCl pH 7.5+2 mM MgCl2+150 mM NaCl), and freeze-thawed 3× between dry-ice-ethanol bath and 37° C. water bath. Cell debris is clarified via 4000 g for 5 minutes, and the supernatant is collected.

The collected AAV supernatant is treated with 50 U/mL Benzonase and 1 U/mL Riboshredder™ for 30 minutes at 37° C. After incubation, the lysate is concentrated to <3 mL by ultrafiltration with Amicon® Ultra-15 (50 kDa MWCO) (Millipore), and loaded on top of a discontinuous density gradient consisting of 2 mL each of 15%, 25%, 40%, 60% OptiPrep™ (Sigma-Aldrich) in an 11.2 mL OptiSeal® polypropylene tube (Beckman-Coulter). The tubes are ultracentrifuged at 58000 rpm, at 18° C., for 1.5 hours, on an NVT65 rotor. The 40% fraction is extracted, and dialyzed with 1×PBS (pH 7.2) supplemented with 35 mM NaCl, using Amicon® Ultra-15 (50 kDa or 100 kDa MWCO) (Millipore). The purified AAVs are stored at −80° C. as 25 μL aliquots.

AAV titers (vector genomes) are quantified via hydrolysis probe qPCR against standard curves generated from linearized parental AAV plasmids.

Example 22: Generation of Cas9-tracrRNA Stable Cells and Transfection with crRNA(S)

Cells are plated at $2\times10^4$ per well in a 96-well plate in 100 μL of growth media. Purified AAVs are applied at confluency of 70-90%. Culture media is replaced with fresh growth media the next day, and the cells are incubated at 37° C. and 5% $CO_2$ for 24 hours. Culture media is replaced with fresh media, and the cells are transfected with crRNAs either gymnotically or with transfection reagents.

Example 23: Mice Injection

AAV vector and crRNAs are delivered to 5-6 week old male mice intravenously via lateral tail vein injection. All dosages of AAV are adjusted to 100 μL or 200 μL with sterile phosphate buffered saline (PBS), pH 7.4 (Gibco) before the injection.

Example 24: Generation of Inducible Cas9 Stable Cells and Transfection with lgRNA(s)

Cells are transduced with Edit-R Inducible Lentiviral hEF1α-Blast-Cas9 Nuclease Particles as detailed in the manufacturer's protocol. Cells are plated at $5\times10^4$ cells per well in a 24-well plate using Tet-free growth medium, incubated at 37° C. in a humidified $CO_2$ incubator overnight, and transduced with Edit-R Inducible Lentiviral hEF1α-Blast-Cas9 Nuclease. The incubation is continued for 4-6 hours, and the medium is replaced with Tet-free growth medium and the incubation is continued for 24-48 hours. Inducible Cas9 stable cells are selected in the medium with Tet-free selection medium containing the appropriate amount of blasticidin and expanded.

The selected inducible Cas9 stable cells are then induced in freshly prepared doxycycline solution for at least 24 hours. The cells are transfected using Lipofectamine™ RNAiMax and the lgRNA(s). The medium is replaced with fresh medium after 12 hours. Cells are then grown for 72 hours with the media replaced when necessary.

EQUIVALENTS

The present disclosure is not to be limited in terms of the particular embodiments described in this application, which are intended as single illustrations of individual aspects of the present disclosure. Many modifications and variations of this present disclosure can be made without departing from its spirit and scope, as will be apparent to those skilled in the art. Functionally equivalent methods and apparatuses within the scope of the present disclosure, in addition to those enumerated herein, will be apparent to those skilled in the art from the foregoing descriptions. Such modifications and variations are intended to fall within the scope of the present disclosure. It is to be understood that this present disclosure is not limited to particular methods, reagents, compounds compositions, or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 or 1 to 3 items refers to groups having 1, 2, or 3 items. Similarly, a group having 1-5 or 1 to 5 items refers to groups having 1, 2, 3, 4, or 5 items, and so forth.

All patents, patent applications, provisional applications, and publications referred to or cited herein are incorporated by reference in their entirety, including all figures and tables, to the extent they are not inconsistent with the explicit teachings of this specification.

```
DNA sequence of Cys-SpCas9 protein:
                                         (SEQ ID NO: 81)
  gacaagaagtacagcatcggcctggacatcggcaccaactctgtggg

ctgggccgtgatcaccgacgagtacaaggtgcccagcaagaaattcaagg

tgctgggcaacaccgaccggcacagcatcaagaagaacctgatcggagcc

ctgctgttcgacagcggcgaaacagccgaggccacccggctgaagagaac

cgccagaagaagatacaccagacggaagaaccggatc tatctgcaag

agatcttcagcaacgagatggccaaggtggacgacagcttcttccacaga

ctggaagagtccttcctggtggaagaggataagaagcacgagcggcaccc

catcttcggcaacatcgtggacgaggtggcctaccacgagaagtacccca

ccatctaccacctgagaaagaaactggtggac  accgacaaggccgac

ctgcggctgatctatctggccctggcccacatgatcaagttccggggcca

cttcctgatcgagggcgacctgaaccccgacaacagcgacgtggacaagc

tgttcatccagctggtgcagacctacaaccagctgttcgaggaaaacccc

atcaacgcc  ggcgtggacgccaaggccatcctgtctgccagactgag

caagagcagacggctggaaaatctgatcgcccagctgcccggcgagaaga

agaatggcctgttcggaaacctgattgccctgagcctgggcctgacccc
```

-continued

```
aacttcaagagcaacttcgacctggccgaggatgccaaactgcagctgag

caaggacacctacgacgacgacctggacaacctgctggcccagatcggcg

accagtacgccgacctgtttctggccgccaagaacctgtccgacgccatc

ctgctgagcgacatcctgagagtgaacaccgagatcaccaaggcccccct

gagcgcctctatgatcaagagatacgacgagcaccaccaggacctgaccc

tgctgaaagctctcgtgcggcagcagctgcctgagaagtacaaagagatt

ttcttcgaccagagcaagaacggctacgccggctacattgacggcggagc

cagccaggaagagttctacaagttcatcaagcccatcctggaaaagatgg

acggcaccgaggaactgctcgtgaagctgaacagagaggacctgctgcgg

aagcagcggaccttcgacaacggcagcatcccccaccagatccacctggg

agagctgcacgccattctgcggcggcaggaagatttttacccattcctga

aggacaaccgggaaaagatcgagaagatcctgaccttccgcatcccctac

tacgtgggccctctggccaggggaaacagcagattcgcctggatgaccag

aaag  gaggaaaccatcacccccctggaacttcgaggaagtggtggaca

agggcgcttccgcccagagcttcatcgagcggatgaccaacttcgataag

aacctgcccaacgagaaggtgctgcccaagcacagcctgctgtacgagta

cttcaccgtgtataacgagctgaccaaagtgaaatacgtgaccgagggaa

tgagaaagcccgccttcctgagcggcgagcagaaaaaggccatcgtggac

ctgctgttcaagaccaaccggaaagtgaccgtgaagcagctgaaagagga

ctacttcaagaaaatcgagtgcttcgactccgtggaaatctccggcgtgg

aagatcggttcaacgcctccctgggcacataccacgatctgctgaaaatt

atcaaggacaaggacttcctggacaatgaggaaaacgaggacattctgga

agatatcgtgctgaccctgacactgtttgaggacagagagatgatcgagg

aacggctgaaaacctatgcccacctgttcgacgacaaagtgatgaagcag

ctgaagcggcggagatacaccggctggggcaggctgagccggaagctgat

caacggcatccgggacaagcagtccggcaagacaatcctggatttcctga

agtccgacggcttcgccaacagaaacttcatgcagctgatccacgacgac

agcctgacctttaaagaggacatccagaaagcccaggtgtccggccaggg

cgatagcctgcacgagcacattgccaatctggccggcagccccgccatta

agaagggcatcctgcagacagtgaaggtggtggacgagctcgtgaaagtg

atgggccggcacaagcccgagaacatcgtgatcgaaatggccagagagaa

ccagaccacccagaagggacagaagaacagccgcgagagaatgaagcgga

tcgaagagggcatcaaagagctgggcagccagatcctgaaagaacacccc

gtggaaaacacccagctgcagaacgagaagctgtacctgtactacctgca

gaatgggcgggatatgtacgtggaccaggaactggacatcaaccggctgt

ccgactacgatgtggaccatatcgtgcctcagagctttctgaaggacgac

tccatcgacaacaaggtgctgaccagaagcgacaagaaccggggcaagag

cgacaacgtgccctccgaagaggtcgtgaagaagatgaagaactactggc

ggcagctgctgaacgccaagctgattacccagagaaagttcgacaatctg
```

-continued accaaggccgagagaggcggcctgagcgaactggataaggccggcttcat caagagacagctggtggaaacccggcagatcacaaagcacgtggcacaga tcctggactcccggatgaacactaagtacgacgagaatgacaagctgatc cgggaagtgaaagtgatcaccctgaagtccaagctggtgtccgatttccg gaaggatttccagttttacaaagtgcgcgagatcaacaactaccaccacg cccacgacgcctacctgaacgccgtcgtgggaaccgccctgatcaaaaag taccctaagctggaaagcgagttcgtgtacggcgactacaaggtgtacga cgtgcggaagatgatcgccaagagcgagcaggaaatcggcaaggctaccg ccaagtacttcttctacagcaacatcatgaactttttcaagaccgagatt accctggccaacggcgagatccggaagcggcctctgatcgagacaaacgg cgaaaccggggagatcgtgtgggataagggccgggattttgccaccgtgc ggaaagtgctgagcatgccccaagtgaatatcgtgaaaaagaccgaggtg cagacaggcggcttcagcaaagagtctatcctgcccaagaggaacagcga taagctgatcgccagaaagaaggactgggaccctaagaagtacggcggct tcgacagccccaccgtggcctattctgtgctggtggtggccaaagtggaa aagggcaagtccaagaaactgaag gtgaaagagctgctggggatcac catcatggaaagaagcagcttcgagaagaatcccatcgactttctggaag ccaagggctacaaagaagtgaaaaaggacctgatcatcaagctgcctaag tactccctgttcgagctggaaaacggccggaagagaatgctggcctctgc cggcgaactgcagaagggaaacgaactggccctgccctccaaatatgtga acttcctgtacctggccagccactatgagaagctgaagggctcccccgag gataatgagcagaaacagctgtttgtggaacagcacaagcactacctgga cgagatcatcgagcagatcagcgagttctccaagagagtgatcctggccg acgctaatctggacaaagtgctgtccgcctacaacaagcaccgggataag cccatcagagagcaggccgagaatatcatccacctgtttaccctgaccaa tctgggagcccctgccgccttcaagtactttgacaccaccatcgaccgga agaggtacaccagcaccaaagaggtgctggacgccaccctgatccaccag agcatcaccggcctgtacgagacacggatcgacctgtctcagctgggagg cgac -continued Sequence of Cys-SpCas9-NLS protein:

(SEQ ID NO: 82)

DKKYSIGLDIGTNSVGWAVITDEYKVPSKKFKVLGNTDRHSIKKNLIGA

LLFDSGETAEATRLKRTARRRYTRRKNRI YLQEIFSNEMAKVDDSFFHR

LEESFLVEEDKKHERHPIFGNIVDEVAYHEKYPTIYHLRKKLV STDKAD

LRLIYLALAHMIKFRGHFLIEGDLNPDNSDVDKLFIQLVQTYNQLFEENP

INA GVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRK EETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIE FDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLK VKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD*AYPYDVPDYASLGSGSPKKKRKVD*

SEQUENCE LISTING

<160> NUMBER OF SEQ ID NOS: 110

<210> SEQ ID NO 1
<211> LENGTH: 42
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: n is a, c, g, or u

<400> SEQUENCE: 1
nnnnnnnnnn nnnnnnnnnn guuuuagagc uaugcuguuu ug 42

-continued

```
<210> SEQ ID NO 2
<211> LENGTH: 81
<212> TYPE: RNA
<213> ORGANISM: Streptococcus pyogenes

<400> SEQUENCE: 2

ggaaccauuc aaaacagcau agcaaguuaa aauaaggcua guccguuauc aacuugaaaa     60

aguggcaccg agucggugcu u                                               81


<210> SEQ ID NO 3
<211> LENGTH: 94
<212> TYPE: RNA
<213> ORGANISM: Artificial Sequence
<220> FEATURE:
<223> OTHER INFORMATION: lgRNA, nn (32, 33) is either base-paired or
      not, and joined by non-nucleotide linker between the two, n32 (A)
      and n33 (B).
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (32)..(33)
<223> OTHER INFORMATION: n is a, c, g, or u

<400> SEQUENCE: 3

nnnnnnnnnn nnnnnnnnnn guuuuagagc unnagcaagu uaaaauaagg cuaguccguu     60

aucaacuuga aaaaguggca ccgagucggu gcuu                                 94


<210> SEQ ID NO 4
<211> LENGTH: 100
<212> TYPE: RNA
<213> ORGANISM: Artificial Sequence
<220> FEATURE:
<223> OTHER INFORMATION: sgRNA: crRNA and tracrRNA are fused as a single
      whole RNA by a tetraloop, gaaa.
<220> FEATURE:
<221> NAME/KEY: misc_feature
<222> LOCATION: (1)..(20)
<223> OTHER INFORMATION: n is a, c, g, or u

<400> SEQUENCE: 4

nnnnnnnnnn nnnnnnnnnn guuuuagagc uagaaauagc aaguuaaaau aaggcuaguc     60

cguuaucaac uugaaaaagu ggcaccgagu cggugcuuuu                          100


<210> SEQ ID NO 5
<211> LENGTH: 94
<212> TYPE: RNA
<213> ORGANISM: Artificial Sequence
<220> FEATURE:
<223> OTHER INFORMATION: lgRNA formed by two ligations between nn (32,
      33) of crgRNA and tracrgRNA, and between a70 and a71 in tracrgRNA.
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (32)..(33)
<223> OTHER INFORMATION: n is a, c, g, or u

<400> SEQUENCE: 5

nnnnnnnnnn nnnnnnnnnn guuuuagagc unnagcaagu uaaaauaagg cuaguccguu     60

aucaacuuga aaaaguggca ccgagucggu gcuu                                 94


<210> SEQ ID NO 6
```

<211> LENGTH: 94
<212> TYPE: RNA
<213> ORGANISM: Artificial Sequence
<220> FEATURE:
<223> OTHER INFORMATION: gRNA inserted with an aptamer between a32 and u33. The aptamer sequence is not shown.
<220> FEATURE:
<221> NAME/KEY: misc_feature
<222> LOCATION: (1)..(20)
<223> OTHER INFORMATION: n is a, c, g, or u

<400> SEQUENCE: 6
nnnnnnnnnn nnnnnnnnnn guuuuagagc uauagcaagu uaaaauaagg cuaguccguu 60
aucaacuuga aaaaguggca ccgagucggu gcuu 94

<210> SEQ ID NO 7
<211> LENGTH: 92
<212> TYPE: RNA
<213> ORGANISM: Artificial Sequence
<220> FEATURE:
<223> OTHER INFORMATION: gRNA inserted with two aptamers, positioned between a32 and u33 and between g69 and a70. The two aptamer sequences are not shown.
<220> FEATURE:
<221> NAME/KEY: misc_feature
<222> LOCATION: (1)..(20)
<223> OTHER INFORMATION: n is a, c, g, or u

<400> SEQUENCE: 7
nnnnnnnnnn nnnnnnnnnn guuuuagagc uauagcaagu uaaaauaagg cuaguccguu 60
aucaacuuga aaguggcacc gagucggugc uu 92

<210> SEQ ID NO 8
<211> LENGTH: 94
<212> TYPE: RNA
<213> ORGANISM: Artificial Sequence
<220> FEATURE:
<223> OTHER INFORMATION: lgRNA inserted with two chemically ligated aptamers by nNt-linkers, positioned between n32 and n33 and between a70 and a71. The two aptamer sequences are not shown.
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (32)..(33)
<223> OTHER INFORMATION: n is a, c, g, or u

<400> SEQUENCE: 8
nnnnnnnnnn nnnnnnnnnn guuuuagagc unnagcaagu uaaaauaagg cuaguccguu 60
aucaacuuga aaaaguggca ccgagucggu gcuu 94

<210> SEQ ID NO 9
<211> LENGTH: 62
<212> TYPE: RNA
<213> ORGANISM: Artificial Sequence
<220> FEATURE:
<223> OTHER INFORMATION: Chemically ligated tracrRNA inserted with two aptamers by nNt-linkers, positioned at 5'-end and n33 and between a38 and a39. The two aptamer sequences are not shown.
<220> FEATURE:
<221> NAME/KEY: misc_feature
<222> LOCATION: (1)..(1)
<223> OTHER INFORMATION: n is a, c, g, or u

<400> SEQUENCE: 9
nagcaaguua aaauaaggcu aguccguuau caacuugaaa aaguggcacc gagucggugc 60
uu 62

<210> SEQ ID NO 10
<211> LENGTH: 95
<212> TYPE: RNA
<213> ORGANISM: Artificial Sequence
<220> FEATURE:
<223> OTHER INFORMATION: lgRNA conjugated with a chemically ligated aptamer at u33 (modified) and joined by an nNt-linker positioned between u33 and n34. The aptamer sequence is not shown.
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (32)..(32)
<223> OTHER INFORMATION: n is a, c, g, or u
<220> FEATURE:
<221> NAME/KEY: misc_feature
<222> LOCATION: (34)..(34)
<223> OTHER INFORMATION: n is a, c, g, or u

<400> SEQUENCE: 10
nnnnnnnnnn nnnnnnnnnn guuuuagagc ununagcaag uuaaaauaag gcuaguccgu 60
uaucaacuug aaaaaguggc accgagucgg ugcuu 95

<210> SEQ ID NO 11
<211> LENGTH: 36
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: n is a, c, g, or u

<400> SEQUENCE: 11
nnnnnnnnnn nnnnnnnnnn guuuuagagc uaugcu 36

<210> SEQ ID NO 12
<211> LENGTH: 66
<212> TYPE: RNA
<213> ORGANISM: Streptococcus pyogenes

<400> SEQUENCE: 12
agcauagcaa guuaaaauaa ggcuaguccg uuaucaacuu gaaaaagugg caccgagucg 60
gugcuu 66

<210> SEQ ID NO 13
<211> LENGTH: 47
<212> TYPE: RNA
<213> ORGANISM: Artificial Sequence
<220> FEATURE:
<223> OTHER INFORMATION: lgRNA (partial sequence) formed by chemical ligation between tracrRNA and crRNA. The nNt-linker is positioned between c15 (3'-end of tracrRNA) and g16 (5'-end of crRNA).
<220> FEATURE:
<221> NAME/KEY: misc_feature
<222> LOCATION: (28)..(47)
<223> OTHER INFORMATION: n is a, c, g, or u

<400> SEQUENCE: 13
ggaagggaac ccuccggugg guuaaagnnn nnnnnnnnnn nnnnnnn 47

```
<210> SEQ ID NO 14
<211> LENGTH: 94
<212> TYPE: RNA
<213> ORGANISM: Artificial Sequence
<220> FEATURE:
<223> OTHER INFORMATION: lgRNA, nn (32, 33) is either base-paired or
      not, and joined by non-nucleotide linker between the two, n32 (A)
      and n33 (B). GalAc ligands are conjugated at 3'-end of lgRNA via a
      Linker.
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (32)..(33)
<223> OTHER INFORMATION: n is a, c, g, or u

<400> SEQUENCE: 14

nnnnnnnnnn nnnnnnnnnn guuuuagagc unnagcaagu uaaaauaagg cuaguccguu     60

aucaacuuga aaaaguggca ccgagucggu gcuu                                 94


<210> SEQ ID NO 15
<211> LENGTH: 47
<212> TYPE: RNA
<213> ORGANISM: Artificial Sequence
<220> FEATURE:
<223> OTHER INFORMATION: lgRNA (partial sequence) formed by chemical
      ligation between tracrRNA and crRNA. The nNt-linker of lgRNA is
      positioned between c15 (3'-end of tracrRNA) and g16 (5'-end of
      crRNA). GalAc ligands are conjugated at 3'-end of lgRNA via a
      second Linker.
<220> FEATURE:
<221> NAME/KEY: misc_feature
<222> LOCATION: (28)..(47)
<223> OTHER INFORMATION: n is a, c, g, or u

<400> SEQUENCE: 15

ggaagggaac ccuccggugg guuaaaagnnn nnnnnnnnnn nnnnnnn                   47


<210> SEQ ID NO 16
<211> LENGTH: 42
<212> TYPE: RNA
<213> ORGANISM: Artificial Sequence
<220> FEATURE:
<223> OTHER INFORMATION: Truncated crRNA with a general spacer.
<220> FEATURE:
<221> NAME/KEY: misc_feature
<222> LOCATION: (1)..(20)
<223> OTHER INFORMATION: n is a, c, g, or u

<400> SEQUENCE: 16

nnnnnnnnnn nnnnnnnnnn guuuuagagc uaugcuguuu ug                        42


<210> SEQ ID NO 17
<211> LENGTH: 81
<212> TYPE: RNA
<213> ORGANISM: Artificial Sequence
<220> FEATURE:
<223> OTHER INFORMATION: GalAc ligands are conjugated at 3'-end of
      tracrRNA via a Linker.

<400> SEQUENCE: 17

ggaaccauuc aaaacagcau agcaaguuaa aauaaggcua guccguuauc aacuugaaaa     60

aguggcaccg agucggugcu u                                               81


<210> SEQ ID NO 18
<211> LENGTH: 42
```

<212> TYPE: RNA
<213> ORGANISM: Artificial Sequence
<220> FEATURE:
<223> OTHER INFORMATION: A cholesterol is conjugated at 3'-end of crRNA
via a Linker.
<220> FEATURE:
<221> NAME/KEY: misc_feature
<222> LOCATION: (1)..(20)
<223> OTHER INFORMATION: n is a, c, g, or u

<400> SEQUENCE: 18
nnnnnnnnnn nnnnnnnnnn guuuuagagc uaugcuguuu ug 42

<210> SEQ ID NO 19
<211> LENGTH: 42
<212> TYPE: RNA
<213> ORGANISM: Artificial Sequence
<220> FEATURE:
<223> OTHER INFORMATION: Tocopherol is conjugated at 3'-end of crRNA via
a Linker.
<220> FEATURE:
<221> NAME/KEY: misc_feature
<222> LOCATION: (1)..(20)
<223> OTHER INFORMATION: n is a, c, g, or u

<400> SEQUENCE: 19
nnnnnnnnnn nnnnnnnnnn guuuuagagc uaugcuguuu ug 42

<210> SEQ ID NO 20
<211> LENGTH: 42
<212> TYPE: RNA
<213> ORGANISM: Artificial Sequence
<220> FEATURE:
<223> OTHER INFORMATION: An aptamer is conjugated at 3'-end of crRNA via
a Linker. The aptamer sequence is not shown.
<220> FEATURE:
<221> NAME/KEY: misc_feature
<222> LOCATION: (1)..(20)
<223> OTHER INFORMATION: n is a, c, g, or u

<400> SEQUENCE: 20
nnnnnnnnnn nnnnnnnnnn guuuuagagc uaugcuguuu ug 42

<210> SEQ ID NO 21
<211> LENGTH: 42
<212> TYPE: RNA
<213> ORGANISM: Artificial Sequence
<220> FEATURE:
<223> OTHER INFORMATION: An antibody is conjugated at 3'-end of crRNA
via a Linker. The amino acid sequence of the antibody is not
shown.
<220> FEATURE:
<221> NAME/KEY: misc_feature
<222> LOCATION: (1)..(20)
<223> OTHER INFORMATION: n is a, c, g, or u

<400> SEQUENCE: 21
nnnnnnnnnn nnnnnnnnnn guuuuagagc uaugcuguuu ug 42

<210> SEQ ID NO 22
<211> LENGTH: 25
<212> TYPE: DNA
<213> ORGANISM: Artificial Sequence
<220> FEATURE:
<223> OTHER INFORMATION: General scheme of a target DNA to be edited.
Its non-target strand is removed.
<220> FEATURE:
<221> NAME/KEY: misc_feature
<222> LOCATION: (1)..(20)
<223> OTHER INFORMATION: n is a, c, g, or t
<220> FEATURE:

-continued

<221> NAME/KEY: misc_feature
<222> LOCATION: (24)..(25)
<223> OTHER INFORMATION: n is a, c, g, or t

<400> SEQUENCE: 22
nnnnnnnnnn nnnnnnnnnn tggnn 25

<210> SEQ ID NO 23
<211> LENGTH: 43
<212> TYPE: RNA
<213> ORGANISM: Artificial Sequence
<220> FEATURE:
<223> OTHER INFORMATION: crRNA-ssDNA conjugate with a linker between n43 and ssDNA. The sequence of ssDNA is not shown.
<220> FEATURE:
<221> NAME/KEY: misc_feature
<222> LOCATION: (21)..(43)
<223> OTHER INFORMATION: n is a, c, g, or u

<400> SEQUENCE: 23
uaauuucuac uguuguagau nnnnnnnnnn nnnnnnnnnn nnn 43

<210> SEQ ID NO 24
<211> LENGTH: 43
<212> TYPE: RNA
<213> ORGANISM: Artificial Sequence
<220> FEATURE:
<223> OTHER INFORMATION: crRNA-ssDNA conjugate with a linker between ssDNA and u1. The sequence of ssDNA is not shown.
<220> FEATURE:
<221> NAME/KEY: misc_feature
<222> LOCATION: (1)..(23)
<223> OTHER INFORMATION: n is a, c, g, or u

<400> SEQUENCE: 24
nnnnnnnnnn nnnnnnnnnn nnnuaauuuc uacuguugua gau 43

<210> SEQ ID NO 25
<211> LENGTH: 43
<212> TYPE: RNA
<213> ORGANISM: Artificial Sequence
<220> FEATURE:
<223> OTHER INFORMATION: ssDNA_crRNA-ssDNA conjugate with a linker between ssDNA and u1 and a second linker between n43 and a second ssDNA. The sequences of both ssDNA's are not shown.
<220> FEATURE:
<221> NAME/KEY: misc_feature
<222> LOCATION: (21)..(43)
<223> OTHER INFORMATION: n is a, c, g, or u

<400> SEQUENCE: 25
uaauuucuac uguuguagau nnnnnnnnnn nnnnnnnnnn nnn 43

<210> SEQ ID NO 26
<211> LENGTH: 32
<212> TYPE: DNA
<213> ORGANISM: Artificial Sequence
<220> FEATURE:
<223> OTHER INFORMATION: crRNA-ssDNA conjugate with a linker between n32 and ssDNA. The sequence of ssDNA is not shown.
<220> FEATURE:
<221> NAME/KEY: misc_feature
<222> LOCATION: (1)..(20)
<223> OTHER INFORMATION: n is a, c, g, t or u
<220> FEATURE:
<221> NAME/KEY: misc_feature
<222> LOCATION: (32)..(32)
<223> OTHER INFORMATION: n is a, c, g, t or u

<400> SEQUENCE: 26
nnnnnnnnnn nnnnnnnnnn guuuuagagc un 32

<210> SEQ ID NO 27
<211> LENGTH: 67
<212> TYPE: DNA
<213> ORGANISM: Artificial Sequence
<220> FEATURE:
<223> OTHER INFORMATION: tracrRNA-ssDNA conjugate with a linker between ssDNA and n1, The sequence of ssDNA is not shown.
<220> FEATURE:
<221> NAME/KEY: misc_feature
<222> LOCATION: (1)..(1)
<223> OTHER INFORMATION: n is a, c, g, t or u

<400> SEQUENCE: 27
nagcauagca aguuaaaaua aggcuagucc guuaucaacu ugaaaaagug gcaccgaguc 60
ggugcuu 67

<210> SEQ ID NO 28
<211> LENGTH: 94
<212> TYPE: DNA
<213> ORGANISM: Artificial Sequence
<220> FEATURE:
<223> OTHER INFORMATION: lgRNA formed by two ligations between nn (32, 33) of crRNA and tracrRNA, and between a70 and a71 in tracrRNA. An ssDNA is conjugated at the ligation site between n32 and n33. The sequence of ssDNA is not shown.
<220> FEATURE:
<221> NAME/KEY: misc_feature
<222> LOCATION: (1)..(20)
<223> OTHER INFORMATION: n is a, c, g, t or u
<220> FEATURE:
<221> NAME/KEY: misc_feature
<222> LOCATION: (32)..(33)
<223> OTHER INFORMATION: n is a, c, g, t or u

<400> SEQUENCE: 28
nnnnnnnnnn nnnnnnnnnn guuuuagagc unnagcaagu uaaaauaagg cuaguccguu 60
aucaacuuga aaaaguggca ccgagucggu gcuu 94

<210> SEQ ID NO 29
<211> LENGTH: 94
<212> TYPE: DNA
<213> ORGANISM: Artificial Sequence
<220> FEATURE:
<223> OTHER INFORMATION: lgRNA formed by two ligations between nn (32, 33) of crRNA and tracrRNA, and between a70 and a71 in tracrRNA. An ssDNA is conjugated at the ligation site between n70 and n71. The sequence of ssDNA is not shown.
<220> FEATURE:
<221> NAME/KEY: misc_feature
<222> LOCATION: (1)..(20)
<223> OTHER INFORMATION: n is a, c, g, t or u
<220> FEATURE:
<221> NAME/KEY: misc_feature
<222> LOCATION: (32)..(33)
<223> OTHER INFORMATION: n is a, c, g, t or u

<400> SEQUENCE: 29
nnnnnnnnnn nnnnnnnnnn guuuuagagc unnagcaagu uaaaauaagg cuaguccguu 60
aucaacuuga aaaaguggca ccgagucggu gcuu 94

<210> SEQ ID NO 30
<211> LENGTH: 94
<212> TYPE: DNA
<213> ORGANISM: Artificial Sequence -continued
<220> FEATURE:
<223> OTHER INFORMATION: lgRNA formed by two ligations between nn (32, 33) of crRNA and tracrRNA, and between a70 and a71 in tracrRNA. An ssDNA is conjugated at the 3'-end (u94) of lgRNA via a nNt-Linker or nucleotide linker. The sequence of ssDNA is not shown.
<220> FEATURE:
<221> NAME/KEY: misc_feature
<222> LOCATION: (1)..(20)
<223> OTHER INFORMATION: n is a, c, g, t or u
<220> FEATURE:
<221> NAME/KEY: misc_feature
<222> LOCATION: (32)..(33)
<223> OTHER INFORMATION: n is a, c, g, t or u

<400> SEQUENCE: 30
nnnnnnnnnn nnnnnnnnnn guuuuagagc unnagcaagu uaaaauaagg cuaguccguu 60
aucaacuuga aaaaguggca ccgagucggu gcuu 94

<210> SEQ ID NO 31
<211> LENGTH: 61
<212> TYPE: DNA
<213> ORGANISM: Artificial Sequence
<220> FEATURE:
<223> OTHER INFORMATION: tracrRNA formed by ligation between a37 and a38. An ssDNA is conjugated at the 3'-end (u61) of tracrRNA via a nNt-Linker or nucleotide linker. The sequence of ssDNA is not shown.

<400> SEQUENCE: 31
agcaaguuaa aauaaggcua guccguuauc aacuugaaaa aguggcaccg agucggugcu 60
u 61

<210> SEQ ID NO 32
<211> LENGTH: 144
<212> TYPE: DNA
<213> ORGANISM: Artificial Sequence
<220> FEATURE:
<223> OTHER INFORMATION: lgRNA formed by two ligations between nn (82, 83) of crRNA and tracrRNA, and between a120 and a121 in tracrRNA. An ssDNA as an example is conjugated at the 5'-end of lgRNA via an nNt-Linker or nucleotide linker. The sequence of ssDNA is not shown.
<220> FEATURE:
<221> NAME/KEY: misc_feature
<222> LOCATION: (1)..(70)
<223> OTHER INFORMATION: n is a, c, g, t or u
<220> FEATURE:
<221> NAME/KEY: misc_feature
<222> LOCATION: (82)..(83)
<223> OTHER INFORMATION: n is a, c, g, t or u

<400> SEQUENCE: 32
nnnnnnnnnn nnnnnnnnnn nnnnnnnnnn nnnnnnnnnn nnnnnnnnnn nnnnnnnnnn 60
nnnnnnnnnn guuuuagagc unnagcaagu uaaaauaagg cuaguccguu aucaacuuga 120
aaaaguggca ccgagucggu gcuu 144

<210> SEQ ID NO 33
<211> LENGTH: 94
<212> TYPE: DNA
<213> ORGANISM: Artificial Sequence
<220> FEATURE:
<223> OTHER INFORMATION: lgRNA formed by two ligations between nn (32, 33) of crRNA and tracrRNA, and between a70 and a71 in tracrRNA. An ssDNA is conjugated at the 5'-end of lgRNA via a Linker. A second ssDNA is conjugated at the 3'-end of lgRNA.
<220> FEATURE:
<221> NAME/KEY: misc_feature
<222> LOCATION: (1)..(20)
<223> OTHER INFORMATION: n is a, c, g, t or u -continued
<220> FEATURE:
<221> NAME/KEY: misc_feature
<222> LOCATION: (32)..(33)
<223> OTHER INFORMATION: n is a, c, g, t or u

<400> SEQUENCE: 33
nnnnnnnnnn nnnnnnnnnn guuuuagagc unnagcaagu uaaaauaagg cuaguccguu 60
aucaacuuga aaaaguggca ccgagucggu gcuu 94

<210> SEQ ID NO 34
<211> LENGTH: 95
<212> TYPE: DNA
<213> ORGANISM: Artificial Sequence
<220> FEATURE:
<223> OTHER INFORMATION: lgRNA formed by two ligations between n34 of crRNA and n35 of tracrRNA, and between a71 and a72 in tracrRNA. An ssDNA is conjugated between the 3'-end of ssDNA and n1.
<220> FEATURE:
<221> NAME/KEY: misc_feature
<222> LOCATION: (1)..(20)
<223> OTHER INFORMATION: n is a, c, g, t or u
<220> FEATURE:
<221> NAME/KEY: misc_feature
<222> LOCATION: (32)..(32)
<223> OTHER INFORMATION: n is a, c, g, t or u
<220> FEATURE:
<221> NAME/KEY: misc_feature
<222> LOCATION: (34)..(34)
<223> OTHER INFORMATION: n is a, c, g, t or u

<400> SEQUENCE: 34
nnnnnnnnnn nnnnnnnnnn guuuuagagc ununagcaag uuaaaauaag gcuaguccgu 60
uaucaacuug aaaaaguggc accgagucgg ugcuu 95

<210> SEQ ID NO 35
<211> LENGTH: 95
<212> TYPE: RNA
<213> ORGANISM: Artificial Sequence
<220> FEATURE:
<223> OTHER INFORMATION: lgRNA formed by two ligations between u33 of crRNA and n34 of tracrRNA, and between a71 and a72 in tracrRNA. An ssDNA is conjugated at the ligation site between nn (32, 33) via a Linker between the 3'-end of ssDNA and u33.
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (32)..(32)
<223> OTHER INFORMATION: n is a, c, g, or u
<220> FEATURE:
<221> NAME/KEY: misc_feature
<222> LOCATION: (34)..(34)
<223> OTHER INFORMATION: n is a, c, g, or u

<400> SEQUENCE: 35
nnnnnnnnnn nnnnnnnnnn guuuuagagc ununagcaag uuaaaauaag gcuaguccgu 60
uaucaacuug aaaaaguggc accgagucgg ugcuu 95

<210> SEQ ID NO 36
<211> LENGTH: 144
<212> TYPE: DNA
<213> ORGANISM: Artificial Sequence
<220> FEATURE:
<223> OTHER INFORMATION: lgRNA formed by two ligations between nn (32, 33) of crRNA and tracrRNA, and between a70 and a71 in tracrRNA. An ssDNA is conjugated at the 3'-end of lgRNA via a triazole nNt-Linker between the 3'-end of lgRNA and the 5'-end of ssDNA.
<220> FEATURE:

```
<221> NAME/KEY: misc_feature
<222> LOCATION: (1)..(20)
<223> OTHER INFORMATION: n is a, c, g, t or u
<220> FEATURE:
<221> NAME/KEY: misc_feature
<222> LOCATION: (32)..(33)
<223> OTHER INFORMATION: n is a, c, g, t or u
<220> FEATURE:
<221> NAME/KEY: misc_feature
<222> LOCATION: (95)..(144)
<223> OTHER INFORMATION: n is a, c, g, t or u

<400> SEQUENCE: 36

nnnnnnnnnn nnnnnnnnnn guuuuagagc unnagcaagu uaaaauaagg cuaguccguu     60

aucaacuuga aaaaguggca ccgagucggu gcuunnnnnn nnnnnnnnnn nnnnnnnnnn    120

nnnnnnnnnn nnnnnnnnnn nnnn                                           144


<210> SEQ ID NO 37
<211> LENGTH: 95
<212> TYPE: DNA
<213> ORGANISM: Artificial Sequence
<220> FEATURE:
<223> OTHER INFORMATION: lgRNA formed by two ligations between u33 of
      crRNA and n34 of tracrRNA, and between a71 and a72 in tracrRNA. An
      ssDNA is conjugated at the ligation site between nn (32, 33) via
      an nNt-Linker between the 5'-end of ssDNA and u33.
<220> FEATURE:
<221> NAME/KEY: misc_feature
<222> LOCATION: (1)..(20)
<223> OTHER INFORMATION: n is a, c, g, t or u
<220> FEATURE:
<221> NAME/KEY: misc_feature
<222> LOCATION: (32)..(32)
<223> OTHER INFORMATION: n is a, c, g, t or u
<220> FEATURE:
<221> NAME/KEY: misc_feature
<222> LOCATION: (34)..(34)
<223> OTHER INFORMATION: n is a, c, g, t or u

<400> SEQUENCE: 37

nnnnnnnnnn nnnnnnnnnn guuuuagagc ununagcaag uuaaaauaag gcuaguccgu     60

uaucaacuug aaaaaguggc accgagucgg ugcuu                                95


<210> SEQ ID NO 38
<211> LENGTH: 43
<212> TYPE: RNA
<213> ORGANISM: Artificial Sequence
<220> FEATURE:
<223> OTHER INFORMATION: crRNA-ssDNA conjugate with an nNt-linker
      between n43 and the 5'-end of ssDNA.
<220> FEATURE:
<221> NAME/KEY: misc_feature
<222> LOCATION: (21)..(43)
<223> OTHER INFORMATION: n is a, c, g, or u

<400> SEQUENCE: 38

uaauuucuac uguuguagau nnnnnnnnnn nnnnnnnnnn nnn                       43


<210> SEQ ID NO 39
<211> LENGTH: 43
<212> TYPE: DNA
<213> ORGANISM: Artificial Sequence
<220> FEATURE:
<223> OTHER INFORMATION: crRNA-ssDNA conjugate with an nNt-linker
      between u1 and the 5'-end of ssDNA.
<220> FEATURE:
<221> NAME/KEY: misc_feature
<222> LOCATION: (21)..(43)
<223> OTHER INFORMATION: n is a, c, g, t or u
```

<400> SEQUENCE: 39
uaauuucuac uguuguagau nnnnnnnnnn nnnnnnnnnn nnn 43

<210> SEQ ID NO 40
<211> LENGTH: 43
<212> TYPE: DNA
<213> ORGANISM: Artificial Sequence
<220> FEATURE:
<223> OTHER INFORMATION: crRNA-ssDNA conjugate with an nNt-linker between n43 and the 3'-end of ssDNA.
<220> FEATURE:
<221> NAME/KEY: misc_feature
<222> LOCATION: (21)..(43)
<223> OTHER INFORMATION: n is a, c, g, t or u

<400> SEQUENCE: 40
uaauuucuac uguuguagau nnnnnnnnnn nnnnnnnnnn nnn 43

<210> SEQ ID NO 41
<211> LENGTH: 43
<212> TYPE: DNA
<213> ORGANISM: Artificial Sequence
<220> FEATURE:
<223> OTHER INFORMATION: crRNA-ssDNA conjugate with an nNt-linker between u1 and the 3'-end of ssDNA.
<220> FEATURE:
<221> NAME/KEY: misc_feature
<222> LOCATION: (21)..(43)
<223> OTHER INFORMATION: n is a, c, g, t or u

<400> SEQUENCE: 41
uaauuucuac uguuguagau nnnnnnnnnn nnnnnnnnnn nnn 43

<210> SEQ ID NO 42
<211> LENGTH: 43
<212> TYPE: DNA
<213> ORGANISM: Artificial Sequence
<220> FEATURE:
<223> OTHER INFORMATION: ssDNA-crRNA-ssDNA conjugate with an nNt-linker between u1 and the 3'-end of ssDNA, and a second nNt-linker between n43 and the 5'-end of a second ssDNA.
<220> FEATURE:
<221> NAME/KEY: misc_feature
<222> LOCATION: (21)..(43)
<223> OTHER INFORMATION: n is a, c, g, t or u

<400> SEQUENCE: 42
uaauuucuac uguuguagau nnnnnnnnnn nnnnnnnnnn nnn 43

<210> SEQ ID NO 43
<211> LENGTH: 194
<212> TYPE: DNA
<213> ORGANISM: Artificial Sequence
<220> FEATURE:
<223> OTHER INFORMATION: An ssDNA (n145 to n194) is conjugated at the 3'-end of lgRNA via a triazole nNt-Linker between the 3'-end of lgRNA and the 5'-end of ssDNA, and a second ssDNA s conjugated at the 5'-end of lgRNA.
<220> FEATURE:
<221> NAME/KEY: misc_feature
<222> LOCATION: (1)..(70)
<223> OTHER INFORMATION: n is a, c, g, t or u
<220> FEATURE:
<221> NAME/KEY: misc_feature
<222> LOCATION: (82)..(83)
<223> OTHER INFORMATION: n is a, c, g, t or u
<220> FEATURE:
<221> NAME/KEY: misc_feature
<222> LOCATION: (145)..(194)
<223> OTHER INFORMATION: n is a, c, g, t or u -continued

<400> SEQUENCE: 43
nnnnnnnnnn nnnnnnnnnn nnnnnnnnnn nnnnnnnnnn nnnnnnnnnn nnnnnnnnnn 60
nnnnnnnnnn guuuuagagc unnagcaagu uaaaauaagg cuaguccguu aucaacuuga 120
aaaaguggca ccgagucggu gcuunnnnnn nnnnnnnnnn nnnnnnnnnn nnnnnnnnnn 180
nnnnnnnnnn nnnn 194

<210> SEQ ID NO 44
<211> LENGTH: 144
<212> TYPE: DNA
<213> ORGANISM: Artificial Sequence
<220> FEATURE:
<223> OTHER INFORMATION: An ssDNA is conjugated at the 3'-end of lgRNA via a triazole nNt-Linker between the 3'-end of lgRNA and a dsDNA. Its complementary strand is not shown.
<220> FEATURE:
<221> NAME/KEY: misc_feature
<222> LOCATION: (1)..(20)
<223> OTHER INFORMATION: n is a, c, g, t or u
<220> FEATURE:
<221> NAME/KEY: misc_feature
<222> LOCATION: (32)..(33)
<223> OTHER INFORMATION: n is a, c, g, t or u
<220> FEATURE:
<221> NAME/KEY: misc_feature
<222> LOCATION: (95)..(144)
<223> OTHER INFORMATION: n is a, c, g, t or u

<400> SEQUENCE: 44
nnnnnnnnnn nnnnnnnnnn guuuuagagc unnagcaagu uaaaauaagg cuaguccguu 60
aucaacuuga aaaaguggca ccgagucggu gcuunnnnnn nnnnnnnnnn nnnnnnnnnn 120
nnnnnnnnnn nnnnnnnnnn nnnn 144

<210> SEQ ID NO 45
<211> LENGTH: 23
<212> TYPE: DNA
<213> ORGANISM: HBV

<400> SEQUENCE: 45
ctctgctaga tcccagagtg agg 23

<210> SEQ ID NO 46
<211> LENGTH: 23
<212> TYPE: DNA
<213> ORGANISM: HBV

<400> SEQUENCE: 46
gctatcgctg gatgtgtctg cgg 23

<210> SEQ ID NO 47
<211> LENGTH: 25
<212> TYPE: DNA
<213> ORGANISM: HBV

<400> SEQUENCE: 47
tggacttctc tcaattttct agggg 25

<210> SEQ ID NO 48
<211> LENGTH: 23
<212> TYPE: DNA
<213> ORGANISM: HBV

<400> SEQUENCE: 48
gggggatcac ccgtgtgtct tgg 23

<210> SEQ ID NO 49
<211> LENGTH: 25
<212> TYPE: DNA
<213> ORGANISM: HBV

<400> SEQUENCE: 49
tatgtggatg atgtggtact ggggg 25

<210> SEQ ID NO 50
<211> LENGTH: 21
<212> TYPE: DNA
<213> ORGANISM: HBV

<400> SEQUENCE: 50
cctcaccata cagcactcgg g 21

<210> SEQ ID NO 51
<211> LENGTH: 26
<212> TYPE: DNA
<213> ORGANISM: HBV

<400> SEQUENCE: 51
gtgttggggt gagttgatga atctgg 26

<210> SEQ ID NO 52
<211> LENGTH: 25
<212> TYPE: DNA
<213> ORGANISM: HBV

<400> SEQUENCE: 52
tatgtggatg atgtggtact ggggg 25

<210> SEQ ID NO 53
<211> LENGTH: 25
<212> TYPE: DNA
<213> ORGANISM: HBV

<400> SEQUENCE: 53
tatatggatg atgtggtatt ggggg 25

<210> SEQ ID NO 54
<211> LENGTH: 25
<212> TYPE: DNA
<213> ORGANISM: HBV

<400> SEQUENCE: 54
tatgtggatg atgtggtatt ggggg 25

<210> SEQ ID NO 55
<211> LENGTH: 25
<212> TYPE: DNA
<213> ORGANISM: HBV

<400> SEQUENCE: 55
tatatagatg atgtggtact ggggg 25

<210> SEQ ID NO 56
<211> LENGTH: 23
<212> TYPE: DNA
<213> ORGANISM: HIV

<400> SEQUENCE: 56
gattggcaga actacacacc agg 23

<210> SEQ ID NO 57
<211> LENGTH: 23
<212> TYPE: DNA
<213> ORGANISM: HIV

<400> SEQUENCE: 57
atcagatatc cactgacctt tgg 23

<210> SEQ ID NO 58
<211> LENGTH: 23
<212> TYPE: DNA
<213> ORGANISM: HIV

<400> SEQUENCE: 58
gcgtggcctg ggcgggactg ggg 23

<210> SEQ ID NO 59
<211> LENGTH: 23
<212> TYPE: DNA
<213> ORGANISM: HIV

<400> SEQUENCE: 59
cagcagttct tgaagtactc cgg 23

<210> SEQ ID NO 60
<211> LENGTH: 23
<212> TYPE: DNA
<213> ORGANISM: EBV

<400> SEQUENCE: 60
gccctggacc aacccggccc ggg 23

<210> SEQ ID NO 61
<211> LENGTH: 23
<212> TYPE: DNA
<213> ORGANISM: EBV

<400> SEQUENCE: 61
ggccgctgcc ccgctccggg tgg 23

<210> SEQ ID NO 62
<211> LENGTH: 22
<212> TYPE: DNA
<213> ORGANISM: EBV

<400> SEQUENCE: 62
ggaagacaat gtgccgccat gg 22

<210> SEQ ID NO 63
<211> LENGTH: 23
<212> TYPE: DNA
<213> ORGANISM: EBV

<400> SEQUENCE: 63
tctggaccag aaggctccgg cgg 23

<210> SEQ ID NO 64
<211> LENGTH: 23
<212> TYPE: DNA

<213> ORGANISM: EBV

<400> SEQUENCE: 64
gctgccgcgg agggtgatga cgg 23

<210> SEQ ID NO 65
<211> LENGTH: 23
<212> TYPE: DNA
<213> ORGANISM: EBV

<400> SEQUENCE: 65
ggtggcccac cgggtccgct ggg 23

<210> SEQ ID NO 66
<211> LENGTH: 23
<212> TYPE: DNA
<213> ORGANISM: EBV

<400> SEQUENCE: 66
gtcctcgagg gggccgtcgc ggg 23

<210> SEQ ID NO 67
<211> LENGTH: 21
<212> TYPE: DNA
<213> ORGANISM: human

<400> SEQUENCE: 67
aaagaaaata tmmmtggtgt t 21

<210> SEQ ID NO 68
<211> LENGTH: 21
<212> TYPE: DNA
<213> ORGANISM: human

<400> SEQUENCE: 68
aaagaaaata tctttggtgt t 21

<210> SEQ ID NO 69
<211> LENGTH: 50
<212> TYPE: RNA
<213> ORGANISM: Artificial Sequence
<220> FEATURE:
<223> OTHER INFORMATION: GalAcs are conjugated at 3'-end of crRNA via an triazole nNt-Linker.

<400> SEQUENCE: 69
gcguggccug ggcgggacug guuuuaguac ucuguaauuu uagguaugag 50

<210> SEQ ID NO 70
<211> LENGTH: 31
<212> TYPE: RNA
<213> ORGANISM: Artificial Sequence
<220> FEATURE:
<223> OTHER INFORMATION: crRNA 3'-azide

<400> SEQUENCE: 70
cuauauggau gaugugguac guuuuagagc u 31

<210> SEQ ID NO 71
<211> LENGTH: 61
<212> TYPE: RNA
<213> ORGANISM: Artificial Sequence
<220> FEATURE:
<223> OTHER INFORMATION: 5'-alkynyl tracrRNA 3'-maleimide.

<400> SEQUENCE: 71
agcaaguuaa aauaaggcua guccguuauc aacuugaaaa aguggcaccg agucggugcu 60
u 61

<210> SEQ ID NO 72
<211> LENGTH: 92
<212> TYPE: RNA
<213> ORGANISM: Artificial Sequence
<220> FEATURE:
<223> OTHER INFORMATION: lgRNA 3'-maleimide. lgRNA contains a triazole
nNt-Linker between u31 and a32.

<400> SEQUENCE: 72
cuauauggau gaugugguac guuuuagagc uagcaaguua aaauaaggcu aguccguuau 60
caacuugaaa aaguggcacc gagucggugc uu 92

<210> SEQ ID NO 73
<211> LENGTH: 37
<212> TYPE: DNA
<213> ORGANISM: Artificial Sequence
<220> FEATURE:
<223> OTHER INFORMATION: ssDNA, 5'-thiol

<400> SEQUENCE: 73
ucagacttgg cccccatcaa tcaatcaatc catatag 37

<210> SEQ ID NO 74
<211> LENGTH: 129
<212> TYPE: DNA
<213> ORGANISM: Artificial Sequence
<220> FEATURE:
<223> OTHER INFORMATION: lgRNA-ssDNA conjugate with a thio-ether
nNt-Linker (u93 and u94).

<400> SEQUENCE: 74
cuauauggau gaugugguac guuuuagagc uagcaaguua aaauaaggcu aguccguuau 60
caacuugaaa aaguggcacc gagucggugc uuucagactt ggcccccatc aatcaatcaa 120
tccatatag 129

<210> SEQ ID NO 75
<211> LENGTH: 101
<212> TYPE: RNA
<213> ORGANISM: Artificial Sequence
<220> FEATURE:
<223> OTHER INFORMATION: sgRNA 3'-maleimide.

<400> SEQUENCE: 75
gcuauaugga ugaugguggua cguuuuagag cuagaaauag caaguuaaaa uaaggcuagu 60
ccguuaucaa cuugaaaaag uggcaccgag ucggugcuuu u 101

<210> SEQ ID NO 76
<211> LENGTH: 138
<212> TYPE: DNA
<213> ORGANISM: Artificial Sequence
<220> FEATURE:
<223> OTHER INFORMATION: lgRNA-ssDNA conjugate with a thio-ether
nNt-Linker (u101 and u102).

<400> SEQUENCE: 76
gcuauaugga ugauguggua cguuuuagag cuagaaauag caaguuaaaa uaaggcuagu 60
ccguuaucaa cuugaaaaag uggcaccgag ucggugcuuu uucagacttg gcccccatca 120
atcaatcaat ccatatag 138

<210> SEQ ID NO 77
<211> LENGTH: 129
<212> TYPE: DNA
<213> ORGANISM: Artificial Sequence
<220> FEATURE:
<223> OTHER INFORMATION: ssDNA-lgRNA conjugate with a thio-ether nNt-Linker (g36 and u37). A second nNt-Linker is between u68 and a69.

<400> SEQUENCE: 77
cagacttggc ccccatcaat caatcaatcc atatagucua uauggaugau gugguacguu 60
uuagagcuag caaguuaaaa uaaggcuagu ccguuaucaa cuugaaaaag uggcaccgag 120
ucggugcuu 129

<210> SEQ ID NO 78
<211> LENGTH: 128
<212> TYPE: DNA
<213> ORGANISM: Artificial Sequence
<220> FEATURE:
<223> OTHER INFORMATION: lgRNA-ssDNA conjugate with an nNt-Linker between u31 and a32, and a second nNt-Linker (thio-ether ) between g67 and u68. c93-g129 is a DNA oligonucleotide.

<400> SEQUENCE: 78
cuauauggau gaugugguac guuuuagagc uagcaaguua aaauaaggcu aguccguuau 60
caacuuguaa aguggcaccg agucggugcu uucagacttg gcccccatca atcaatcaat 120
ccatatag 128

<210> SEQ ID NO 79
<211> LENGTH: 84
<212> TYPE: DNA
<213> ORGANISM: Artificial Sequence
<220> FEATURE:
<223> OTHER INFORMATION: cDNA encoding SaCas9 tracrRNA.

<400> SEQUENCE: 79
caccacttat acctaaaatt acagaatcta ctaaaacaag gcaaaatgcc gtgtttatct 60
cgtcaacttg ttggcgagat tttt 84

<210> SEQ ID NO 80
<211> LENGTH: 84
<212> TYPE: DNA
<213> ORGANISM: Artificial Sequence
<220> FEATURE:
<223> OTHER INFORMATION: cDNA encoding SaCas9 tracrRNA.

<400> SEQUENCE: 80
ggccaaaaat ctcgccaaca agttgacgag ataaacacgg cattttgcct tgttttagta 60
gattctgtaa ttttaggtat aagt 84

<210> SEQ ID NO 81
<211> LENGTH: 4104
<212> TYPE: DNA
<213> ORGANISM: Artificial Sequence
<220> FEATURE:

<223> OTHER INFORMATION: DNA sequence of engineered SpCas9 protein by site-directed mutagenesis.

<400> SEQUENCE: 81

```
tgcgacaaga agtacagcat cggcctggac atcggcacca actctgtggg ctgggccgtg      60
atcaccgacg agtacaaggt gcccagcaag aaattcaagg tgctgggcaa caccgaccgg     120
cacagcatca agaagaacct gatcggagcc ctgctgttcg acagcggcga aacagccgag     180
gccacccggc tgaagagaac cgccagaaga agatacacca gacggaagaa ccggatcgcc     240
tatctgcaag agatcttcag caacgagatg gccaaggtgg acgacagctt cttccacaga     300
ctggaagagt ccttcctggt ggaagaggat aagaagcacg agcggcaccc catcttcggc     360
aacatcgtgg acgaggtggc ctaccacgag aagtacccca ccatctacca cctgagaaag     420
aaactggtgg actgcaccga caaggccgac ctgcggctga tctatctggc cctggcccac     480
atgatcaagt tccggggcca cttcctgatc gagggcgacc tgaaccccga caacagcgac     540
gtggacaagc tgttcatcca gctggtgcag acctacaacc agctgttcga ggaaaacccc     600
atcaacgcct gcggcgtgga cgccaaggcc atcctgtctg ccagactgag caagagcaga     660
cggctggaaa atctgatcgc ccagctgccc ggcgagaaga agaatggcct gttcggaaac     720
ctgattgccc tgagcctggg cctgaccccc aacttcaaga gcaacttcga cctggccgag     780
gatgccaaac tgcagctgag caaggacacc tacgacgacg acctggacaa cctgctggcc     840
cagatcggcg accagtacgc cgacctgttt ctggccgcca agaacctgtc cgacgccatc     900
ctgctgagcg acatcctgag agtgaacacc gagatcacca aggcccccct gagcgcctct     960
atgatcaaga gatacgacga gcaccaccag gacctgaccc tgctgaaagc tctcgtgcgg    1020
cagcagctgc ctgagaagta caaagagatt ttcttcgacc agagcaagaa cggctacgcc    1080
ggctacattg acggcggagc cagccaggaa gagttctaca agttcatcaa gcccatcctg    1140
gaaaagatgg acggcaccga ggaactgctc gtgaagctga acagagagga cctgctgcgg    1200
aagcagcgga ccttcgacaa cggcagcatc ccccaccaga tccacctggg agagctgcac    1260
gccattctgc ggcggcagga agatttttac ccattcctga aggacaaccg ggaaaagatc    1320
gagaagatcc tgaccttccg catcccctac tacgtgggcc ctctggccag gggaaacagc    1380
agattcgcct ggatgaccag aaagtgcgag gaaaccatca ccccctggaa cttcgaggaa    1440
gtggtggaca agggcgcttc cgcccagagc ttcatcgagc ggatgaccaa cttcgataag    1500
aacctgccca acgagaaggt gctgcccaag cacagcctgc tgtacgagta cttcaccgtg    1560
tataacgagc tgaccaaagt gaaatacgtg accgagggaa tgagaaagcc cgccttcctg    1620
agcggcgagc agaaaaaggc catcgtggac ctgctgttca agaccaaccg gaaagtgacc    1680
gtgaagcagc tgaaagagga ctacttcaag aaaatcgagt gcttcgactc cgtggaaatc    1740
tccggcgtgg aagatcggtt caacgcctcc ctgggcacat accacgatct gctgaaaatt    1800
atcaaggaca aggacttcct ggacaatgag gaaaacgagg acattctgga agatatcgtg    1860
ctgaccctga cactgtttga ggacagagag atgatcgagg aacggctgaa aacctatgcc    1920
cacctgttcg acgacaaagt gatgaagcag ctgaagcggc ggagatacac cggctggggc    1980
aggctgagcc ggaagctgat caacggcatc cgggacaagc agtccggcaa gacaatcctg    2040
gatttcctga agtccgacgg cttcgccaac agaaacttca tgcagctgat ccacgacgac    2100
agcctgacct ttaaagagga catccagaaa gcccaggtgt ccggccaggg cgatagcctg    2160
cacgagcaca ttgccaatct ggccggcagc cccgccatta agaagggcat cctgcagaca    2220
```

-continued gtgaaggtgg tggacgagct cgtgaaagtg atgggccggc acaagcccga gaacatcgtg 2280
atcgaaatgg ccagagagaa ccagaccacc cagaagggac agaagaacag ccgcgagaga 2340
atgaagcgga tcgaagaggg catcaaagag ctgggcagcc agatcctgaa agaacacccc 2400
gtggaaaaca cccagctgca gaacgagaag ctgtacctgt actacctgca gaatgggcgg 2460
gatatgtacg tggaccagga actggacatc aaccggctgt ccgactacga tgtggaccat 2520
atcgtgcctc agagctttct gaaggacgac tccatcgaca acaaggtgct gaccagaagc 2580
gacaagaacc ggggcaagag cgacaacgtg ccctccgaag aggtcgtgaa gaagatgaag 2640
aactactggc ggcagctgct gaacgccaag ctgattaccc agagaaagtt cgacaatctg 2700
accaaggccg agagaggcgg cctgagcgaa ctggataagg ccggcttcat caagagacag 2760
ctggtggaaa cccggcagat cacaaagcac gtggcacaga tcctggactc ccggatgaac 2820
actaagtacg acgagaatga caagctgatc cgggaagtga aagtgatcac cctgaagtcc 2880
aagctggtgt ccgatttccg gaaggatttc cagttttaca aagtgcgcga gatcaacaac 2940
taccaccacg cccacgacgc ctacctgaac gccgtcgtgg gaaccgccct gatcaaaaag 3000
taccctaagc tggaaagcga gttcgtgtac ggcgactaca aggtgtacga cgtgcggaag 3060
atgatcgcca agagcgagca ggaaatcggc aaggctaccg ccaagtactt cttctacagc 3120
aacatcatga actttttcaa gaccgagatt accctggcca acggcgagat ccggaagcgg 3180
cctctgatcg agacaaacgg cgaaaccggg gagatcgtgt gggataaggg ccgggatttt 3240
gccaccgtgc ggaaagtgct gagcatgccc caagtgaata tcgtgaaaaa gaccgaggtg 3300
cagacaggcg gcttcagcaa agagtctatc ctgcccaaga ggaacagcga taagctgatc 3360
gccagaaaga aggactggga ccctaagaag tacggcggct tcgacagccc caccgtggcc 3420
tattctgtgc tggtggtggc caaagtggaa aagggcaagt ccaagaaact gaagtgcgtg 3480
aaagagctgc tggggatcac catcatggaa agaagcagct tcgagaagaa tcccatcgac 3540
tttctggaag ccaagggcta caaagaagtg aaaaaggacc tgatcatcaa gctgcctaag 3600
tactccctgt tcgagctgga aaacggccgg aagagaatgc tggcctctgc cggcgaactg 3660
cagaagggaa acgaactggc cctgccctcc aaatatgtga acttcctgta cctggccagc 3720
cactatgaga agctgaaggg ctcccccgag gataatgagc agaaacagct gtttgtggaa 3780
cagcacaagc actacctgga cgagatcatc gagcagatca gcgagttctc caagagagtg 3840
atcctggccg acgctaatct ggacaaagtg ctgtccgcct acaacaagca ccgggataag 3900
cccatcagag agcaggccga gaatatcatc cacctgttta ccctgaccaa tctgggagcc 3960
cctgccgcct tcaagtactt tgacaccacc atcgaccgga agaggtacac cagcaccaaa 4020
gaggtgctgg acgccaccct gatccaccag agcatcaccg gcctgtacga gacacggatc 4080
gacctgtctc agctgggagg cgac 4104

<210> SEQ ID NO 82
<211> LENGTH: 1392
<212> TYPE: PRT
<213> ORGANISM: Artificial Sequence
<220> FEATURE:
<223> OTHER INFORMATION: Sequence of an engineered SpCas9-NLS protein.

<400> SEQUENCE: 82

Cys Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

-continued

```
Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Ala
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Cys
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Cys Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445
```

-continued

```
Pro Tyr Tyr Val Gly Pro Leu Ala Arg Gly Asn Ser Arg Phe Ala Trp
    450                 455                 460

Met Thr Arg Lys Cys Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860
```

-continued

Gly Lys Ser Asp Asn Val Pro Ser Glu Glu Val Val Lys Lys Met Lys
865 870 875 880

Asn Tyr Trp Arg Gln Leu Leu Asn Ala Lys Leu Ile Thr Gln Arg Lys
885 890 895

Phe Asp Asn Leu Thr Lys Ala Glu Arg Gly Gly Leu Ser Glu Leu Asp
900 905 910

Lys Ala Gly Phe Ile Lys Arg Gln Leu Val Glu Thr Arg Gln Ile Thr
915 920 925

Lys His Val Ala Gln Ile Leu Asp Ser Arg Met Asn Thr Lys Tyr Asp
930 935 940

Glu Asn Asp Lys Leu Ile Arg Glu Val Lys Val Ile Thr Leu Lys Ser
945 950 955 960

Lys Leu Val Ser Asp Phe Arg Lys Asp Phe Gln Phe Tyr Lys Val Arg
965 970 975

Glu Ile Asn Asn Tyr His His Ala His Asp Ala Tyr Leu Asn Ala Val
980 985 990

Val Gly Thr Ala Leu Ile Lys Lys Tyr Pro Lys Leu Glu Ser Glu Phe
995 1000 1005

Val Tyr Gly Asp Tyr Lys Val Tyr Asp Val Arg Lys Met Ile Ala
1010 1015 1020

Lys Ser Glu Gln Glu Ile Gly Lys Ala Thr Ala Lys Tyr Phe Phe
1025 1030 1035

Tyr Ser Asn Ile Met Asn Phe Phe Lys Thr Glu Ile Thr Leu Ala
1040 1045 1050

Asn Gly Glu Ile Arg Lys Arg Pro Leu Ile Glu Thr Asn Gly Glu
1055 1060 1065

Thr Gly Glu Ile Val Trp Asp Lys Gly Arg Asp Phe Ala Thr Val
1070 1075 1080

Arg Lys Val Leu Ser Met Pro Gln Val Asn Ile Val Lys Lys Thr
1085 1090 1095

Glu Val Gln Thr Gly Gly Phe Ser Lys Glu Ser Ile Leu Pro Lys
1100 1105 1110

Arg Asn Ser Asp Lys Leu Ile Ala Arg Lys Lys Asp Trp Asp Pro
1115 1120 1125

Lys Lys Tyr Gly Gly Phe Asp Ser Pro Thr Val Ala Tyr Ser Val
1130 1135 1140

Leu Val Val Ala Lys Val Glu Lys Gly Lys Ser Lys Lys Leu Lys
1145 1150 1155

Cys Val Lys Glu Leu Leu Gly Ile Thr Ile Met Glu Arg Ser Ser
1160 1165 1170

Phe Glu Lys Asn Pro Ile Asp Phe Leu Glu Ala Lys Gly Tyr Lys
1175 1180 1185

Glu Val Lys Lys Asp Leu Ile Ile Lys Leu Pro Lys Tyr Ser Leu
1190 1195 1200

Phe Glu Leu Glu Asn Gly Arg Lys Arg Met Leu Ala Ser Ala Gly
1205 1210 1215

Glu Leu Gln Lys Gly Asn Glu Leu Ala Leu Pro Ser Lys Tyr Val
1220 1225 1230

Asn Phe Leu Tyr Leu Ala Ser His Tyr Glu Lys Leu Lys Gly Ser
1235 1240 1245

Pro Glu Asp Asn Glu Gln Lys Gln Leu Phe Val Glu Gln His Lys
1250 1255 1260

```
His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365

Ala Tyr  Pro Tyr Asp Val Pro  Asp Tyr Ala Ser Leu  Gly Ser Gly
    1370                 1375                 1380

Ser Pro  Lys Lys Lys Arg Lys  Val Asp
    1385                 1390


<210> SEQ ID NO 83
<211> LENGTH: 16
<212> TYPE: PRT
<213> ORGANISM: Artificial Sequence
<220> FEATURE:
<223> OTHER INFORMATION: Synthetic

<400> SEQUENCE: 83

Gly Gly Gly Arg Arg Arg Arg Arg Arg Arg Arg Arg Leu Leu Leu Leu
1               5                   10                  15


<210> SEQ ID NO 84
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 84

tgantgantg a                                                          11


<210> SEQ ID NO 85
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 85

tgantganta a                                                          11
```

<210> SEQ ID NO 86
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 86
tgantganta g 11

<210> SEQ ID NO 87
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 87
tgantaantg a 11

<210> SEQ ID NO 88
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 88
tgantaanta a 11

<210> SEQ ID NO 89
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 89
tgantaanta g 11

<210> SEQ ID NO 90
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 90
tgantgantg a 11

<210> SEQ ID NO 91
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 91
tgantganta a 11

<210> SEQ ID NO 92
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 92
tgantganta g 11

<210> SEQ ID NO 93
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)

<223> OTHER INFORMATION: n is a, c, g, or t

<400> SEQUENCE: 93
taantgantg a 11

<210> SEQ ID NO 94
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 94
taantganta a 11

<210> SEQ ID NO 95
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 95
taantganta g 11

<210> SEQ ID NO 96
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 96
taantaantg a 11

<210> SEQ ID NO 97
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 97
taantaanta a 11

<210> SEQ ID NO 98
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 98
taantaanta g 11

<210> SEQ ID NO 99
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 99
taantgantg a 11

<210> SEQ ID NO 100
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 100
taantganta a 11

<210> SEQ ID NO 101
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:

-continued

<221> NAME/KEY: misc_feature
<222> LOCATION: (8)..(8)
<223> OTHER INFORMATION: n is a, c, g, or t

<400> SEQUENCE: 101
taantganta g 11

<210> SEQ ID NO 102
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 102
tagntgantg a 11

<210> SEQ ID NO 103
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 103
tagntganta a 11

<210> SEQ ID NO 104
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 104
tagntganta g 11

<210> SEQ ID NO 105
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 105
tagntaantg a 11

<210> SEQ ID NO 106
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 106
tagntaanta a 11

<210> SEQ ID NO 107
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 107
tagntaanta g 11

<210> SEQ ID NO 108
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 108
tagntgantg a 11

<210> SEQ ID NO 109
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)

-continued

```
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 109

tagntganta a                                                      11


<210> SEQ ID NO 110
<211> LENGTH: 11
<212> TYPE: DNA
<213> ORGANISM: Artificial Sequence
<220> FEATURE:
<223> OTHER INFORMATION: Stop codons.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 110

tagntganta g                                                      11
```

What is claimed is:

1. A conjugate comprising:

i. a clustered regularly interspaced short palindromic repeats (CRISPR)-Cas protein-chemically ligated guide RNA (lgRNA) complex (RNP); and ii. one or more molecules selected from the group consisting of antibodies, aptamers, and a single strand nucleic acid template, wherein said lgRNA comprises:

(i) a spacer of an oligonucleotide that targets a DNA sequence, and (ii) at least one non-nucleotide linker located after its first nucleotide and before its last nucleotide, and wherein said one or more molecules are covalently linked to said lgRNA by one or more non-nucleotide linkers at one or more positions other than the 5'-end of said lgRNA.

2. Said conjugate of claim 1, wherein each of said non-nucleotide linkers is independently selected from a group consisting of chemical structures comprising:

i. an optionally substituted M core structure of Formula M-1 to M-18:

M-1

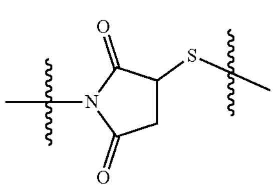

M-2

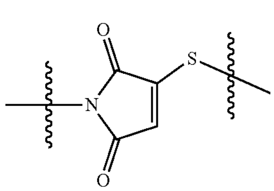

-continued

M-3

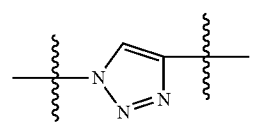

M-4

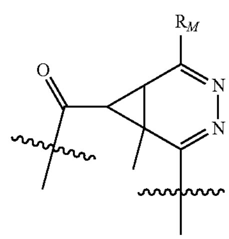

M-5

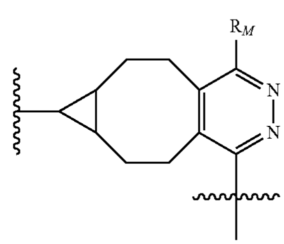

M-6

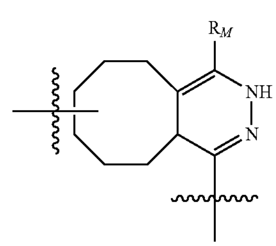

-continued
M-7
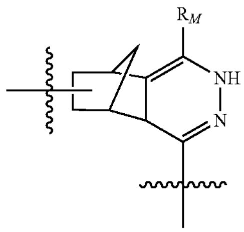
M-8
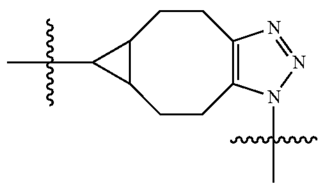
M-9
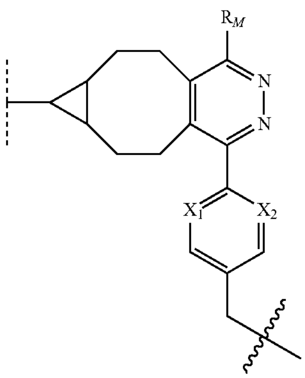
M-10
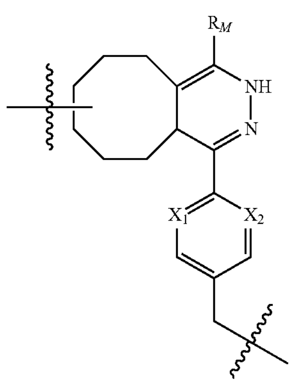
M-11
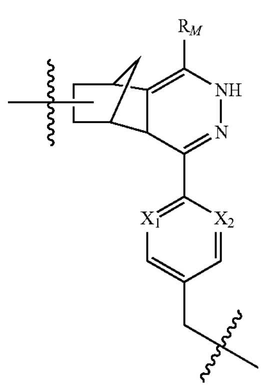
-continued
M-12
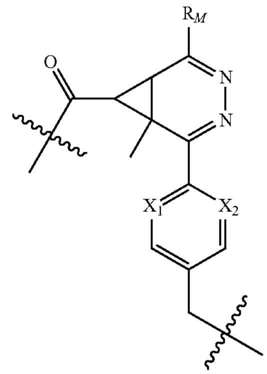
M-13
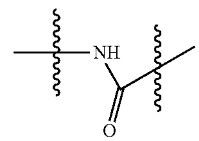
M-14
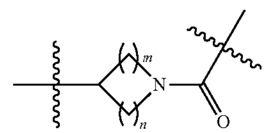
M-15
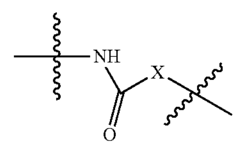
M-16
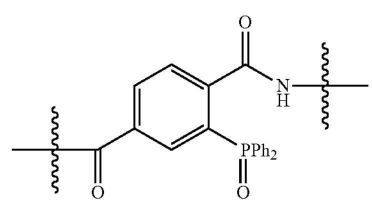
M-17
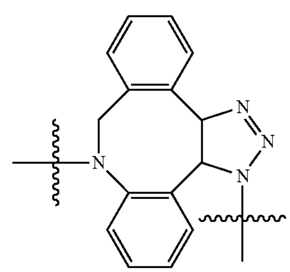
M-18
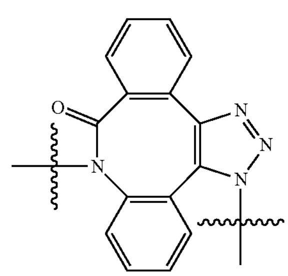,
wherein X=O, S, NH, or $CH_2$; $X_1$=N or CH; $X_2$=N or CH; $R_M$=H, $CH_3$, alkyl, aryl, or heteroaryl, m=0 to 3 and n=0 to 3, and ii. two L linkers, and each said L linker comprises one or more structures selected from the group consisting of L-1 to L-24:
L-1
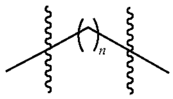
L-2
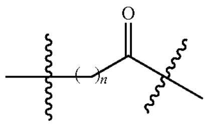
L-3
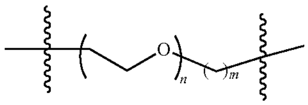
L-4
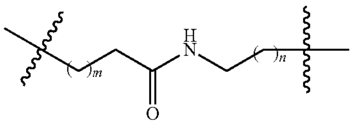
L-5
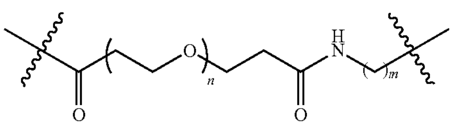
L-6
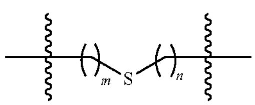
L-7
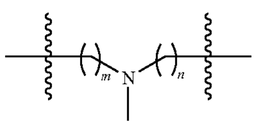
L-8
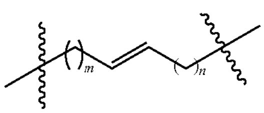
L-9
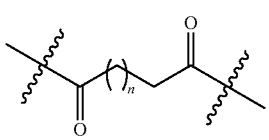
L-10
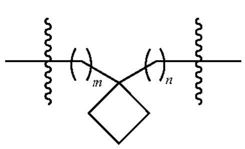
L-11
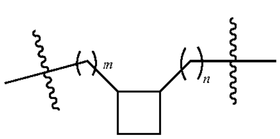
-continued
L-12
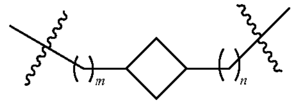
L-13
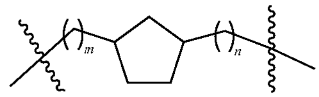
L-14
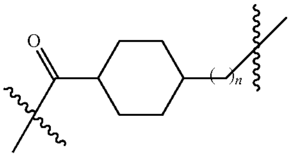
L-15
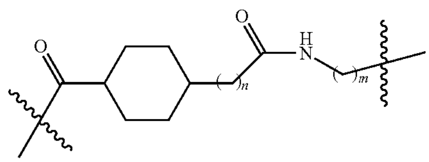
L-16
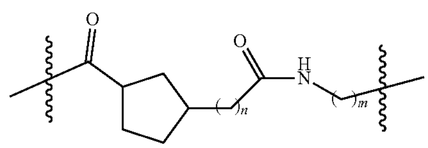
L-17
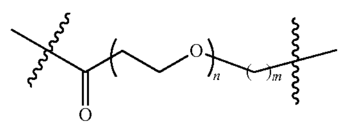
L-18
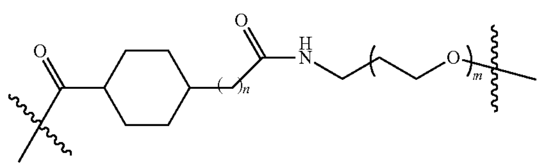
L-19
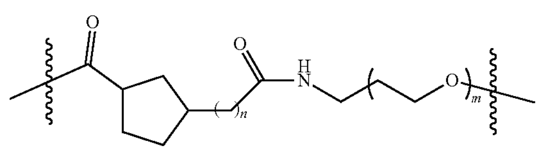
L-20
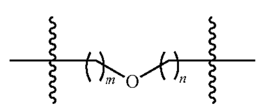
L-21
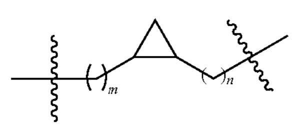
L-22
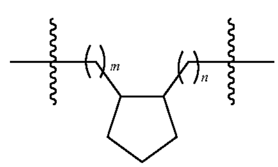

-continued
L-23
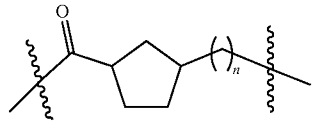
L-24
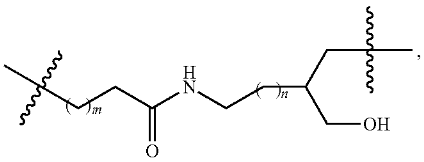
wherein m=0 to 16 and n=0 to 16,
and wherein
said L linkers and said M core structure are joined as L-M-L, wherein the two L linkers are the same or different, and attached to two terminal nucleotides of Formula Nuc-1 to Nuc-19:
Nuc-1
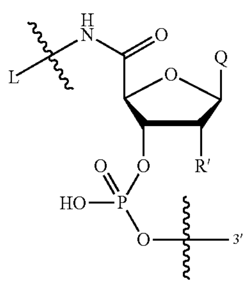
Nuc-2
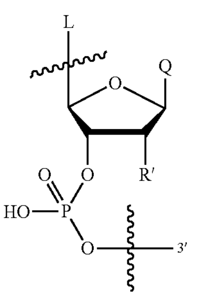
Nuc-3
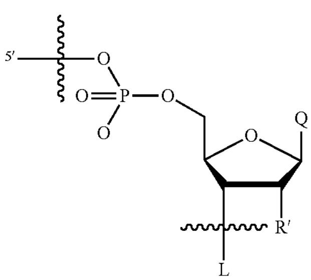
Nuc-4
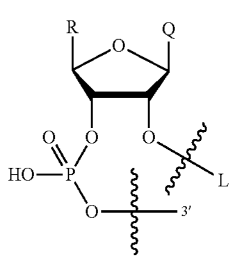
-continued
Nuc-5
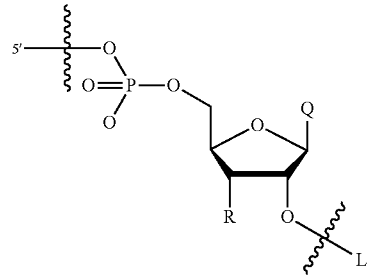
Nuc-6
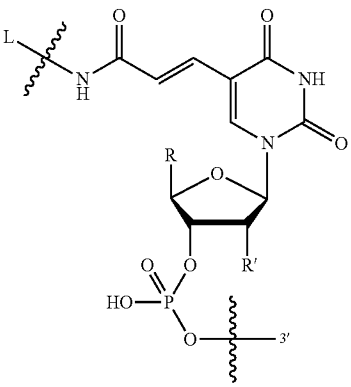
Nuc-7
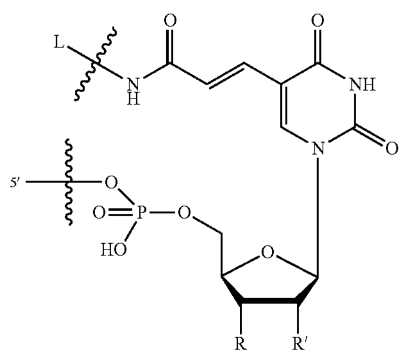
Nuc-8
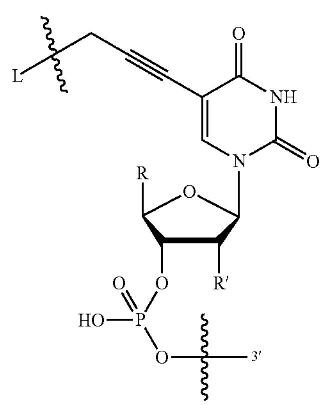

-continued
Nuc-9
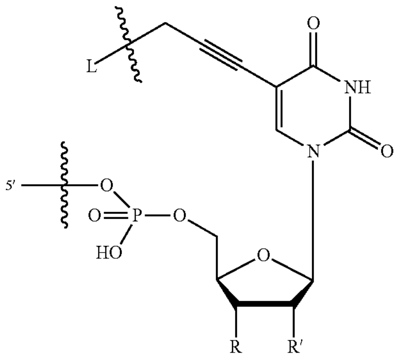
Nuc-10
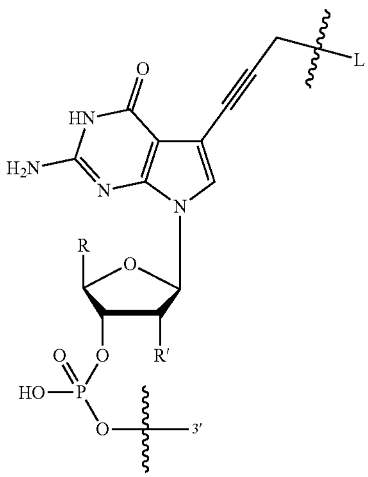
Nuc-11
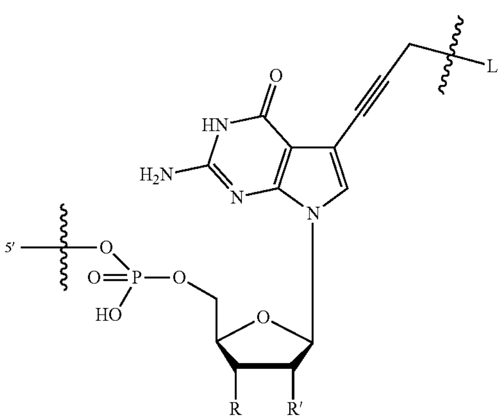
Nuc-12
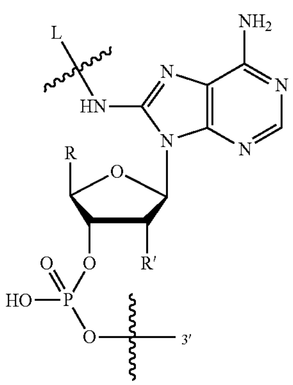
-continued
Nuc-13
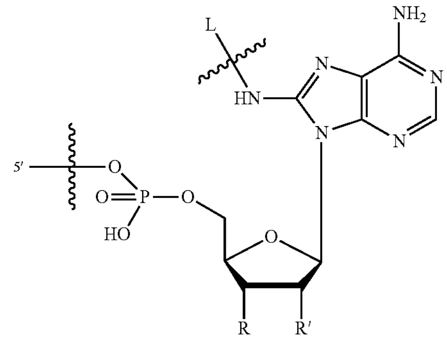
Nuc-14
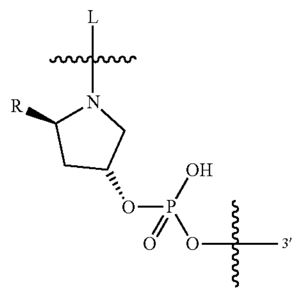
Nuc-15
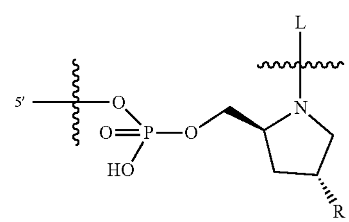
Nuc-16
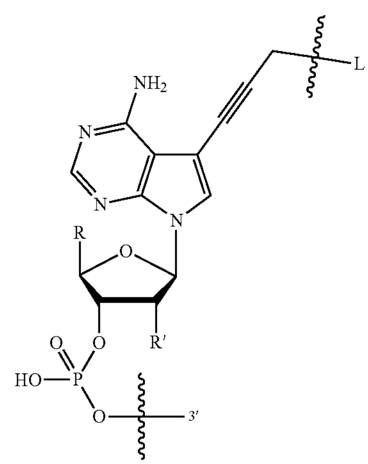

-continued

Nuc-17

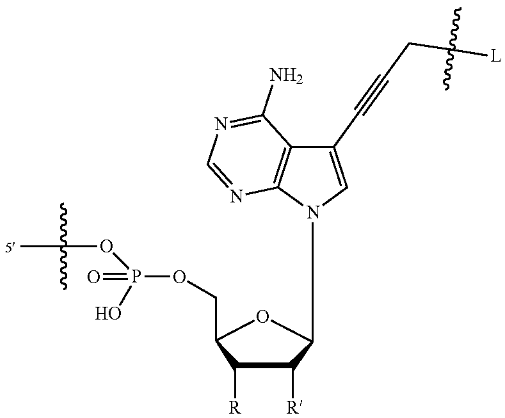

Nuc-18

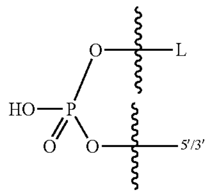

Nuc-19

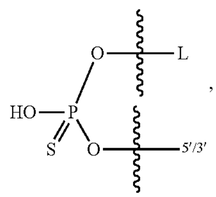

, wherein the attached positions are

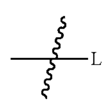

to L-M-L and

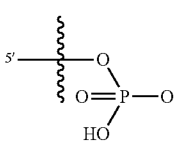

or

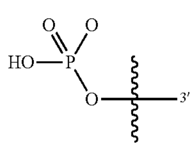 [SMILES: *OP(=O)(O)O]

to upstream and downstream oligonucleotides, respectively, and wherein R is H, OH,

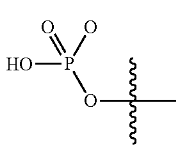

, $CH_2OH$,

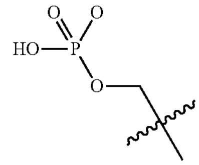

,

F, $NH_2$, OMe, $CH_2OMe$, $OCH_2CH_2OMe$, an alkyl, a cycloalkyl, an aryl, or a heteroaryl; R' is H, OH,

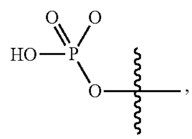 [SMILES: *OP(=O)(O)O]

, $CH_2OH$

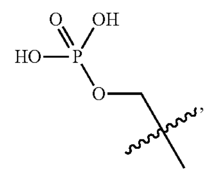 [SMILES: *COP(=O)(O)O]

,

F, $NH_2$, OMe, $CH_2OMe$, $OCH_2CH_2OMe$, an alkyl, a cycloalkyl, an aryl, or a heteroaryl, and Q is a natural or a non-natural nucleic acid base.

3. Said conjugate of claim 1, wherein said Cas protein is covalently linked with one or more molecules selected from the group consisting of polyethylene glycol (PEG), non-PEG polymers, ligands of cellular receptors, lipids, oligonucleotides, antibodies, polysaccharides, aptamers, glycans and peptides to form a Cas protein conjugate, and the said more molecules can be the same or different.

4. Said conjugate of claim 3, wherein said one or more molecules covalently linked to said Cas protein comprise molecules for targeted cellular delivery.

5. Said conjugate of claim 1, comprising one or more nucleotides selected from the group consisting of:

II-1

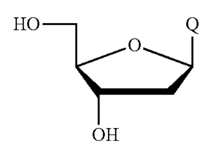

II-2

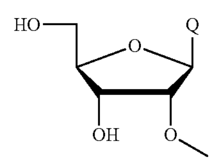

II-3

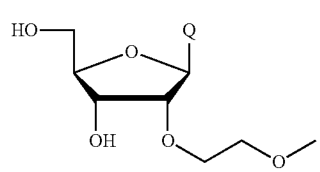

-continued
II-4
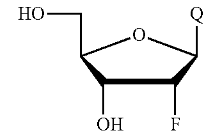
II-5
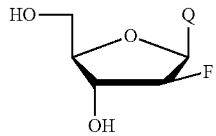
II-6
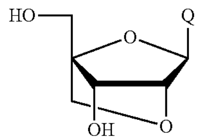
II-7
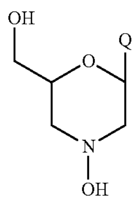
II-8
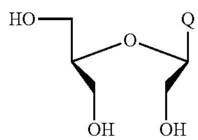
II-9
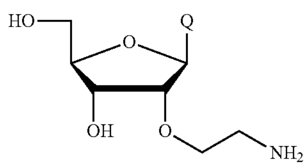
II-10
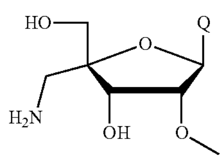
II-11
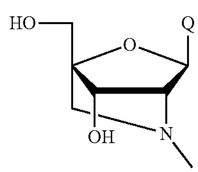
II-12
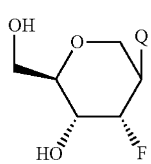
II-13
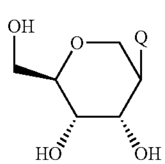
-continued
II-14
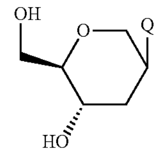
II-15
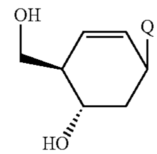
II-16
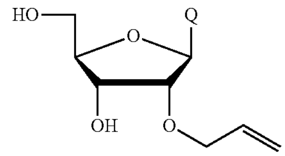
II-17
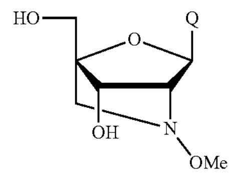
II-18
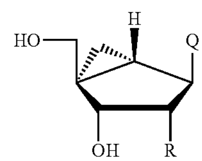
II-19
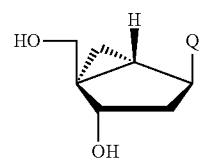
II-20
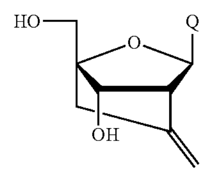
II-21
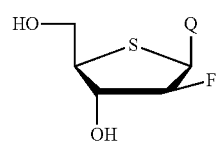
II-22
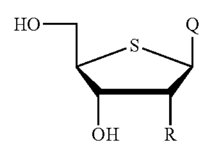
II-23
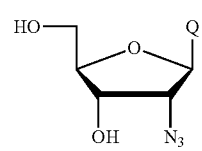

-continued
II-24
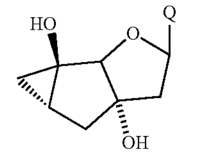
II-25
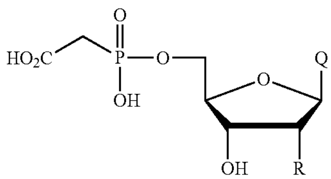
II-26
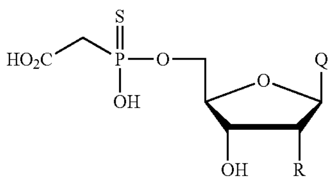
II-27
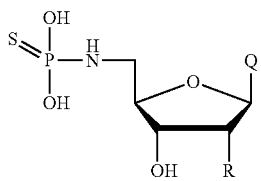
II-28
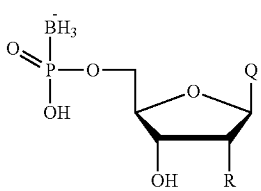
II-29
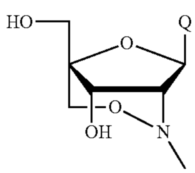
II-30
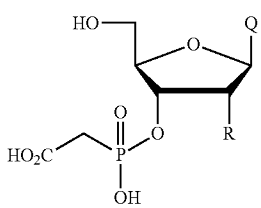
II-31
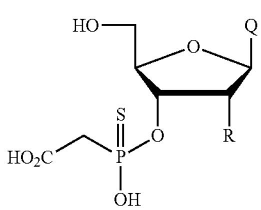
-continued
II-32
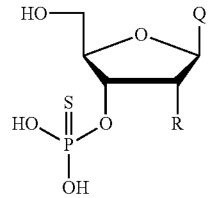
II-33
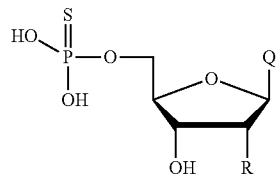
II-34
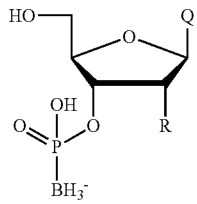
II-35
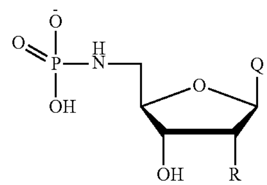
II-36
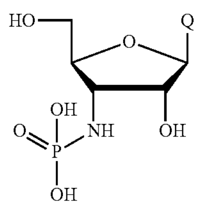
II-37
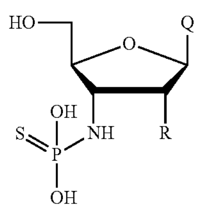
II-39
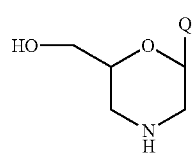
II-41
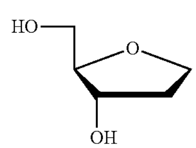

-continued
II-42
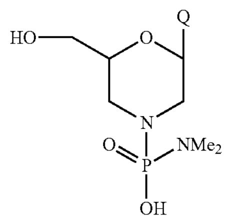
II-43
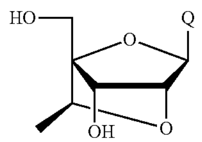
wherein R is H, OH, F, OMe, or $OCH_2CH_2OCH_3$ and Q is a nucleobase or modified nucleobase selected from the group consisting of B-1 through 38 and B-40 through 45:
B-1
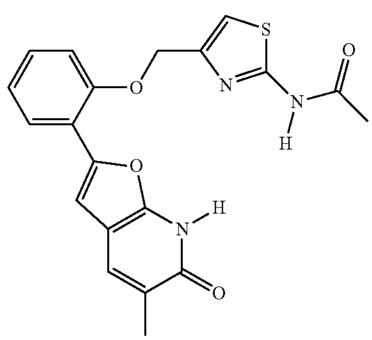
B-2
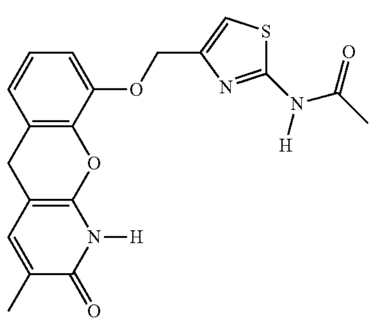
B-3
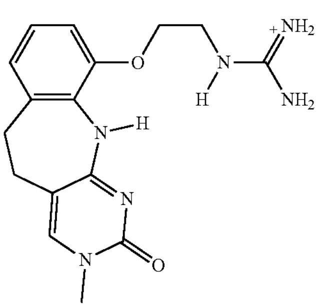
-continued
B-4
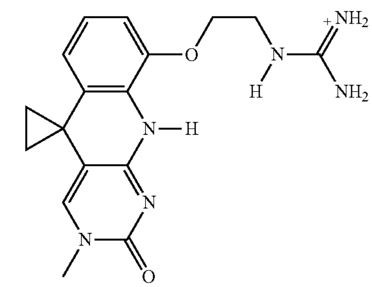
B-5
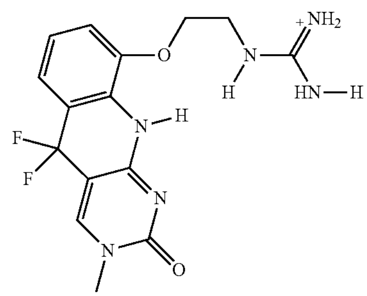
B-6
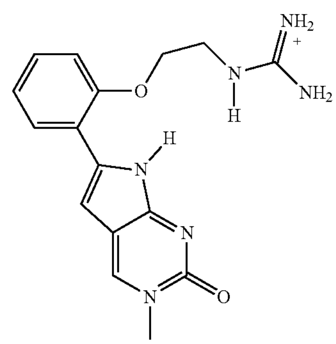
B-7
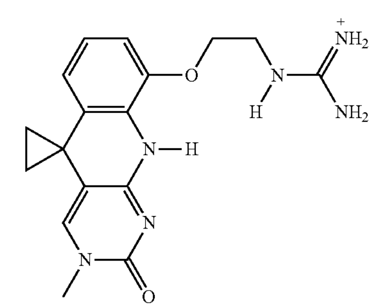
B-8
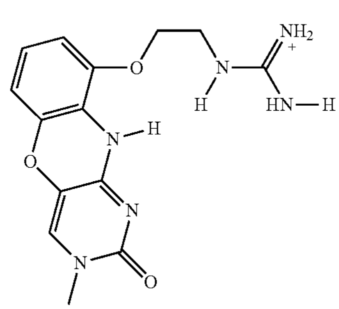

-continued
B-8-1
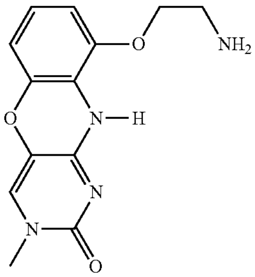
B-9
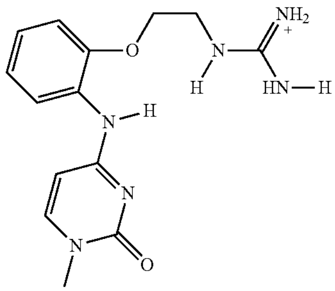
B-10
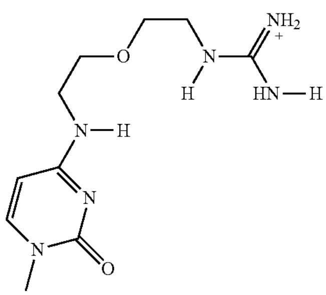
B-11
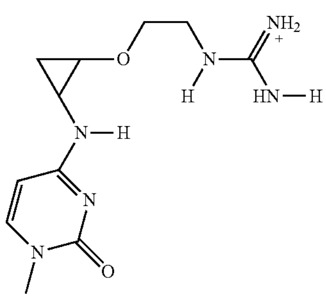
B-12
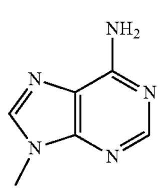
B-13
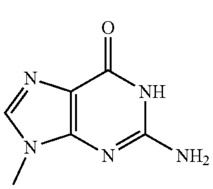
-continued
B-14
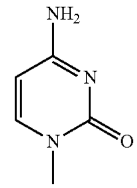
B-15
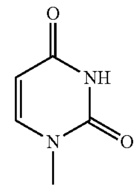
B-16
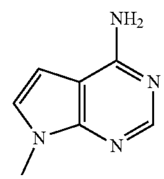
B-17
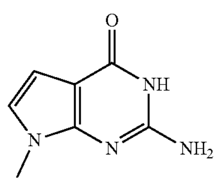
B-18
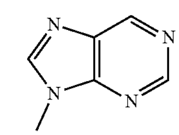
B-19
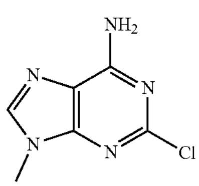
B-20
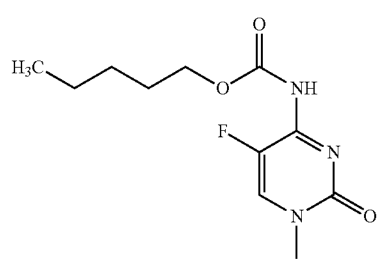
B-21
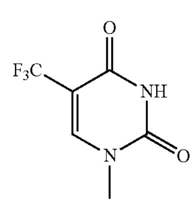

-continued
B-22
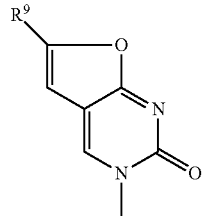
B-23
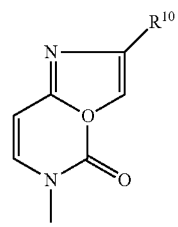
B-24
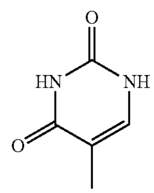
B-25
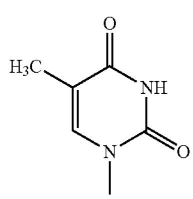
B-26
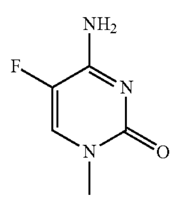
B-27
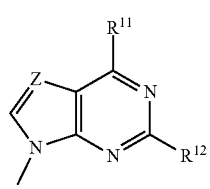
B-28
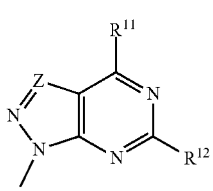
-continued
B-29
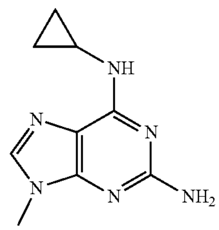
B-30
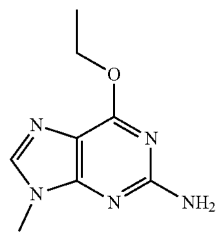
B-31
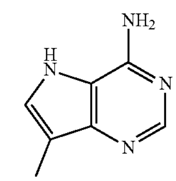
B-32
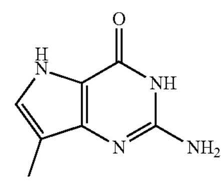
B-33
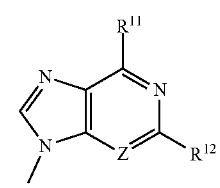
B-34
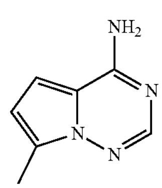
B-35
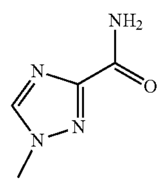
B-36
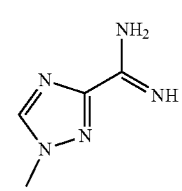

-continued

B-37

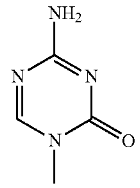

B-38

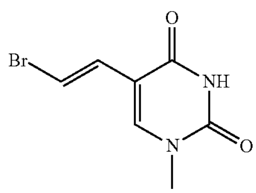

B-40

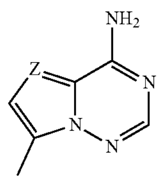

B-41

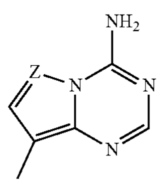

B-42

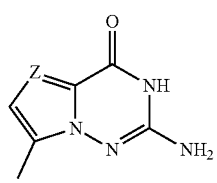

B-43

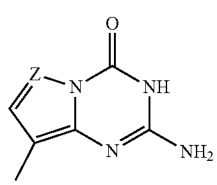

B-44

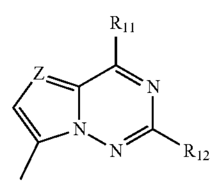

B-45

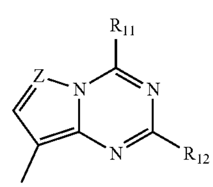

wherein (i) Z is N or $CR^{10}$; and (ii) $R^9$, $R^{10}$, $R^{11}$ and $R^{12}$ are independently H, F, Cl, Br, I, OH, OR', SH, SR', SeH, SeR', $NH_2$, NHR', NHOH, NHOR', NR'OR', $NR'_2$, $NHNH_2$, $NR'NH_2$, NR'NHR', $NHNR'_2$, $NR'NR'_2$, alkyl of $C_1$-$C_6$, halogenated alkyl of $C_1$-$C_6$, alkenyl of $C_2$-$C_6$, halogenated alkenyl of $C_2$-$C_6$, CN, alkynyl of $C_2$-$C_6$, halogenated alkynyl of $C_2$-$C_6$, alkoxy of $C_1$-$C_6$, halogenated alkoxy of $C_1$-$C_6$, CN, $CO_2H$, $CO_2R'$, $CONH_2$, CONHR', $CONR'_2$, $CH{=}CHCO_2H$, or $CH{=}CHCO_2R'$, wherein R' is H, an optionally substituted alkyl, an optionally substituted cycloalkyl, an optionally substituted alkynyl of $C_2$-$C_6$, an optionally substituted alkenyl of $C_2$-$C_6$, an optionally substituted aryl, or an optionally substituted heteroaryl, or when R' is part of $NR'_2$ and $NR'_2$ is a heterocyclic group linked at its N.

6. Said conjugate of claim 1, wherein said spacer is selected from sequences of 12-20 nt in human immunodeficiency virus (HIV) genomes, of which each thymine is replaced with uracil.

7. Said conjugate of claim 1, wherein said spacer is selected from sequences of 12-20 nt in hepatitis B virus (HBV) genomes, of which each thymine is replaced with uracil.

8. Said conjugate of claim 1, wherein said spacer is selected from sequences of 12-20 nt in herpes simplex virus (HSV) genomes, of which each thymine is replaced with uracil.

9. Said conjugate of claim 1, wherein said spacer is selected from sequences of 12-20 nt in Epstein-Barr virus (EBV) genomes, of which each thymine is replaced with uracil.

10. Said conjugate of claim 1, wherein said spacer is selected from sequences of 12-20 nt of a host genome to be edited, of which each thymine is replaced with uracil.

11. Said conjugate of claim 1, wherein said nucleic acid template comprises a gene editing sequence flanked with two homology arms, said homology arms each overlapping with the target strand or the non-target strand of a target DNA duplex to be edited, and wherein said homology arms are optionally modified.

12. Said conjugate of claim 11, wherein said gene editing sequence comprises an oligonucleotide sequence to introduce one or more stop codons selected from the group consisting of 5'-(tga)-3', 5'-(taa)-3', 5'-(tag)-3', 5'-(tga-ntga-ntga)-3' (Sequence No. 84), 5'-(tga-ntga-ntaa)-3' (Sequence No. 85), 5'-(tga-ntga-ntag)-3' (Sequence No. 86), 5'-(tga-ntaa-ntga)-3' (Sequence No. 87), 5'(tga-ntaa-ntaa)-3' (Sequence No. 88), 5'-(tga-ntaa-ntag)-3' (Sequence No. 89), 5'-(tga-ntga-ntga)-3' (Sequence No. 90), 5'-(tga-ntga-ntaa)-3' (Sequence No. 91), 5'-(tga-ntga-ntag)-3' (Sequence No. 92), 5'-(taa-ntga-ntga)-3' (Sequence No. 93), 5'-(taa-ntga-ntaa)-3' (Sequence No. 94), 5'-(taa-ntga-ntag)-3' (Sequence No. 95), 5'-(taa-ntaa-ntga)-3' (Sequence No. 96), 5'-(taa-ntaa-ntaa)-3' (Sequence No. 97), 5'-(taa-ntaa-ntag)-3' (Sequence No. 98), 5'-(taa-ntga-ntga)-3' (Sequence 99), 5'-(taa-ntga-ntaa)-3' (Sequence 100), 5'-(taa-ntga-ntag)-3' (Sequence No. 101), 5'-(tag-ntga-ntga)-3' (Sequence No. 102), 5'-(tag-ntga-ntaa)-3' (Sequence No. 103), 5'-(tag-ntga-ntag)-3' (Sequence No. 104), 5'-(tag-ntaa-ntga)-3' (Sequence No. 105), 5'-(tag-ntaa-ntaa)-3' (Sequence No. 106), 5'-(tag-ntaa-ntag)-3' (Sequence No. 107), 5'-(tag-ntga-ntga)-3' (Sequence 108), 5'-(tag-ntga-ntaa)-3' (Sequence No. 109) and 5'-(tag-ntga-ntag)-3' (Sequence No. 110), wherein n is any nucleotide.

13. Said conjugate of claim 11, wherein said gene editing sequence comprises an oligonucleotide sequence to introduce one or more transcription cis-regulatory elements.

14. Said conjugate of claim 1 comprising a mixture of lgRNA conjugates of various spacers targeting at different loci of target genomes, and/or sequences of variants or viral quasispecies of a single locus of target genomes.

15. Said conjugate of claim 1, wherein said Cas protein is a recombinant engineered class 2 endonuclease, catalytically inactive class 2 Cas endonuclease, nickase, or Cas-effector fusion protein.

16. Said conjugate of claim 15, wherein said Cas protein is a recombinant engineered endonuclease comprising at least two cysteines, and at least one of said cysteines are introduced by site directed mutations of internal amino acids, and said cysteines are conjugated with molecules for epitope masking and/or targeted delivery, and wherein the wild type cysteines are optionally mutated to avoid deactivation of said Cas protein due to covalent conjugations.

17. Said conjugate of claim 15, wherein said Cas-effector fusion protein is a Cas protein fused with a DNA polymerase, said nucleic acid template is a DNA, and said DNA polymerase uses said DNA template for gene editing.

18. Said conjugate of claim 1, wherein said complex is PEGylated.

19. A method of editing a target gene using the conjugate of claim 1, comprising the following steps:

i. cleaving a target gene DNA to be edited by said Cas protein of said conjugate, thereby generating a double-strand break or a nick; and ii. hybridizing a resulting single-stranded DNA of the cleavage product with a 3'-homology arm of said covalently linked nucleic acid template of said conjugate and extending the 3'-end of said single DNA strand using said template as a template, thereby editing the target gene.

20. Said conjugate of claim 1, wherein said conjugate is self-assembled in a cell from (i) a Cas protein expressed from a viral plasmid or from mRNA encoding said Cas protein, and (ii) the lgRNA to which said one or more molecules are covalently linked.

21. Said conjugate of claim 1, wherein said CRISPR-Cas protein is a fusion protein of nickase or catalytically inactive Cas further comprising one or more functional protein domains selected from the group consisting of FokI, DNA polymerase, reverse transcriptase, DNA methyltransferase, nucleic acid deaminases, transcription activator(s), transcription repressor(s), and histone acetyltransferase and deacetylase.

22. Said conjugate of claim 1, wherein said covalently-linked nucleic acid template is used by a host protein for gene editing.

23. Said conjugate of claim 22, wherein said host protein is endogenous.

24. Said conjugate of claim 22, wherein both said host protein and said Cas protein are parts of a fusion protein.

25. Said conjugate of claim 1, wherein said covalently-linked nucleic acid template is an ssDNA.

26. Pharmaceutical agents comprising:

i. an lgRNA; and ii. one or more molecules selected from the group consisting of antibodies, aptamers, and a single strand nucleic acid template, wherein said lgRNA is a guide RNA comprising:

(i) a spacer of an oligonucleotide that targets a DNA sequence; and (ii) at least one non-nucleotide linker located after its first nucleotide and before its last nucleotide, wherein said one or more molecules are covalently linked to said lgRNA by one or more non-nucleotide linkers at one or more positions other than the 5'-end of said LgRNA.

27. Pharmaceutical agents of claim 26, further comprising:

i. a Cas protein or a conjugate thereof;

ii. an mRNA encoding a Cas protein;

iii. a plasmid encoding a Cas protein; or iv. a viral vector encoding a Cas protein.

28. Pharmaceutical agents of claim 26 further comprising:

i. a fusion protein of nickase or catalytically inactive Cas and one or more functional protein domains selected from the group consisting of FokI, DNA polymerase, reverse transcriptase, DNA methyltransferase, nucleic acid deaminases, transcription activator(s), transcription repressor(s), histone acetyltransferase and histone deacetylase, or a conjugate thereof;

ii. an mRNA encoding said fusion protein; or iii. a plasmid or a viral vector encoding said fusion protein.

29. Pharmaceutical agents of claim 26 further comprising:

i. a Cas-DNA polymerase fusion protein or a conjugate thereof;

ii. an mRNA encoding a Cas-DNA polymerase fusion protein; or iii. a plasmid or a viral vector encoding a Cas-DNA polymerase fusion protein, wherein the Cas-DNA polymerase fusion protein forms a complex with a guide RNA in targeted cells, and wherein the polymerase uses said nucleic acid template for gene editing.

30. Pharmaceutical agents of claim 26 further comprising lipids.

31. Pharmaceutical agents of claim 26 further comprising cell penetration peptides (CPP).

* * * * *